US012746306B2

(12) United States Patent
Cho et al.

(10) Patent No.: US 12,746,306 B2
(45) **Date of Patent: *Sep. 29, 2026**

(54) HYALURONIC ACID DERIVATIVE AND USE THEREOF

(71) Applicant: AMTIXBIO CO., LTD, Seoul (KR)

(72) Inventors: Seung Woo Cho, Seoul (KR); Jung-Seung Lee, Seoul (KR); Jung Ho Cho, Seoul (KR); Jong-Seung Lee, Seoul (KR)

(73) Assignee: AMTIXBIO CO., LTD., Seoul (KR)

( * ) Notice: Subject to any disclaimer, the term of this patent is extended or adjusted under 35 U.S.C. 154(b) by 259 days.

This patent is subject to a terminal disclaimer.

(21) Appl. No.: 17/842,493

(22) Filed: Jun. 16, 2022

(65) Prior Publication Data

US 2023/0147416 A1 May 11, 2023

Related U.S. Application Data

(62) Division of application No. 16/483,146, filed as application No. PCT/KR2018/001473 on Feb. 2, 2018, now abandoned.

(30) Foreign Application Priority Data

Feb. 2, 2017 (KR) ........................ 10-2017-0014855
Feb. 2, 2017 (KR) ........................ 10-2017-0014856

(51) Int. Cl.

| | |
|---|---|
| ***A61L 27/20*** | (2006.01) |
| ***A61K 38/18*** | (2006.01) |
| ***A61K 47/36*** | (2006.01) |
| ***A61L 27/52*** | (2006.01) |
| ***A61L 27/54*** | (2006.01) |
| ***A61P 17/02*** | (2006.01) |
| ***C08B 37/08*** | (2006.01) |
| ***C08J 3/075*** | (2006.01) |
| ***C08J 3/24*** | (2006.01) |

(52) U.S. Cl.

CPC .......... *A61L 27/20* (2013.01); *A61K 38/1808* (2013.01); *A61K 38/1891* (2013.01); *A61K 47/36* (2013.01); *A61L 27/52* (2013.01); *A61L 27/54* (2013.01); *A61P 17/02* (2018.01); *C08B 37/0072* (2013.01); *C08J 3/075* (2013.01); *C08J 3/24* (2013.01); *C08J 2305/08* (2013.01)

(58) Field of Classification Search

None

See application file for complete search history.

(56) References Cited

FOREIGN PATENT DOCUMENTS

KR 2013/0046283 * 5/2013 ............. A61L 27/28

OTHER PUBLICATIONS

KR 2013/0046283 Google Translation (Year: 2013).*

* cited by examiner

*Primary Examiner* — Craig D Ricci

(74) *Attorney, Agent, or Firm* — United One Law Group LLC; Kongsik Kim; Jhongwoo Peck

(57) ABSTRACT

The present invention provides a hydrogel platform using, as a substrate, hyaluronic acid (HA) conjugated to a pyrogallol (PG) moiety. The HA-PG conjugate of the present invention can be rapidly crosslinked by two different methods, in each of which an oxidizing agent is used or a pH is adjusted. The hydrogel of the present invention can not only have excellent biocompatibility, but also can have efficiently controlled physical characteristics such as a crosslinking rate, elasticity, and adhesive strength, depending on each crosslinking method. On the basis of such excellent stability and functionality, the hydrogel of the present invention can be used in various fields including drug delivery, biopharmaceutical materials such as a wound healing agent or anti-adhesive agent, medicines, and cosmetic products.

6 Claims, 55 Drawing Sheets

Hyaluronic acid (HA)

5'-hydroxydopamine (PG)

Hyaluronic acid derivative

1M HA-PG

200K HA-PG

Perlane

HYALURONIC ACID DERIVATIVE AND USE THEREOF

CROSS-REFERENCE TO RELATED APPLICATIONS

The present application is a divisional application of U.S. application Ser. No. 16/483,146 filed on Aug. 2, 2019, which is a U.S. national phase application of International Application No. PCT/KR2018/001473 filed on Feb. 2, 2018, which claims priority to Korean Application No. 10-2017-0014856 filed on Feb. 2, 2017 and Korean Application No. 10-2017-0014855 filed on Feb. 2, 2017. The applications are incorporated herein by reference.

TECHNICAL FIELD

The present invention relates to a hydrogel based on a hyaluronic acid derivative modified with a gallol group, and a use thereof.

BACKGROUND ART

Interest in functional biomaterials is increasing as markets for medical and biotech industries, cosmetics industry, and the like are rapidly expanding. In particular, development of biocompatible materials using natural polymers for which stability is ensured, rather than chemically synthesized polymers which may cause toxicity or side effects, is becoming more popular.

Various researches and developments have been conducted on hyaluronic acid as a biocompatible material. Hyaluronic acid is a bio-derived polymer which has little side effects when applied to the living body, and is hydrophilic due to a chemical structure of the sugar contained therein. In addition, due to containing a lot of moisture, hyaluronic acid is known to have a physical buffering effect and a lubricating effect on friction in the joints, and to be involved in flexibility of the skin. In addition, hyaluronic acid has protection characteristics against bacterial invasion from the outside and is biodegraded by hyaluronidase in a living body when transplanted into the living body. Hyaluronic acid is utilized as an important material for drug delivery systems by causing the hyaluronic acid to be bound to various drugs. In particular, since approval by the US Food and Drug Administration, hyaluronic acid has been extensively utilized as a medical biomaterial, a material of a scaffold for tissue engineering, and a polymer for drug delivery. In addition, hyaluronic acid is abundantly present in several different layers of the skin, and has complex functions such as a function to supply moisture, a function to assist with tissue of extracellular matrix, a function to act as a filling material, and a function to be involved in tissue regeneration mechanism. However, with aging, amounts of hyaluronic acid, collagen, elastin, and other matrix polymers present in the skin decrease. For example, repeated exposure to ultraviolet rays from the sun causes dermal cells to not only decrease their hyaluronic acid production, but also to have an increased degradation rate of hyaluronic acid. Loss of this material results in wrinkles, holes, moisture loss, and/or other undesirable conditions that contribute to aging. Therefore, as one of methods for improving skin condition, a filler composition containing hyaluronic acid as a main component is widely used.

As conventional hyaluronic acid-related technologies, examples of synthesizing crosslinked insoluble hyaluronic acid derivatives using compounds having two functional groups such as bisepoxide, bishalide, and formaldehyde have been reported in several pieces of literature. In particular, U.S. Pat. No. 4,582,865 discloses an example of using divinylsulfone for crosslinking of hyaluronic acid; U.S. Pat. No. 4,713,448 discloses a crosslinking reaction using formaldehyde; and U.S. Pat. No. 5,356,883 discloses a synthesis example for a hyaluronic acid derivative gel whose carboxyl group has been modified with O-acylurea or N-acylurea using various carbodiimides. However, hyaluronic acid crosslinked products prepared by the methods in these patents have low stability against a hyaluronic acid-degrading enzyme and a high content of unreacted chemicals, which may cause bio-toxicity. In addition, it is not easy to control crosslinking or physical properties of these products depending on an intended use. Thus, there are limitations in applying such products to various medical materials. Therefore, it is still required to develop a technique capable of easily controlling physical properties of a hyaluronic acid hydrogel while maintaining excellent biocompatibility thereof.

Accordingly, in order to solve these problems, the present inventors have continually made efforts to develop a technique capable of improving functionality of hyaluronic acid which is a biocompatible material. As a result, the present inventors have developed a hydrogel platform technique based on hyaluronic acid modified with a pyrogallol group, and have completed the present invention on the basis of this technique.

SUMMARY OF DISCLOSURE

Accordingly, an object of the present invention is to provide a hyaluronic acid derivative prepared by modifying hyaluronic acid with a pyrogallol group and a method for preparing the same.

Another object of the present invention is to provide a method for preparing a hyaluronic acid derivative hydrogel, comprising a step of crosslinking the hyaluronic acid derivatives.

Yet another object of the present invention is to provide a hyaluronic acid derivative hydrogel having a structure in which the hyaluronic acid derivatives are crosslinked.

Still yet another object of the present invention is to provide a drug delivery carrier or drug delivery system (DDS) using the hyaluronic acid derivative hydrogel.

Still yet another object of the present invention is to provide a medical material such as a scaffold for tissue engineering, using the hyaluronic acid derivative hydrogel.

Still yet another object of the present invention is to provide a wound dressing or adhesion barrier based on the hyaluronic acid derivative.

Still yet another object of the present invention is to provide a filler composition comprising the hyaluronic acid derivative hydrogel.

Still yet another object of the present invention is to provide a method for improving skin wrinkles, comprising a step of injecting the filler composition into or under the skin of an individual.

However, the technical problems to be solved by the present invention are not limited to the above-mentioned problems, and other problems not mentioned can be clearly understood by those skilled in the art from the following description.

In order to achieve the objects of the present invention as described above, the present invention provides a method for preparing a hyaluronic acid hydrogel, the method comprising a step of crosslinking hyaluronic acid derivatives, each of which is modified with a gallol group, wherein the hyaluronic acid derivative has been modified with a gallol group due to a reaction between hyaluronic acid and 5'-hydroxydopamine.

In an embodiment of the present invention, the hyaluronic acid derivative may be represented by the following Formula 1, wherein the hyaluronic acid derivative may have a molecular weight of 10,000 Da to 2,000,000 Da, and may have a gallol group substitution rate of about 0.1% to 50%.

[Formula 1]

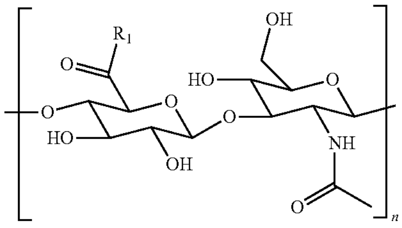

In the above Formula 1, $R_1$ is a hydroxyl group or

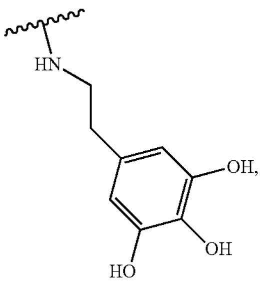 [SMILES: *NCCc1cc(O)c(O)c(O)c1]

and n is an integer of 1 to 1000.

In another embodiment of the present invention, in the crosslinking step, crosslinking may be carried out by adding an oxidizing agent or a pH adjusting agent, in which the oxidizing agent may be sodium periodate, hydrogen peroxide, horseradish peroxidase, or tyrosinase, and the pH adjusting agent may be sodium hydroxide, lithium hydroxide, potassium hydroxide, rubidium hydroxide, cesium hydroxide, magnesium hydroxide, calcium hydroxide, strontium hydroxide, or barium hydroxide.

In yet another embodiment of the present invention, in the crosslinking step carried out by adding the oxidizing agent, crosslinking represented by the following Formula 2 may be formed between the hyaluronic acid derivatives.

[Formula 2]

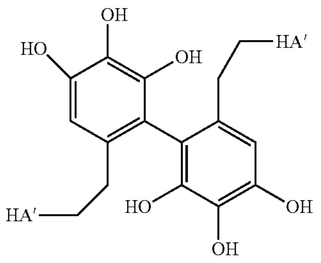

In the above Formula 2, HA' represents hyaluronic acid in which the carboxyl group is substituted with an amide group.

As still yet another embodiment of the present invention, in the crosslinking step carried out by adding the pH adjusting agent, crosslinking represented by the following Formula 3 may be formed between the hyaluronic acid derivatives.

[Formula 3]

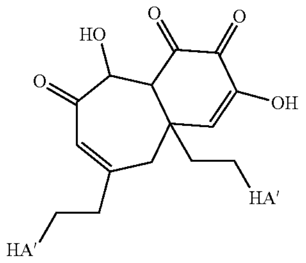

In the above Formula 3, HA' represents hyaluronic acid in which a carboxy group is substituted with an amide group.

In addition, the present invention provides a hyaluronic acid hydrogel prepared by crosslinking hyaluronic acid derivatives, each of which is represented by the above Formula 1, for example, a hyaluronic acid hydrogel in which crosslinking represented by the above Formula 2 or Formula 3 is formed between the hyaluronic acid derivatives; and a carrier for delivery of a bioactive substance, comprising the hyaluronic acid hydrogel. From this viewpoint, in an embodiment of the present invention, the carrier includes, but is not limited to, an antibody, an antibody fragment, a protein, a peptide, a polypeptide, a small molecule chemical compound, DNA and/or RNA, siRNA, a gene, and stem cells including adult stem cells, mesenchymal stem cells, or induced pluripotent stem cells (iPSCs). From this viewpoint, in another embodiment of the present invention, the carrier for delivery of a bioactive substance provides sustained release of the bioactive substance in vivo and ex vivo.

In addition, the present invention provides a hyaluronic acid hydrogel prepared by crosslinking hyaluronic acid derivatives, each of which is represented by the above Formula 1, for example, a hyaluronic acid hydrogel in which crosslinking represented by the above Formula 2 or Formula 3 is formed between the hyaluronic acid derivatives; and a scaffold for tissue engineering, comprising the hyaluronic acid hydrogel.

In addition, the present invention provides a filler composition, comprising a hyaluronic acid derivative modified with a gallol group or a hyaluronic acid derivative hydrogel prepared by crosslinking the hyaluronic acid derivatives.

In an embodiment of the present invention according to this purpose, the hyaluronic acid derivative may have a molecular weight of 10,000 Da to 2,000,000 Da; and the hyaluronic acid derivative may have a pyrogallol group substitution rate of 0.1% to 50%, preferably 1% to 30%, and more preferably 2% to 20%. In another embodiment of the present invention, the hyaluronic acid derivative may be contained in an amount of 0.1% (w/v) to 15% (w/v) with respect to the entire filler composition.

In yet another embodiment of the present invention, the filler composition may be in a liquid state ex vivo and may form a gelated state in vivo without a crosslinking agent. In still yet another embodiment of the present invention, the filler composition may be injected into any one site selected from the group consisting of a tear trough region, a glabellar frown line region, an eye-rim region, a forehead region, a nasal bridge region, a nasolabial line region, a marionette line region, and a neck wrinkle region. In still yet another embodiment of the present invention, the filler composition may further comprise any one cell growth factor selected from the group consisting of fibroblast growth factor (FGF), epithelial cell growth factor (EGF), keratinocyte growth factor (KGF), transforming growth factor alpha (TGF-a), transforming growth factor beta (TGF-β), granulocyte colony stimulating factor (GCSF), insulin-like growth factor (IGF), vascular endothelial growth factor (VEGF), hepatocyte growth factor (HGF), platelet-derived growth factor-BB (PDGF-BB), brain-derived neurotrophic factor (BDNF), and glial cell-derived neurotrophic factor (GDNF). In still yet another embodiment of the present invention, the filler composition may further comprise any one component selected from the group consisting of a local anesthetic, an antioxidant, a vitamin, and combinations thereof.

In addition, the present invention provides a method for preparing a filler composition, comprising a step of introducing a pyrogallol group into a skeleton of glucuronic acid in hyaluronic acid, to prepare a hyaluronic acid derivative; and a step of adding the hyaluronic acid derivative to an aqueous medium and performing mixing.

In addition, the present invention provides a method for improving skin wrinkles, comprising a step of injecting the filler composition into or under the skin of an individual.

In addition, the present invention provides a wound healing agent or adhesion barrier, comprising a hyaluronic acid derivative modified with a gallol group or a hyaluronic acid derivative hydrogel prepared by crosslinking the hyaluronic acid derivatives.

The technique for preparing a hyaluronic acid hydrogel according to the present invention is based on a hyaluronic acid derivative modified with a gallol group, and includes a step of crosslinking the hyaluronic acid derivatives under an appropriate oxidizing or specific pH condition. The present invention makes it possible to effectively control physical properties of a hydrogel such as crosslinking rate, elasticity, and adhesive strength depending on each crosslinking method, while allowing the hydrogel to have excellent biocompatibility.

Thus, the present invention can be utilized for various fields such as the medical field and the cosmetics field.

BRIEF DESCRIPTION OF DRAWINGS

FIG. 6A illustrates results obtained by visually identifying hydrogel formation over time, and FIG. 6B illustrates results obtained by identifying changes in elastic modulus of the hydrogels over time.

FIG. 7A illustrates results obtained by identifying changes in elastic modulus of the hydrogels at 0.1 to 1 Hz, and FIG. 7B illustrates results obtained by comparing elastic modulus and tan δ (G"/G') of the hydrogels.

FIG. 8A illustrates results obtained by identifying changes in elastic modulus of the hydrogels at 0.1 to 1 Hz, and FIG. 8B illustrates results obtained by comparing elastic modulus and tan δ (G"/G') of the hydrogels.

FIG. 9A illustrates a result obtained by measuring, with a rheological instrument, changes in force applied depending on a distance between plates, and FIG. 9B illustrates a result obtained by quantifying and evaluating adhesive strength.

FIGS. 11A and 11B respectively illustrate live/dead staining (scale bar=100 μm) (FIG. 11A) and viability (FIG. 11B) of hADSCs at days 1, 3, and 7 after encapsulation of the hADSCs in order to evaluate toxicity of HA-PG hydrogels. FIG. 11C illustrates a result obtained by performing an enzyme-linked immunoadsorption assay for quantification of TNF-α secreted from macrophages (RAW 264.7) when co-cultured with a $NaIO_4$ or NaOH solution-crosslinked HA-PG hydrogel (n=4,**p<0.01 vs LPS group).

FIG. 12A illustrates shapes of HA-PG hydrogels (DS 8%) recovered from a subcutaneous region of a mouse on days 0, 7, 28, and 84 after being transplanted into the subcutaneous region. FIG. 12B illustrates in vivo biodegradation profiles of the HA-PG hydrogels. FIGS. 12C and 12D respectively illustrate H&E staining and toluidine blue staining of the hydrogels recovered together with adjacent tissue on day 28 after transplantation (scale bar=300 μm).

FIG. 13A illustrates results obtained by visually identifying changes in volume of the hydrogels, and FIG. 13B illustrates results obtained by identifying weights of the remaining hydrogels, after the hydrogels are subcutaneously transplanted into mice.

FIG. 14A illustrates results obtained by identifying formation and presence of microparticles before or after freeze-drying, and FIG. 14B illustrates a result obtained by identifying released amounts of BSA which has been encapsulated in the microparticles.

FIG. 15A illustrates a crosslinking reaction using $NaIO_4$, FIG. 15B illustrates a microscope photograph showing formation of HA-PG microparticles (scale bar=50 μm), and FIG. 15C illustrates a cumulative amount of VEGF released from a bulk HA-PG hydrogel or HA-PG microparticles (PBS, 37° C.) (n=4).

FIG. 16A illustrates photographs showing results obtained by intramuscularly injecting HA-PG microparticles containing VEGF and making an observation at day 0 (day of drug injection) and day 28, FIG. 16B illustrates a numerical representation of the results (n=4 to 5), FIG. 16C illustrates results of H&E staining and MT staining, using normal mouse tissue as a control (scale bar=100 μm), FIG. 16D illustrates a result obtained by quantifying fibrotic area in an ischemic leg (n=12, $p<0.01$ vs PBS group, ##$p<0.01$ vs HA-PG group, and @$p<0.05$ vs VEGF group), and FIG. 16E illustrates photographs of ischemic leg muscle which has been immunostained for α-SMA (arteriole formation) and vWF (capillary formation). Black arrows indicate formation of arteriole (α-SMA positive) and capillary (vWF positive) in ischemic tissue, respectively (scale bar=100 μm). FIG. 16**F illustrates the number of α-SMA positively stained lumens and vWF positive capillaries in ischemic muscle (n=18.20, *$p<0.05$, and **$p<0.01$ vs PBS group, ##$p<0.01$ vs HA-PG group, and @$p<0.01$ vs VEGF group).

FIG. 17A illustrates formation of a hyaluronic acid derivative hydrogel by NaOH-mediated crosslinking. FIG. 17B illustrates a result obtained by comparing adhesive strength between a hyaluronic acid derivative hydrogel crosslinked with NaOH and a hyaluronic acid derivative hydrogel crosslinked with $NaIO_4$. FIG. 17C illustrates a result obtained by comparing mean detachment strength between the respective HA-PG hydrogels (n=3, **$p<0.01$ vs $NaIO_4$ group).

FIGS. 20A and 20B illustrate gelation of an HA-PG solution according to the present invention by oxidizing power in the body, in which FIG. 20A illustrates injection of the HA-PG solution and gelation thereof by oxidizing power in the body; and FIG. 20B illustrates a result obtained by visually identifying the skin of a mouse which contains a hydrogel formed in the body.

FIGS. 21A and 21B illustrate results obtained by injecting the HA-PG solution according to the present invention into the skin, and then identifying whether the hydrogel formed in the body is maintained in the body, in which FIG. 21A illustrates results obtained by visually identifying the hydrogel formed in the body (weeks 0, 10, and 24); and FIG. 21B illustrates a result obtained by measuring changes in weight of the hydrogel formed in the body for about 6 months.

FIGS. 22A and 22B illustrate results obtained by identifying conditions for formation of an HA-PG hydrogel of the HA-PG solution according to the present invention and for injection thereof into the body, in which FIG. 22A illustrates a schematic view showing a process of forming the HA-PG hydrogel; and FIG. 22B illustrates a result obtained by comparing a needle size which is injectable into the body with conventional filler products (Megafill, Perlane).

FIGS. 23A and 23B illustrate results obtained by injecting the HA-PG solution according to the present invention into the skin, and then identifying wrinkle-improving effects before and after the injection, in which FIG. 23A illustrates a result obtained by causing the wrinkled skin to be made into replicas and making a comparison; and FIG. 23B illustrates results obtained by quantifying the area, length, and depth of the wrinkles and making a comparison.

FIGS. 24A and 24B illustrate results obtained by making a comparison with conventional filler products (Megafill, Perlane) in terms of ability to be maintained in the body, in which FIG. 24A illustrates results obtained by injecting, into the skin, the HA-PG solutions according to the present invention (200 KDa, 1 MDa), the Megafill product, and the Perlane product, and then visually identifying the hydrogels formed in the body (days 0, 14, 28, 56, 84, 168, and 252); and FIG. 24B illustrates a result obtained by measuring changes in weight of the hydrogels formed in the body for about 9 months.

FIGS. 25A and 25B illustrate results obtained by making a comparison with conventional filler products (Megafill, Perlane) in terms of ability to be maintained in the body, in which FIG. 25A illustrates results obtained by injecting, into the skin, the HA-PG solutions according to the present invention (200 KDa, 1 MDa), the Megafill product, and the Perlane product, and then visually identifying the hydrogels formed in the body (days 0, 14, 28, 56, 84, and 168); and FIG. 25B illustrates a result obtained by measuring changes in volume of the hydrogels formed in the body for about 9 months.

FIGS. 26A and 26B illustrate results obtained by identifying adhesive strength in the body of the hydrogel formed in the body, in which FIG. 26A illustrates a result for the Perlane product; and FIG. 26B illustrates results for the HA-PG solutions (200 KDa, 1 MDa).

KDa, 1 MDa), the Megafill product, and the Perlane product using injection needles of various sizes (21 G, 25 G, 29 G, 30 G).

Figure 28B:
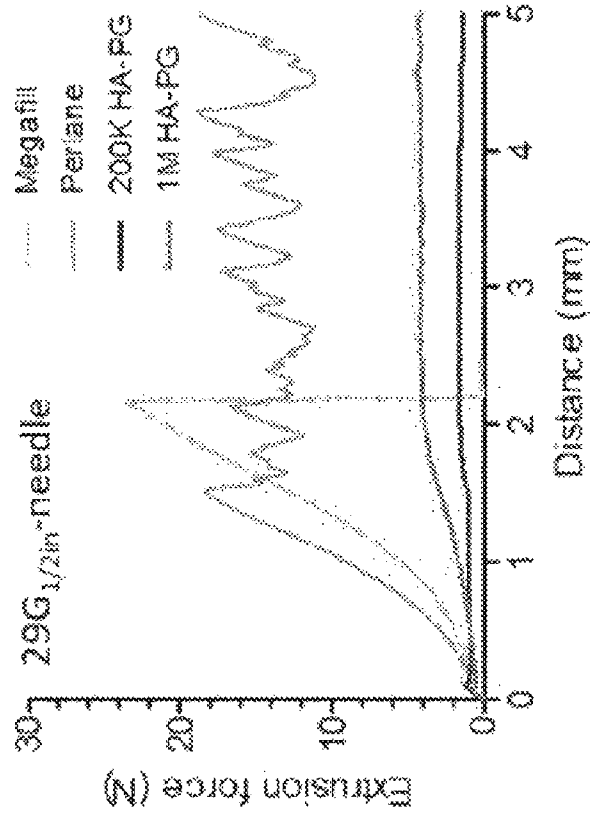
Figure 28A:
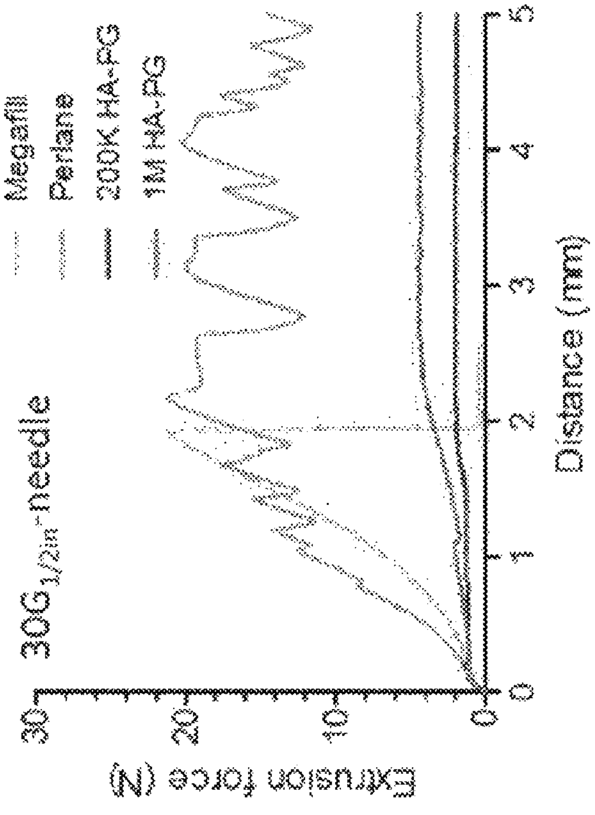

FIGS. 28A and 28B illustrate results obtained by making a comparison with conventional filler products (Megafill, Perlane) in terms of injectability, in which FIG. 28A illustrates a result obtained by identifying changes in extrusion force while injecting the HA-PG solutions according to the present invention (200 KDa, 1 MDa), the Megafill product, and the Perlane product using an injection needle of 30 G; and FIG. 28B illustrates a result obtained by identifying changes in extrusion force while injecting the HA-PG solutions according to the present invention (200 KDa, 1 MDa), the Megafill product, and the Perlane product using an injection needle of 29 G.

Figure 29B:
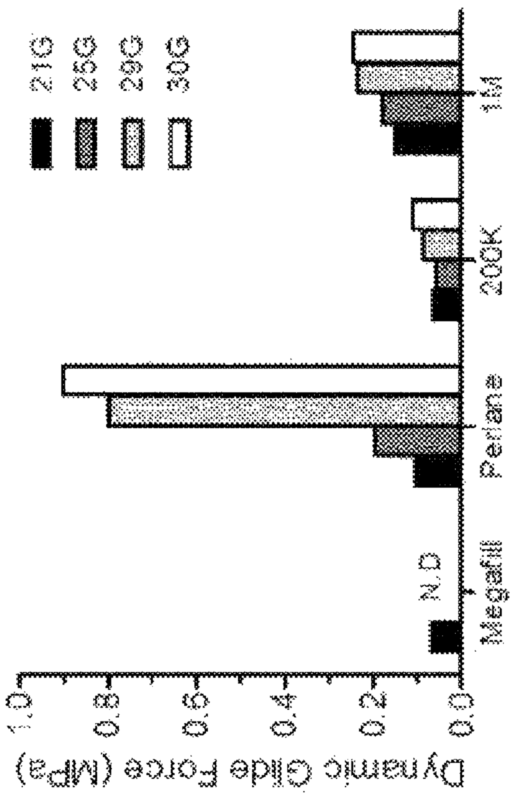
Figure 29A:
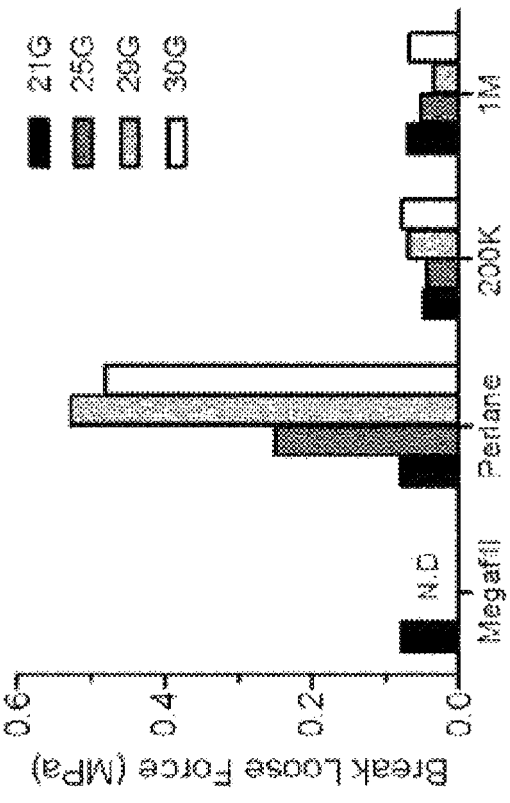

FIGS. 29A and 29B illustrate results obtained by making a comparison with conventional filler products (Megafill, Perlane) in terms of injectability, in which FIG. 29A illustrates a result obtained by comparing break loose forces while injecting the HA-PG solutions according to the present invention (200 KDa, 1 MDa), the Megafill product, and the Perlane product using injection needles of various sizes (21 G, 25 G, 29 G, 30 G); and FIG. 29B illustrates a result obtained by comparing dynamic glide forces while injecting the HA-PG solutions according to the present invention (200 KDa, 1 MDa), the Megafill product, and the Perlane product using injection needles of various sizes (21 G, 25 G, 29 G, 30 G).

Figure 30A:
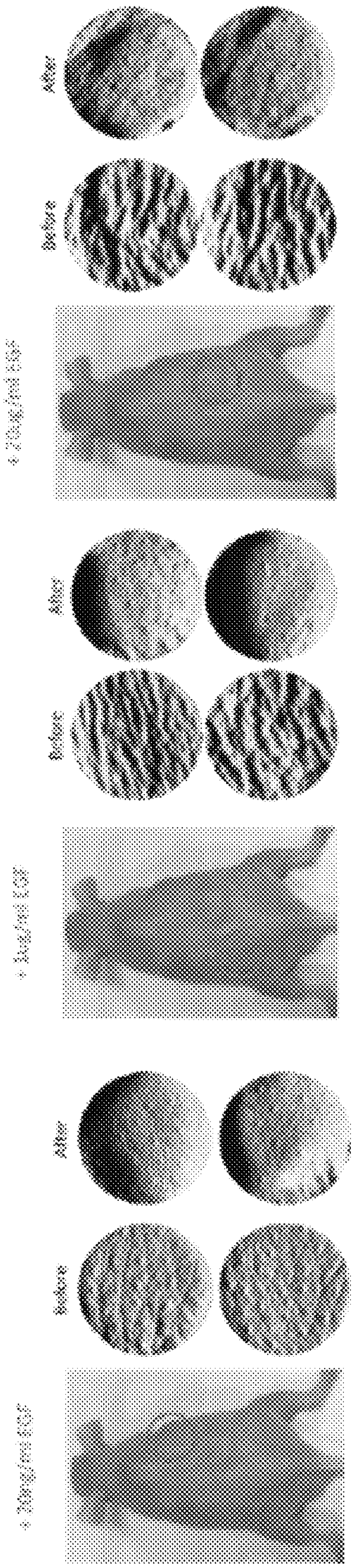
Figure 30B:
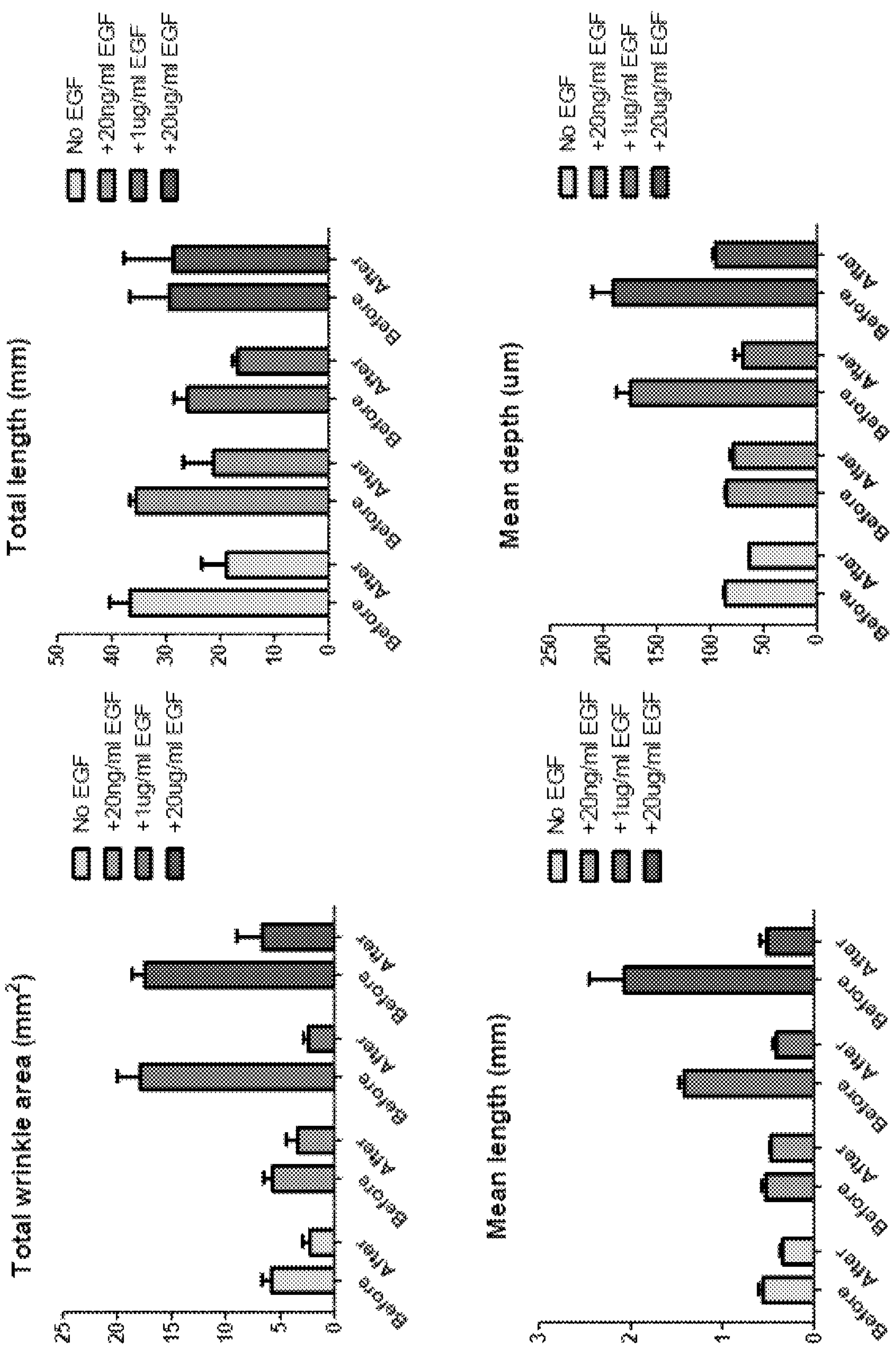

FIGS. 30A and 30B illustrate results obtained by injecting, into the skin, the HA-PG solutions according to the present invention in which epithelial cell growth factor (20 ng/ml, 1 μg/ml, 20 μg/ml) has been encapsulated, and then identifying wrinkle-improving effects before and after the injection, in which FIG. 30A illustrates results obtained by causing the wrinkled skin to be made into replicas and making a comparison; and FIG. 30B illustrates results obtained by quantifying the area, length, and depth of the wrinkles and making a comparison.

Figure 31:
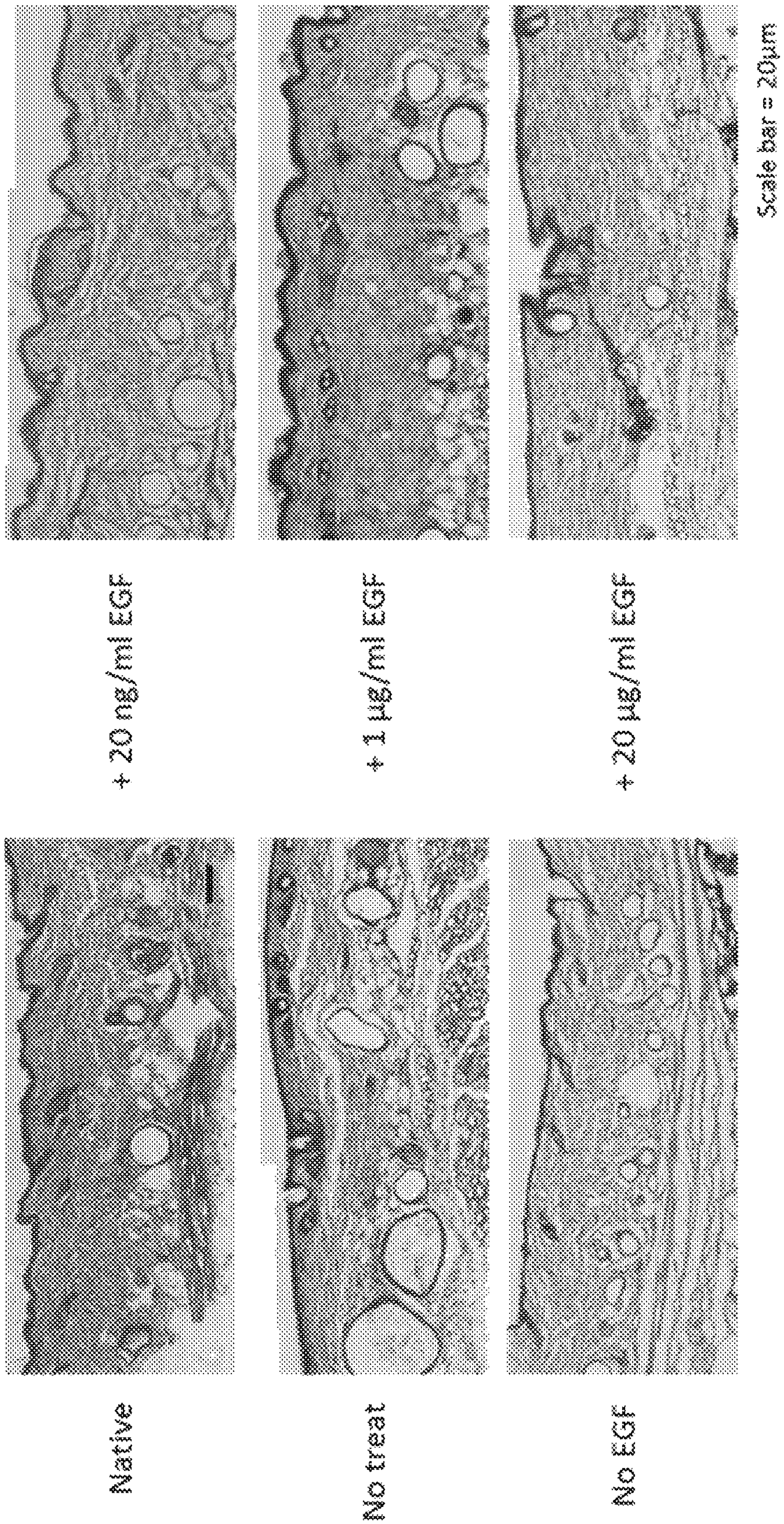

FIG. 31 illustrates results obtained by injecting, into the skin, the HA-PG solutions according to the present invention in which epithelial cell growth factor (20 ng/ml, 1 μg/ml, 20 μg/ml) has been encapsulated, performing H&E staining of OCT frozen sections thereof, and performing histopathological examination.

Figure 32:
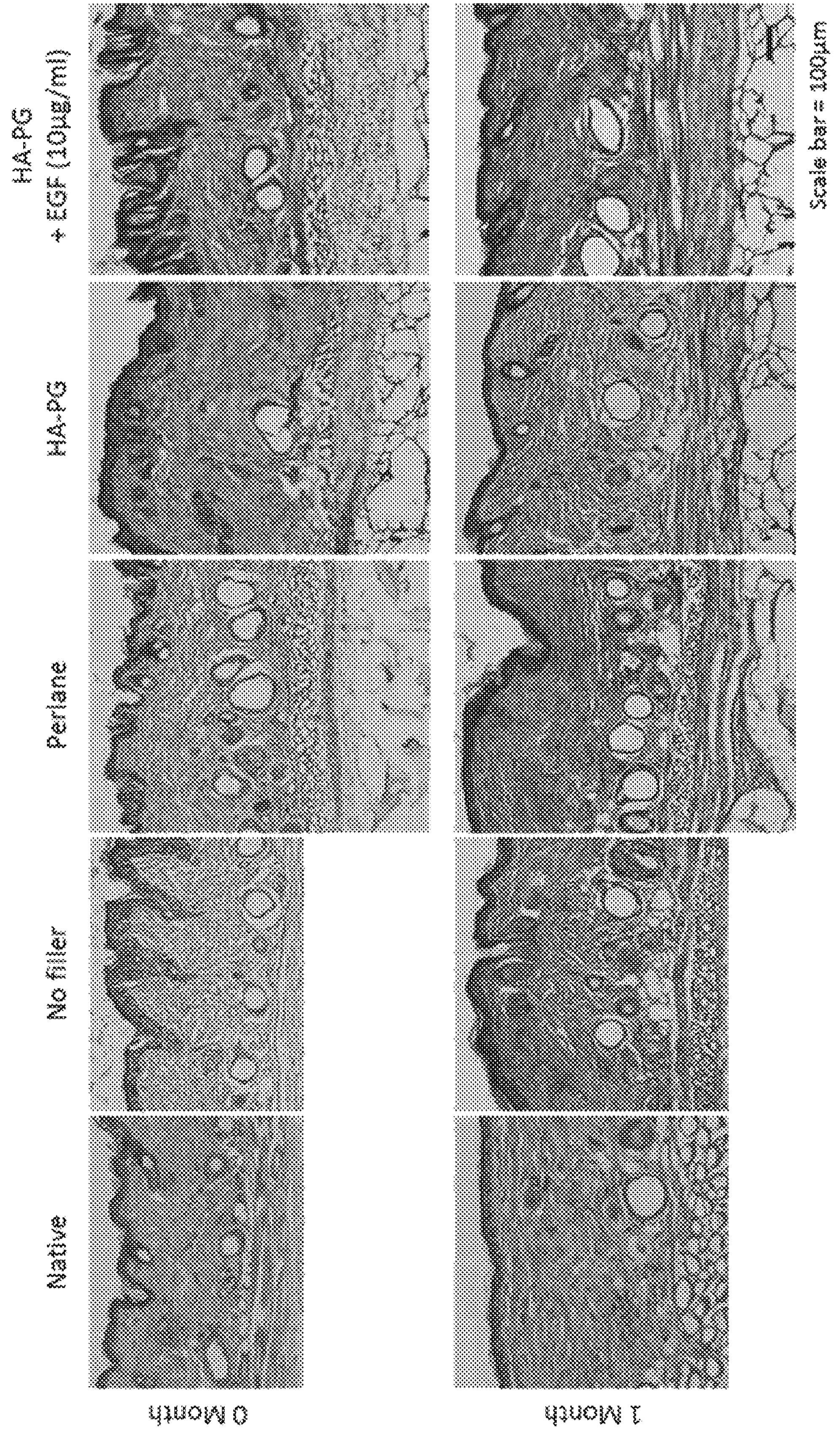

FIG. 32 illustrates results obtained by comparing skin tissue-regenerating effects over time (1 month) among a conventional filler product (Perlane), the HA-PG solution in which epithelial cell growth factor has not been encapsulated, and the HA-PG solution according to the present invention in which epithelial cell growth factor (10 μg/ml) has been encapsulated, and such results were obtained by performing H&E staining of OCT frozen sections thereof and performing histopathological examination.

Figure 33:
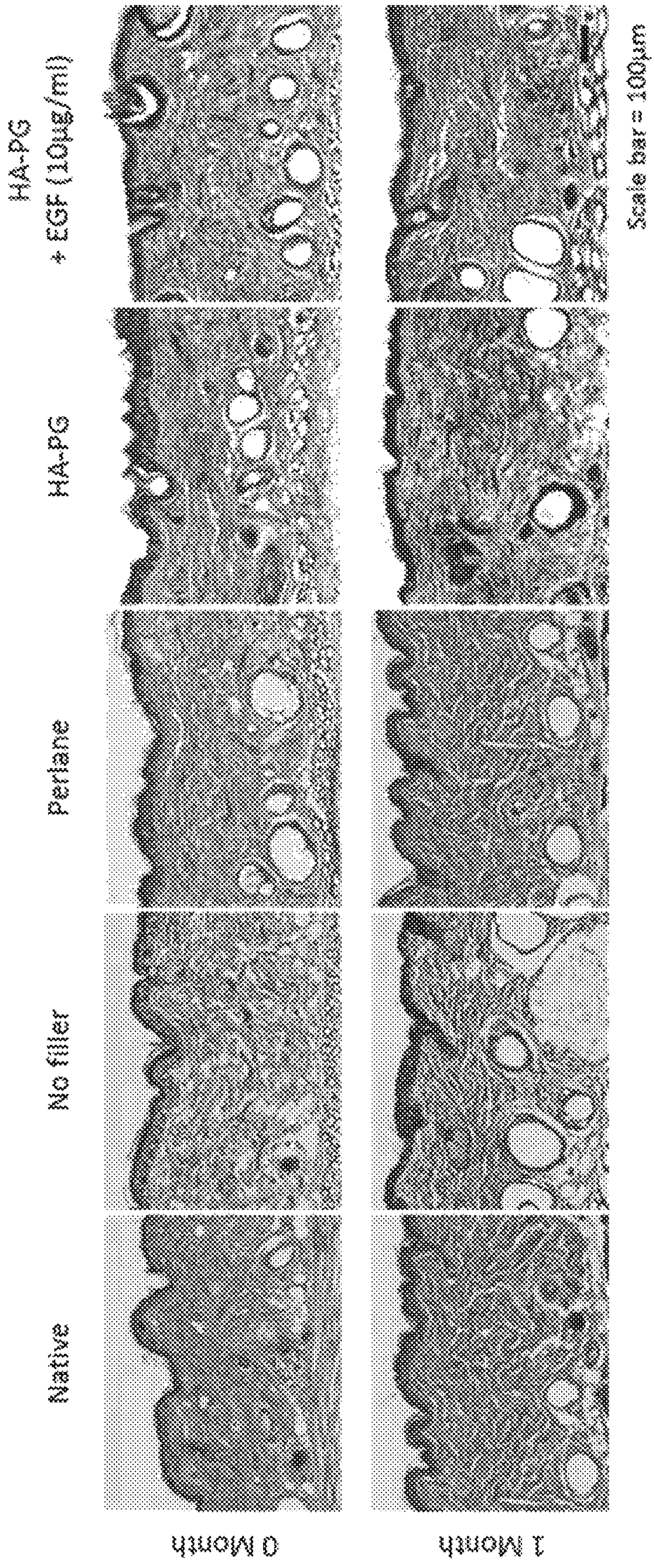

FIG. 33 illustrates results obtained by comparing skin tissue-regenerating effects over time (1 month) among a conventional filler product (Perlane), the HA-PG solution in which epithelial cell growth factor has not been encapsulated, and the HA-PG solution according to the present invention in which epithelial cell growth factor (10 μg/ml) has been encapsulated, and such results were obtained by performing Masson's trichrome (MT) staining of OCT frozen sections thereof and performing histopathological examination.

Figure 34:
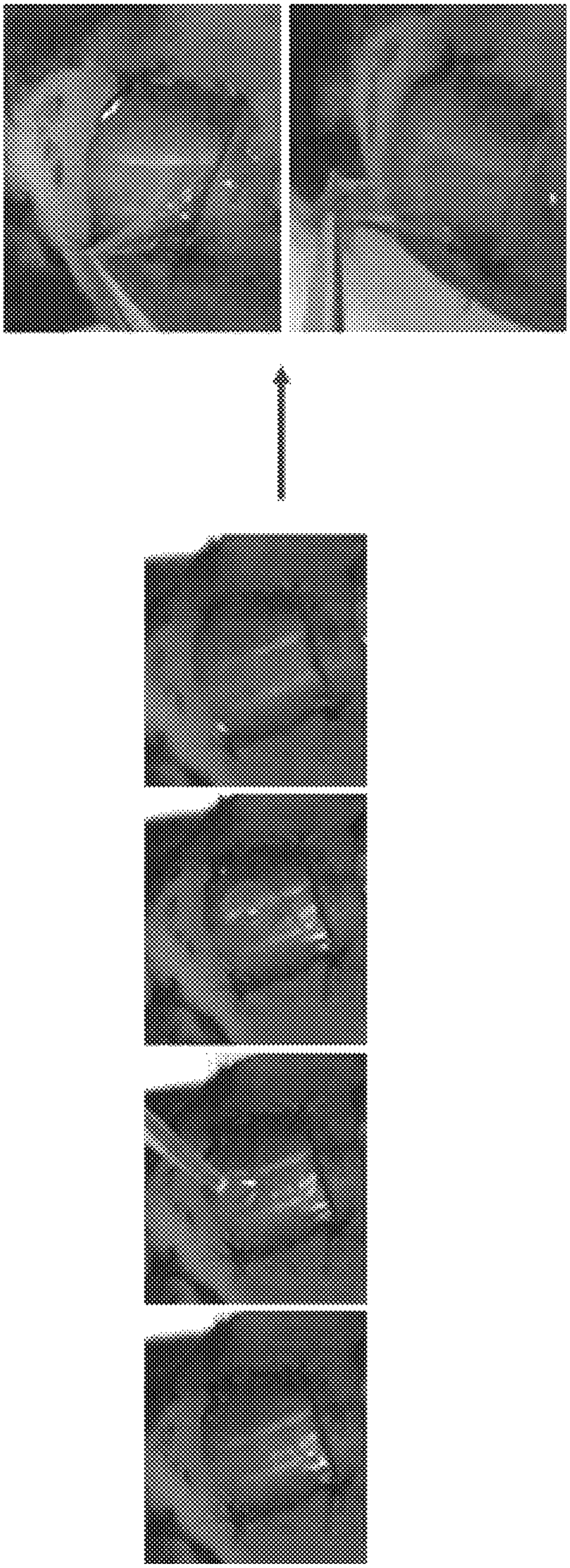

FIG. 34 illustrates results obtained by applying the HA-PG solution according to the present invention to a wound site, and then visually identifying whether a hydrogel is formed at the wound site, and thus the hydrogel is adhered thereto.

Figure 35:
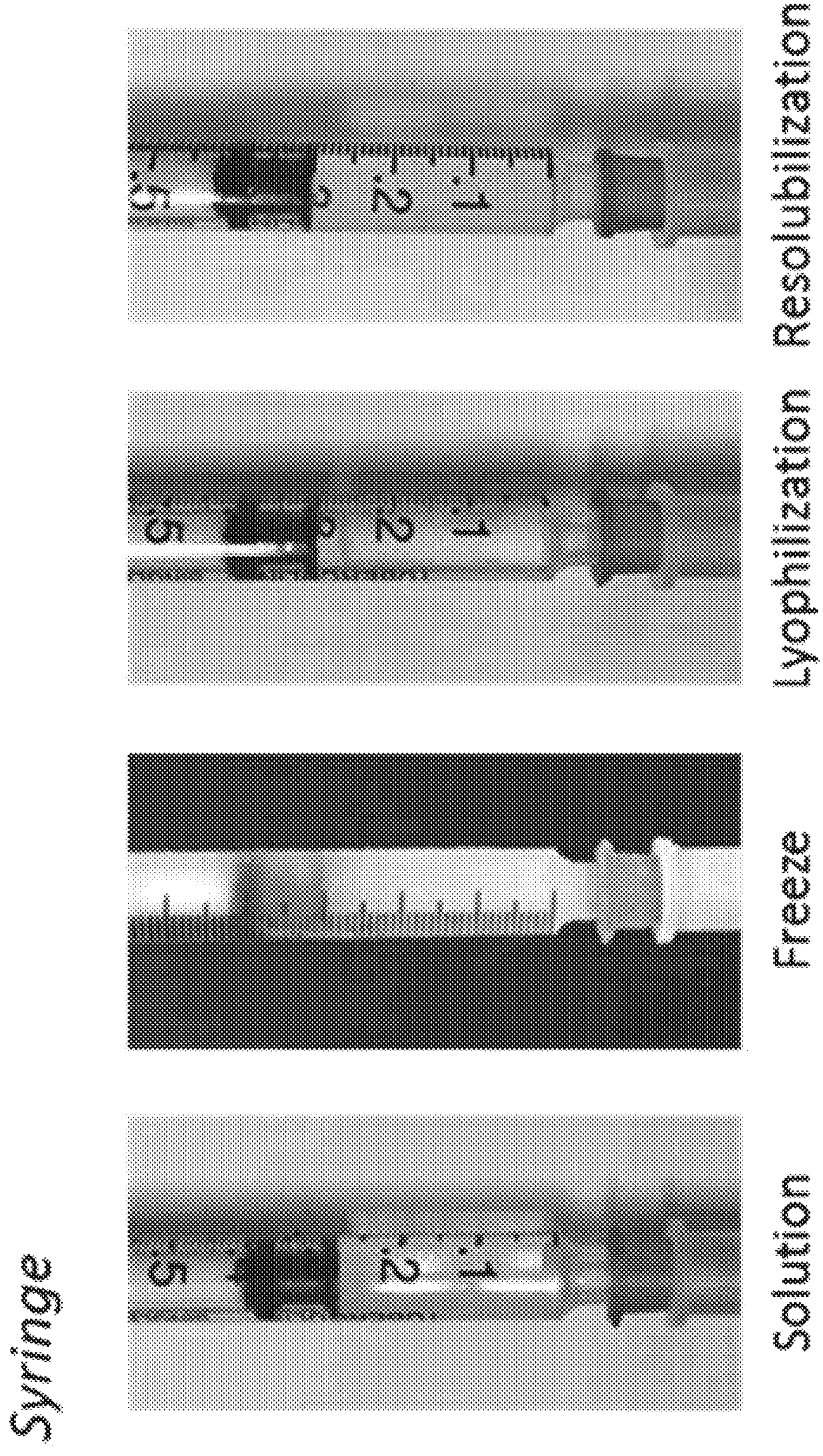

FIG. 35 illustrates a view briefly showing a process of formulating the HA-PG solution according to the present invention into a powder form.

Figure 36:
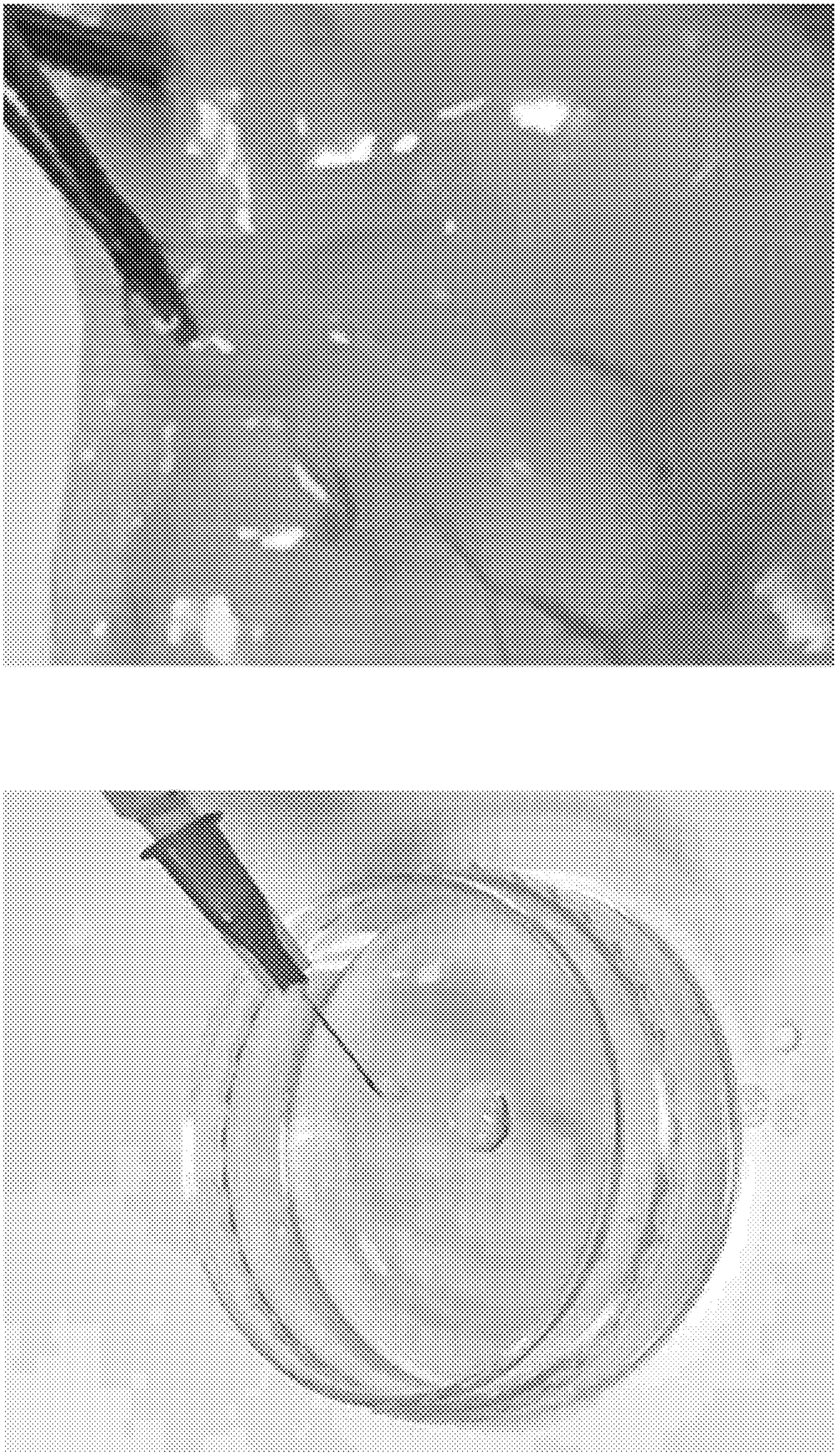

FIG. 36 illustrates results obtained by injecting, into the skin, the HA-PG solution according to the present invention which has been re-solubilized from a freeze-dried powder form thereof, and then visually identifying a hydrogel formed in the body.

Figure 37:
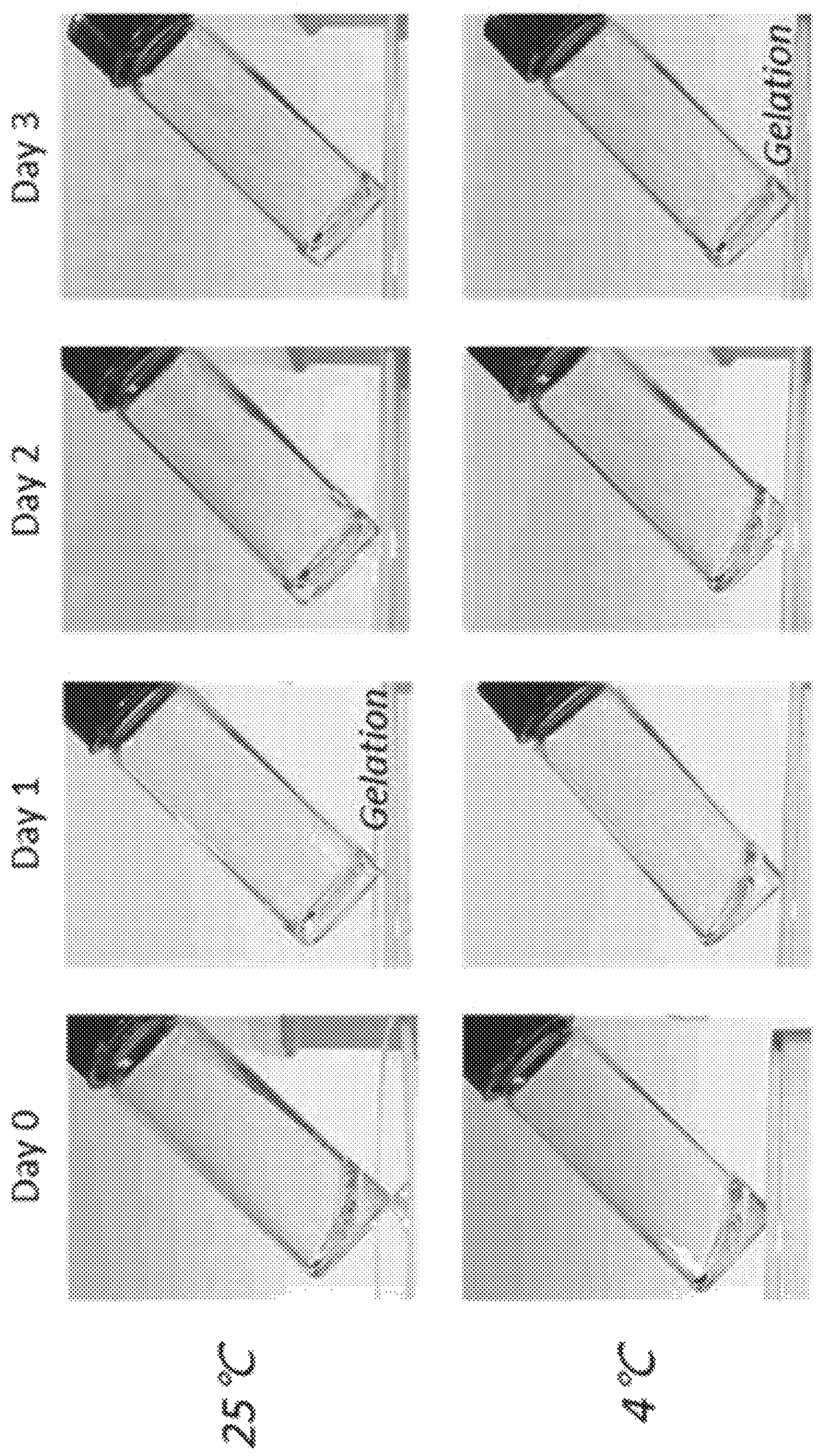

FIG. 37 illustrates results obtained by identifying storage stability of the HA-PG solution according to the present invention, and such results were obtained by identifying whether or not the HA-PG solution is gelated in a storage container while storing the HA-PG solution at room temperature (25° C.) or in a refrigerated state (4° C.).

Figure 38:
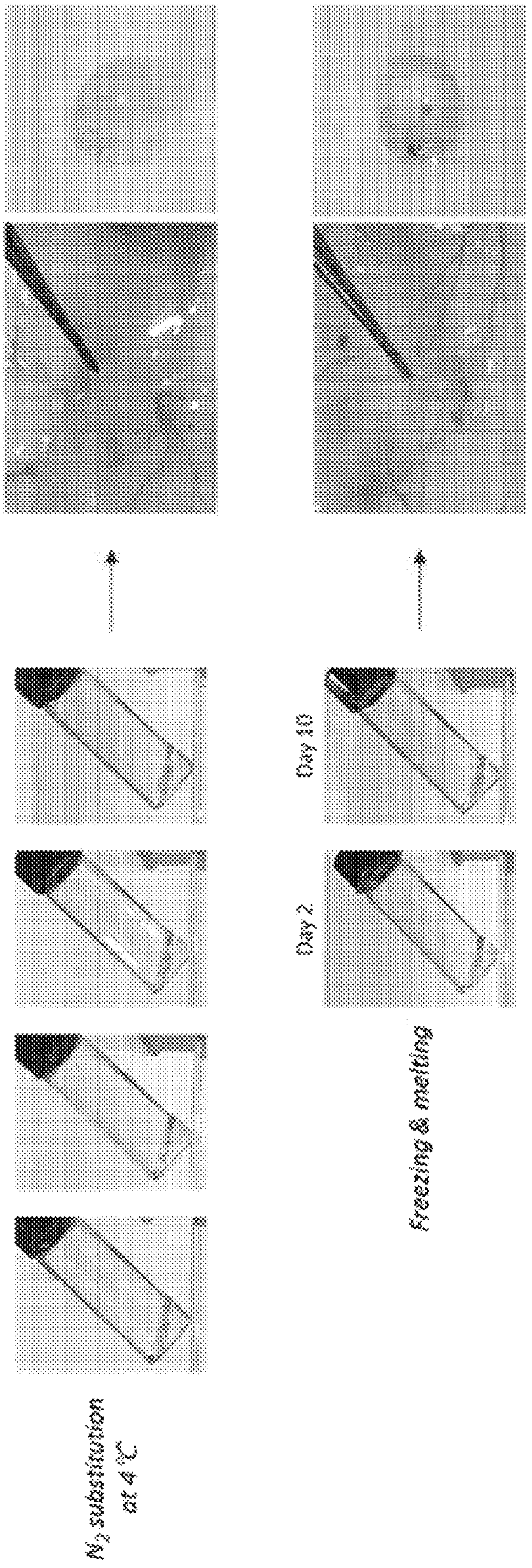

FIG. 38 illustrates results obtained by identifying storage stability of the HA-PG solution according to the present invention. Nitrogen gas was injected into a storage container to block contact between the HA-PG solution and oxygen, and then the HA-PG solution was stored in a refrigerated state (4° C.) for 3 days; on the other hand, the HA-PG solution was stored in a frozen state (−80° C.) for 10 days. Then, these solutions were injected into the skin, and hydrogels formed in the body were visually identified, so that the results were obtained.

DETAILED DESCRIPTION

Hereinafter, the present invention will be described in detail.

The present invention provides a method for preparing a hyaluronic acid hydrogel, the method comprising a step of crosslinking hyaluronic acid derivatives, each of which is modified with a gallol group, wherein the hyaluronic acid derivative has been modified with a gallol group due to a reaction between hyaluronic acid and 5'-hydroxydopamine.

The term "hyaluronic acid (HA)" as used herein refers to a high molecular linear polysaccharide which contains, as a repeating unit, a disaccharide in which D-glucuronic acid (GlcA) and N-acetyl-D-glucosamine (GlcNAc) are linked via β 1,3-glycosidic bond, and includes both hyaluronic acid and salts thereof. For the salts, a sodium salt, a potassium salt, a magnesium salt, a calcium salt, an aluminum salt, and the like are exemplified, but are not limited thereto.

The disaccharide repeating unit of hyaluronic acid may be represented by the following Formula 4, and may be 1 to 1,000, but is not limited thereto.

[Formula 4]

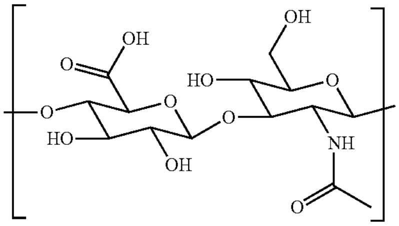

Hyaluronic acid is found in ocular vitreous humor, joint synovial fluid, chicken comb, and the like, and is known as a highly biocompatible biomaterial. Despite high applicability of a hyaluronic acid hydrogel to biomaterials, limited mechanical properties due to a natural polymer itself make it difficult for the hyaluronic acid hydrogel to be applied to biomaterials (for example, drug delivery carrier, scaffold for tissue engineering). Thus, the present inventors have introduced a gallol group having a high oxidizing ability into hyaluronic acid to prepare a hyaluronic acid derivative (Preparation Example 1), and have crosslinked such hyaluronic acid derivatives under an appropriate oxidizing or specific pH (pH 8 to 9) condition to prepare a hydrogel (Preparation Example 2). Accordingly, the present invention has technical significance in that physical properties such as crosslinking rate, elasticity, and adhesive strength of a hydrogel can be efficiently controlled (Examples 1 and 3).

The term “hyaluronic acid derivative” or “hyaluronic acid-pyrogallol conjugate” as used herein is interpreted as including both hyaluronic acid or a salt thereof in which a gallol group is introduced into a skeleton of glucuronic acid in the hyaluronic acid or the salt thereof.

As an embodiment, the hyaluronic acid derivative may be prepared by a reaction between a terminal of the disaccharide repeating unit of the above Formula 4, specifically, a carboxyl group thereof and 5'-hydroxydopamine. The hyaluronic acid derivative prepared by the reaction contains at least one repeating unit represented by the following Formula 5, and may be represented by the following Formula 1.

[Formula 5]

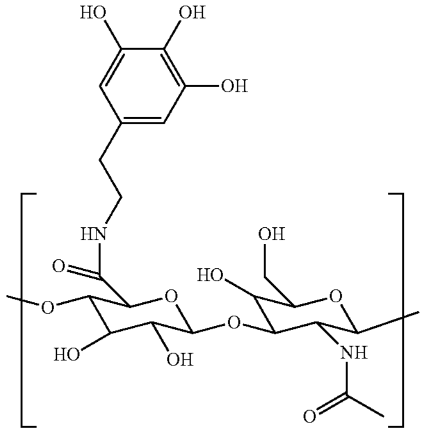

[Formula 1]

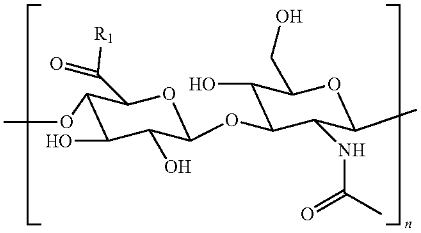

In the above Formula 1, $R_1$ is a hydroxyl group or

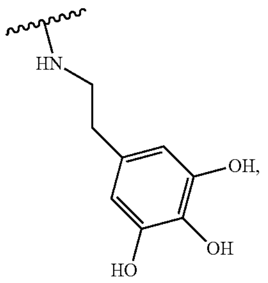 [SMILES: *NCCc1cc(O)c(O)c(O)c1]

and n is an integer of 1 to 1,000.

In addition, the hyaluronic acid derivative may have a molecular weight of 10,000 Da to 2,000,000 Da, and the hyaluronic acid derivative may have a gallol group substitution rate of 0.1% to 50%, but the pyrogallol group substitution rate is not limited thereto.

The “substitution rate” means that a specific functional group in hyaluronic acid or a salt thereof is replaced or modified with a gallol group. The rate of being substituted with the gallol group is defined as a rate of repeating units into which the gallol group has been introduced in the entire hyaluronic acid repeating units, and may be represented, by definition, as a numerical value from more than 0 to equal to or less than 1, a numerical value from more than 0% and equal to or less than 100%, or a numerical value from more than 0% by mol to equal to or less than 100% by mol.

The term “hydrogel” as used herein means a three-dimensional structure of a hydrophilic polymer retaining a sufficient amount of moisture. For the purpose of the present invention, the hydrogel indicates a hydrogel formed of hyaluronic acid derivatives, each of which is modified with a gallol group.

A process of preparing the hyaluronic acid hydrogel may be carried out by a crosslinking reaction between the hyaluronic acid derivatives. For the crosslinking reaction, the process may further include a step of mixing the hyaluronic acid derivatives with PBS and the like to prepare a hyaluronic acid hydrogel precursor solution. Such crosslinking may be performed by chemical crosslinking caused by UV irradiation, physical crosslinking, or biological crosslinking, to form a hydrogel. Here, the chemical crosslinking caused by UV irradiation includes photo-crosslinking, crosslinking utilizing a reactive crosslinker, or the like. The biological crosslinking includes crosslinking utilizing a binding force between heparin and growth factor, crosslinking using complementary bonding of DNA or the like, and the like. The physical crosslinking includes crosslinking by hydrogen bonding, crosslinking by hydrophobic interaction, crosslinking utilizing electrostatic interaction, or the like. Preferably, crosslinking may be performed by adding an oxidizing agent or a pH adjusting agent. The oxidizing agent may be sodium periodate, hydrogen peroxide, horseradish peroxidase, or tyrosinase, and the pH adjusting agent may be sodium hydroxide, lithium hydroxide, potassium hydroxide, rubidium hydroxide, cesium hydroxide, magnesium hydroxide, calcium hydroxide, strontium hydroxide, or barium hydroxide. However, the oxidizing agent and the pH adjusting agent are not limited thereto.

In an embodiment, in a case where the oxidizing agent is added and crosslinking is performed, crosslinking represented by the following Formula 2 is formed between the hyaluronic acid derivatives. In Formula 2, HA' represents hyaluronic acid in which the carboxyl group is substituted with an amide group.

[Formula 2]

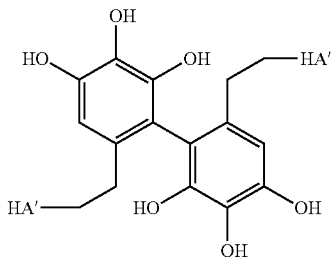

In another embodiment, in a case where the pH adjusting agent is added and crosslinking is performed, crosslinking represented by the following Formula 3 is formed between the hyaluronic acid derivatives. In Formula 3, HA' represents hyaluronic acid in which the carboxyl group is substituted with an amide group.

[Formula 3]

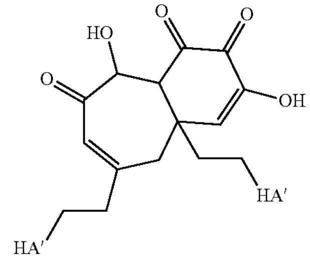

In an embodiment of the present invention, in the step of crosslinking hyaluronic acid derivatives, each of which is modified with a gallol group, a hyaluronic acid hydrogel was respectively prepared by using sodium periodate, which is an oxidizing agent, or sodium hydroxide, which is a pH adjusting agent (see Preparation Example 2). As a result, it was possible to identify that the hyaluronic acid hydrogels prepared according to the respective crosslinking methods exhibit remarkable differences in physical properties such as crosslinking rate, rigidity, elasticity, adhesive strength, and degradation pattern, together with excellent biocompatibility (see Examples 1 to 3).

In an embodiment of the present invention, there is provided a filler composition comprising the hyaluronic acid derivative or hyaluronic acid hydrogel of the present invention. The filler composition of the present invention is provided in a liquid or solution state in which hyaluronic acid derivatives into each of which a gallol group has been introduced are mixed in an aqueous medium. In particular, in a case of being injected into the body, such a solution, although not containing a crosslinking component, can form a hydrogel only with oxidizing power in the body without interpersonal deviation, thereby serving to replenish skin tissue and to retain moisture in the skin. In an embodiment, the aqueous medium is a phosphate buffered saline (PBS), and the hyaluronic acid derivative may be contained in an amount of preferably 0.1% (w/v) to 20.0% (w/v), and more preferably 0.3% (w/v) to 10.0% (w/v), with respect to the entire filler composition. However, various modifications or alterations may be made depending on aqueous media and content ratios in a filler composition which are well known in the art.

The term "filler" as used here means an injectable material that replenishes skin tissue, such as by injecting a biocompatible material into or under the skin to improve wrinkles and restore cosmetic volume. At present, as materials for preparing fillers which have been approved by FDA or MFDS, collagen, hyaluronic acid, calcium hydroxyapatite, polylactic acid, and the like are mentioned. Among these, hyaluronic acid is a material similar to a human body constituent and can be used without skin reaction test; and hyaluronic acid has a characteristic of attracting 214 water molecules per molecule, thereby effectively retaining moisture in the skin. Thus, hyaluronic acid currently accounts for about 90% of the filler market. Due to use of a hyaluronic acid derivative into which a gallol group having high oxidizing power has been introduced, the filler composition according to the present invention can form a hydrogel only with oxidizing power in the body without addition of a crosslinking agent so that biocompatibility is enhanced, and the above-mentioned hydrogel formed in the body can maintain its shape in a transparent state for a long period of time (at least 6 months). Thus, the filler composition has technical significance in that it shows an excellent wrinkle-improving effect according to the characteristics of hyaluronic acid as described above, has excellent adhesive strength and stability in the body as compared with conventional filler products, and can be stably injected into a target site regardless of extrusion force (Examples 2 and 3).

In addition, the filler composition of the present invention may be formulated into a powder form, and more specifically into a freeze-dried powder form, to provide ease of use and storage stability. On the other hand, the above-mentioned filler composition requires a pretreatment step in which it is dissolved in an aqueous medium such as PBS and solubilized before being injected into the skin. However, it is also possible to directly apply a filler composition, which has been made into a solution, depending on storage and formulation conditions thereof.

In another embodiment, in order to impart an effective skin-regenerating effect, the filler composition of the present invention may further comprise a cell growth factor or a vitamin. The cell growth factor collectively refers to a polypeptide that facilitates cell division, growth, and differentiation, and may be preferably selected from the group consisting of fibroblast growth factor (FGF), epithelial cell growth factor (EGF), keratinocyte growth factor (KGF), transforming growth factor alpha (TGF-α), transforming growth factor beta (TGF-β), granulocyte colony stimulating factor (GCSF), insulin-like growth factor (IGF), vascular endothelial growth factor (VEGF), hepatocyte growth factor (HGF), platelet-derived growth factor-BB (PDGF-BB), brain-derived neurotrophic factor (BDNF), and glial cell-derived neurotrophic factor (GDNF). The cell growth factor may be contained in an amount of 20 ng/ml to 20 μg/ml, but is not limited thereto.

In yet another embodiment, the filler composition of the present invention may further comprise a local anesthetic to alleviate pain during an injection process. The local anesthetic may be selected from the group consisting of ambucaine, amolanone, amylocaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethicaine, dibucaine, dimethisoquine, dimethocaine, diferodone, dycyclonine, ecgonidine, ecgonine, ethyl chloride, etidocaine, beta-eucaine, euprocine, fenalcomine, fomocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, bupivacaine, salicyl alcohol, tetracaine, tolycaine, trimecaine, zolamine, and salts thereof The anesthetic may be contained in an amount of preferably 0.1% by weight to 5.0% by weight, and more preferably 0.2% by weight 1.0% by weight, with respect to a weight of the entire filler composition, but the amount is not limited thereto.

In another embodiment, the filler composition of the present invention may further comprise an antioxidant in order to prevent oxidation and degradation of a hydrogel produced by being gelated in the body. The antioxidant may be selected from the group consisting of polyol, mannitol, and sorbitol. The antioxidant may be contained in an amount of preferably 0.1% by weight to 5.0% by weight, and more preferably 0.2% by weight 1.0% by weight, with respect to a weight of the entire filler composition, but the amount is not limited thereto.

In an aspect of the present invention, the present invention provides a method for preparing a filler composition, comprising a step of introducing a gallol group into a skeleton of glucuronic acid in hyaluronic acid, to prepare a hyaluronic acid derivative; and a step of adding the hyaluronic acid derivative to an aqueous medium and performing mixing.

In the present invention, the step of adding the hyaluronic acid derivative to an aqueous medium and performing mixing may be performed preferably in a state in which contact with oxygen and other oxidizing sources is blocked (for example, by injection of nitrogen gas) under a condition at about 4° C. to 28° C. and/or at a pH of 4 to 8, in order to prevent gelation, before injection, of the filler composition which is in a liquid state.

In an embodiment, the aqueous medium is a phosphate buffered saline (PBS), and the hyaluronic acid derivative may be the above Formula 1 produced by a reaction between hyaluronic acid and 5'-hydroxydopamine. The filler composition of the present invention may be prepared by adding the afore-mentioned cell growth factor, local anesthetic, antioxidant, vitamin, and combinations thereof.

In another aspect of the present invention, there is provided a method for improving skin wrinkles, comprising a step of injecting the filler composition into or under the skin of an individual. In the present invention, a target site to which the filler composition is applied may be any site of the body such as the individual's face, neck, ear, chest, hips, arms, and hands, and may preferably be any one site which is a wrinkled region in the skin and is selected from the group consisting of a tear trough region, a glabellar frown line region, an eye-rim region, a forehead region, a nasal bridge region, a nasolabial line region, a marionette line region, and a neck wrinkle region. However, the site is not limited thereto. In addition, in the present invention, the term "individual" means a subject requiring improvement of skin wrinkles, and more specifically includes all of humans, non-human primates, and the like.

In particular, the filler composition of the present invention can be easily injected into a target site regardless of extrusion force. In the injecting step, the filler composition can be injected into or under the skin by using needles or cannulas of various sizes. As a method of injecting the filler, for example, a serial puncture method in which multiple injections are made at a small amount each; a linear threading method in which a needle is caused to go forward by about 10 mm, and then injections are made at a small amount each while being withdrawn backward; a fanning method in which a needle is once inserted, and then the linear threading method is repeatedly performed in the same manner with slightly twisted angles without removing the inserted needle; and the like may be used.

In yet another aspect of the present invention, there is provided a hyaluronic acid hydrogel prepared by crosslinking hyaluronic acid derivatives, each of which is represented by the above Formula 1, in which crosslinking represented by the above Formula 2 is formed between the hyaluronic acid derivatives; and a drug delivery carrier, a drug delivery system, or a scaffold for tissue engineering, comprising the hyaluronic acid hydrogel.

In addition, in still yet another aspect of the present invention, there is provided a hyaluronic acid hydrogel prepared by crosslinking hyaluronic acid derivatives, each of which is represented by the above Formula 1, in which crosslinking represented by the above Formula 3 is formed between the hyaluronic acid derivatives; and a drug delivery carrier, a drug delivery system, or a scaffold for tissue engineering, comprising the hyaluronic acid hydrogel.

The hyaluronic acid hydrogel of the present invention can be used as an artificial extracellular matrix which is an effective skeleton for drug delivery, and has technical significance in that a nano- or micro-unit microparticle form thereof can be implemented due to superior oxidizing ability of the hyaluronic acid derivative modified with a gallol group. The drug is not particularly limited, and may preferably include, but is not limited to, a chemical substance, a small molecule, a peptide, an antibody, an antibody fragment, a nucleic acid including DNA, RNA, or siRNA, a protein, a gene, a virus, a bacterium, an antibacterial agent, an antifungal agent, an anticancer agent, an anti-inflammatory agent, a mixture thereof, and the like.

In addition, the hyaluronic acid hydrogel of the present invention can be used as a scaffold for tissue engineering based on excellent elasticity and adhesive strength. The tissue engineering means that cells or stem cells isolated from the patient's tissue are cultured in a scaffold to prepare a cell-scaffold complex, and then the prepared cell-scaffold complex is transplanted again into the living body. The hyaluronic acid hydrogel can be implemented with a scaffold similar to a biological tissue, in order to optimize regeneration of biological tissues and organs. Therefore, the hyaluronic acid hydrogel can be used for a gene therapeutic agent or a cell therapeutic agent.

In addition, the hydrogel of the present invention can be also used as cosmetics, and medical materials such as a wound healing agent, a wound covering material, an adhesion barrier, or a dental matrix. However, uses of the hydrogel of the present invention are not limited thereto.

Hereinafter, preferred examples will be described in order to facilitate understanding of the present invention. However, the following examples are provided only for the purpose of easier understanding of the present invention, and the scope of the present invention is not limited by the following examples.

PREPARATION EXAMPLES

Preparation Example 1

Preparation of Hyaluronic Acid Derivative Modified with Gallol Group

Figure 1:
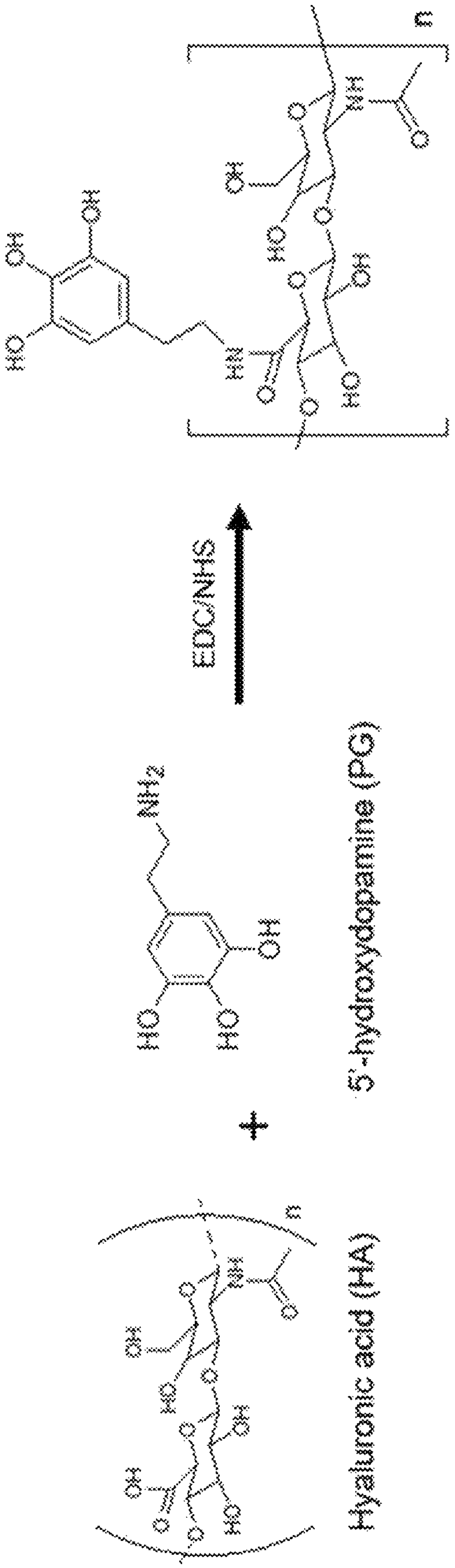
FIG. 1 illustrates a process of synthesizing a hyaluronic acid derivative according to the present invention.
Figure 2A:
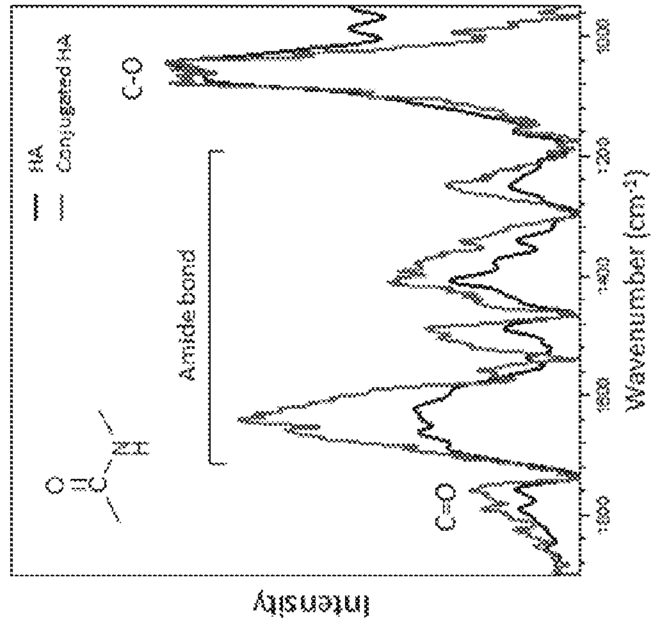
FIGS. 2A and 2B illustrate results obtained by analyzing, with FT-IR (FIG. 2A) or H-NMR (FIG. 2B), a structure of the hyaluronic acid derivative according to the present invention.
Figure 2B:
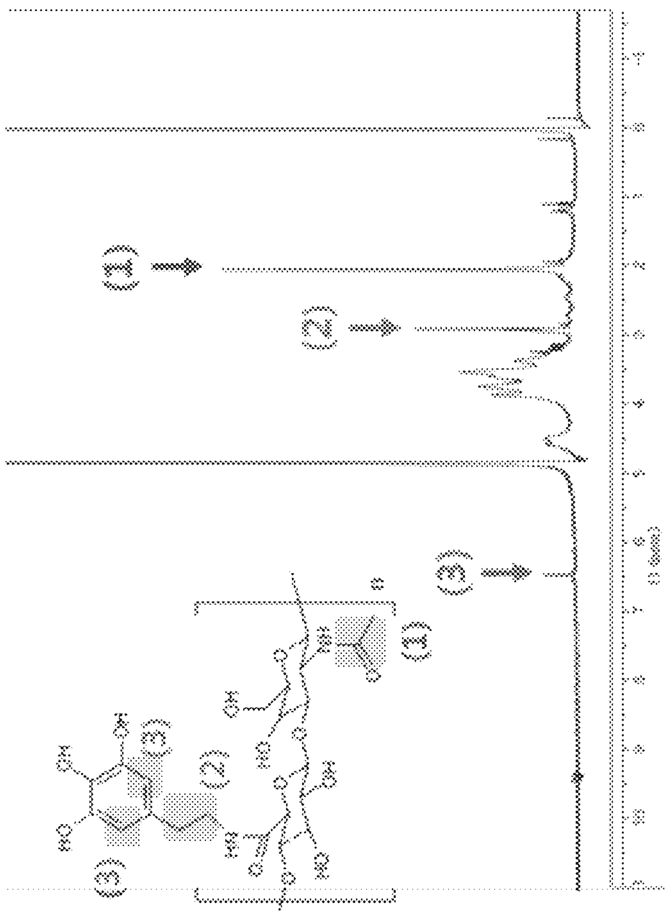

As illustrated in FIG. 1, a hyaluronic acid derivative modified with a gallol group according to the present invention was prepared. Specifically, hyaluronic acid (MW 200K, Lifecore Biomedical, LLC, IL, USA) was completely dissolved in water (TDW), and 1 equivalent of N-hydroxysuccinimide (NHS, Sigma-Aldrich, Inc., St. Louis, Mo., USA) and 1.5 equivalent of 1-(3-dimethylaminopropyl)-3-ehtylcarbodiimide hydrochloride (EDC, Thermo Scientific, Rockford, Ill., USA) were added thereto. After 30 minutes, 1 equivalent of 5'-hydroxydopamine (Sigma-Aldrich, Inc.) was added thereto as a PG moiety and the resultant was allowed to react at pH 4 to 4.5 for 24 hours. Reactants having two different molar ratios were used in the preparation of HA-PG conjugates (HA:EDC:NHS:PG=1:1.5:1:1 or 2:1.5:1:1). Then, EDC, NHS, and 5'-hydroxydopamine were removed by dialysis based on PBS and water (Cellu/Sep (tradename), dialysis membrane (6.8 kDa cut-off, Membrane Filtration Products Inc., Seguin, Tex., USA)), and the solvent was evaporated through freeze-drying to prepare the hyaluronic acid derivative of the present invention. In order to identify synthesis of the hyaluronic acid derivative, analysis was performed with Fourier transform-infrared spectroscopy (FT-IR) (Vertex 70, Bruker, Billerica, Mass., USA) and proton nuclear magnetic resonance (H-NMR) (Bruker 400 MHz, Bruker). As a result, as illustrated in FIG. 2A, it was possible to identify a newly formed amide bond through a strong peak at a wavenumber region of about 1,580 $cm^{-1}$ to 1,700 $cm^{-1}$, and as illustrated in FIG. 2B, it was possible to identify structures of the aromatic benzene ring and $—CH_2CH_2—$ in 5'-hydroxydopamine, through peaks in the vicinity of 6.5 ppm and 3 ppm, respectively. From the above results, it was found that 5'-hydroxydopamine is introduced into the hyaluronic acid derivative of the present invention due to an amide bond formed between the carboxyl group of hyaluronic acid and the amine group of 5'-hydroxydopamine. In order to calculate a degree of substitution of gallol group with respect to the HA skeleton, the HA-PG conjugate was dissolved in PBS (pH 5) at 1 mg/ml and absorbance of the solution was measured at 283 nm (UV-visible spectrophotometer) (Cary 100 UV-vis, Varian Inc., Palo Alto, Calif., USA)). Percentage of carboxy groups substituted with PG in the HA was calculated using a standard curve obtained through serial dilution of a 5-hydroxydopamine solution (from 1 mg/mL concentration).

Preparation Example 2

Preparation of Hyaluronic Acid Hydrogel

Figure 3:
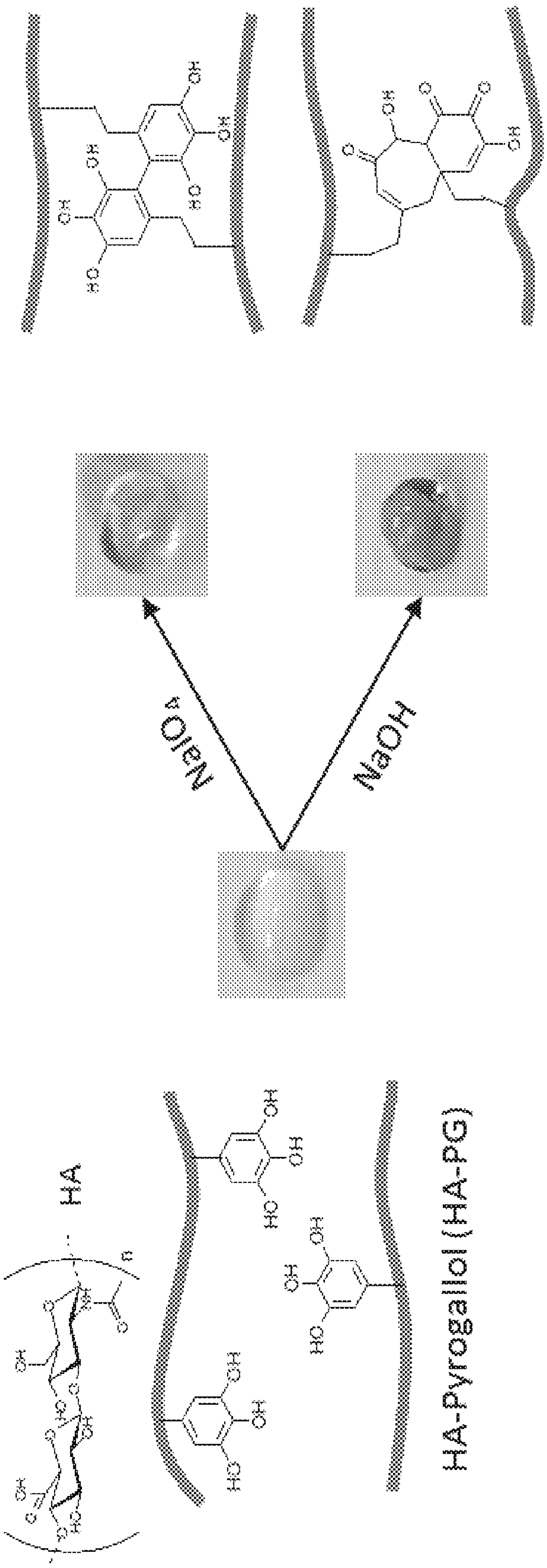
FIG. 3 illustrates schematic views showing appearances of hyaluronic acid hydrogels and changes in crosslinking thereof, depending on different crosslinking methods.

The hyaluronic acid derivatives of Preparation Example 1 were crosslinked to prepare a hyaluronic acid hydrogel, in which each crosslinking method using sodium periodate ($NaIO_4$) as an oxidizing agent or sodium hydroxide (NaOH) as a pH adjusting agent (pH 8 to 9) was employed. Specifically, the hyaluronic acid derivatives were dissolved in PBS (1% (w/v), 2% (w/v)), and then crosslinking was allowed to proceed while performing mixing with 4.5 mg/ml of $NaIO_4$ or 0.08 M NaOH at a volumetric ratio of 1.5:1 to 4:1 relative to the hyaluronic acid derivative solution. As illustrated in FIG. 3, through each of these crosslinking methods, a light brown-colored hyaluronic acid hydrogel or a blue-colored hyaluronic acid hydrogel was prepared.

Figure 4A:
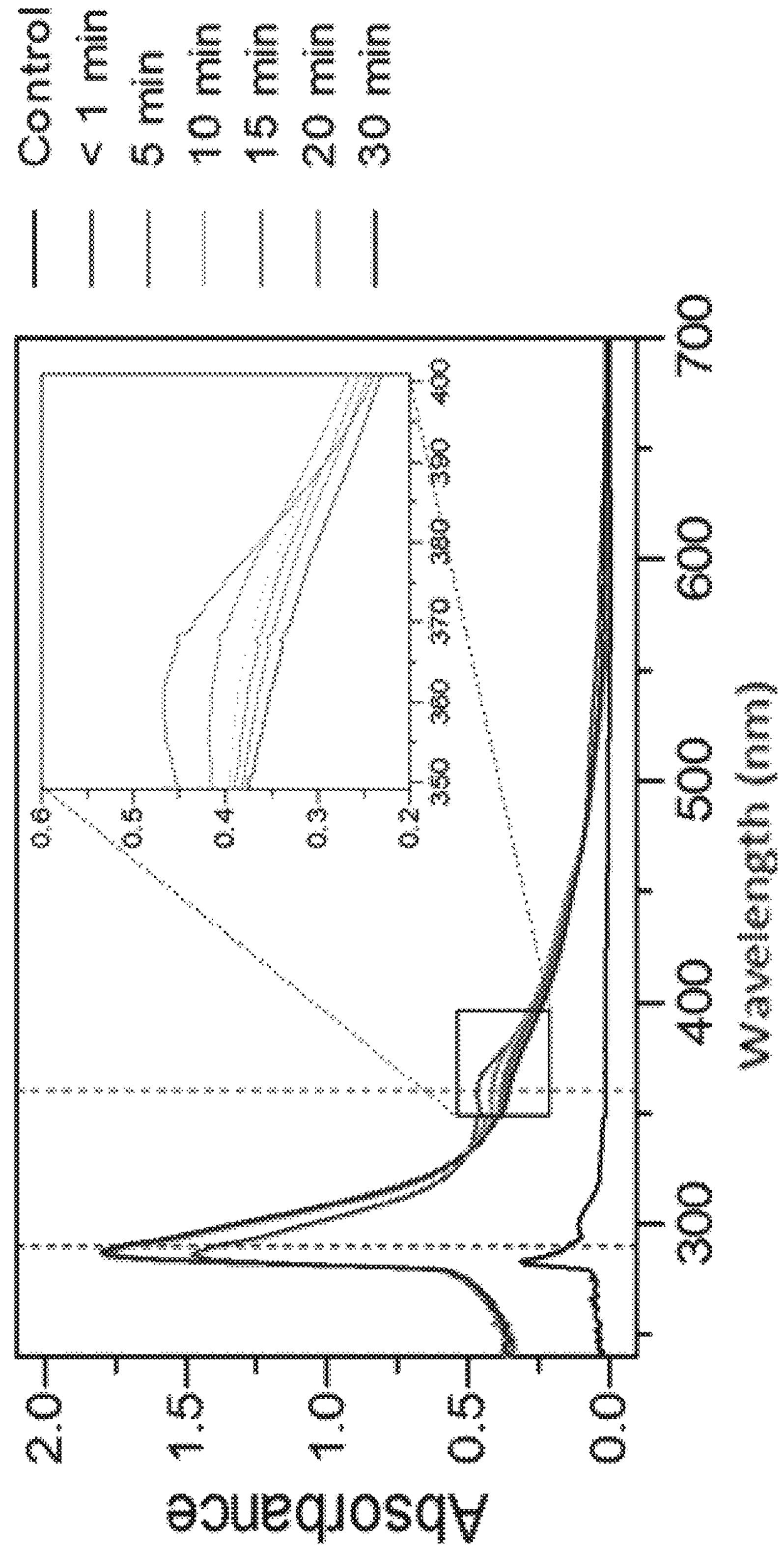
FIG. 4A illustrates a result obtained by analyzing, with UV-vis, changes in chemical structure which occur in the process of preparing a hyaluronic acid hydrogel using $NaIO_4$.
Figure 4B:
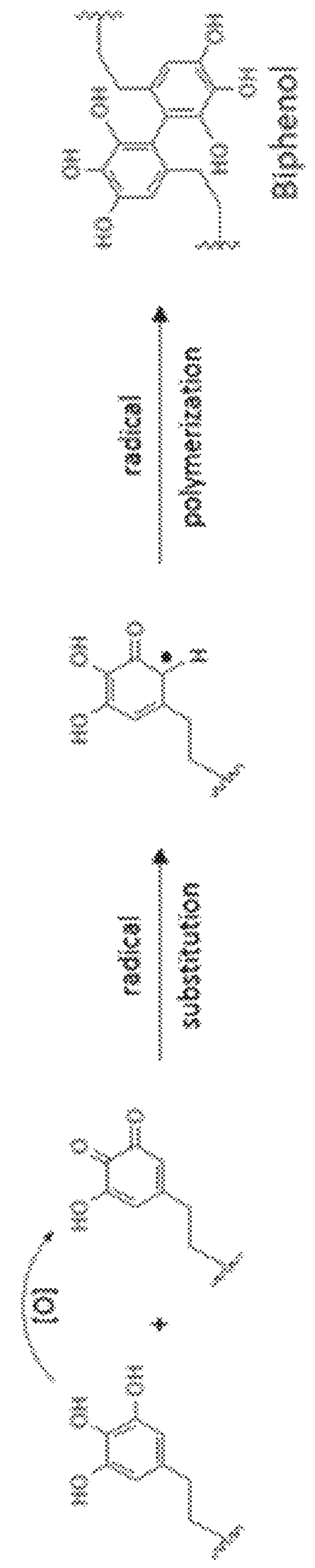
FIG. 4B illustrates a crosslinking mechanism based on the result of FIG. 4A.
Figure 5A:
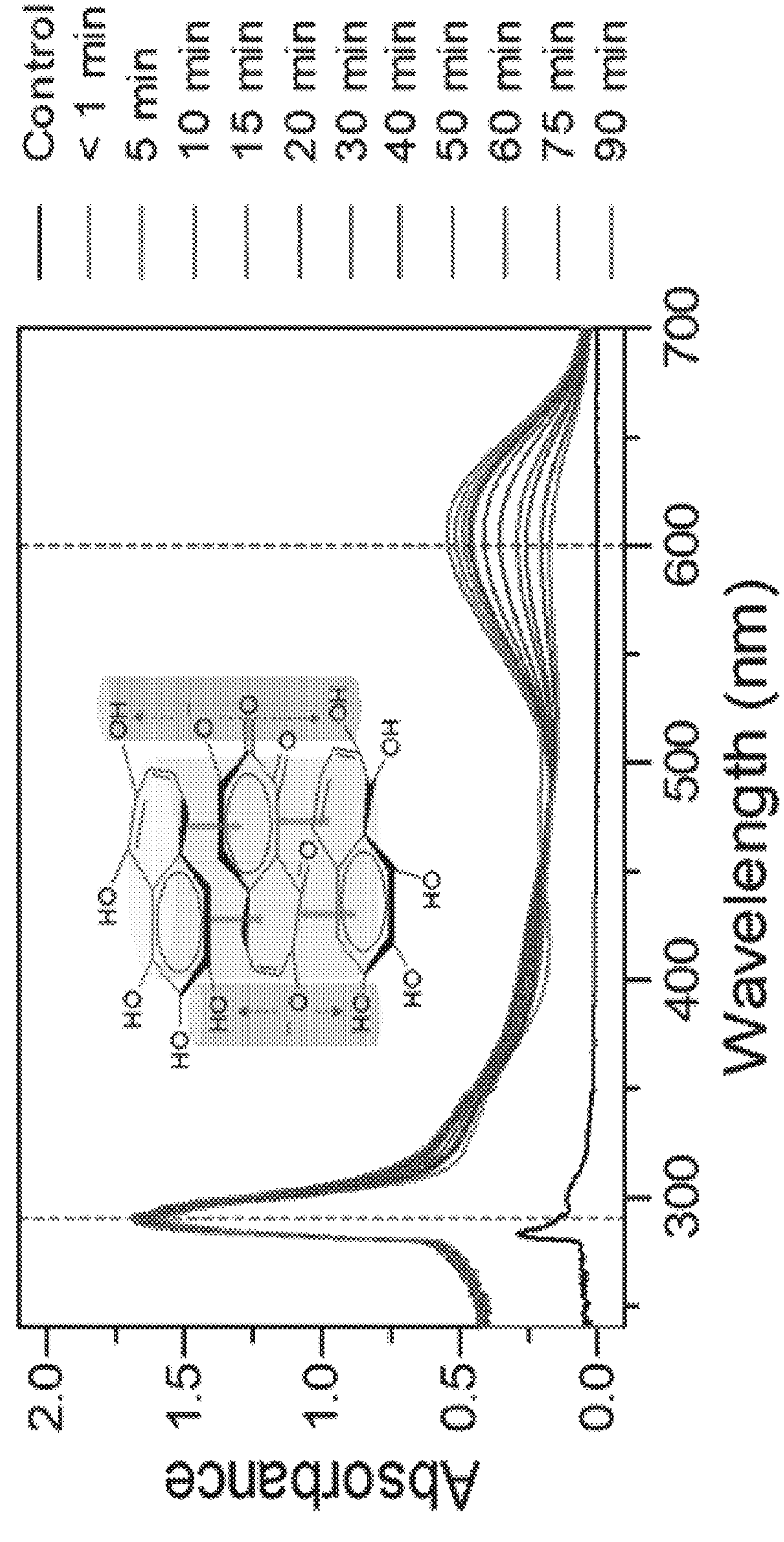
FIG. 5A illustrates a result obtained by analyzing, with UV-vis, changes in chemical structure which occur in the process of preparing a hyaluronic acid hydrogel using NaOH.
Figure 5B:
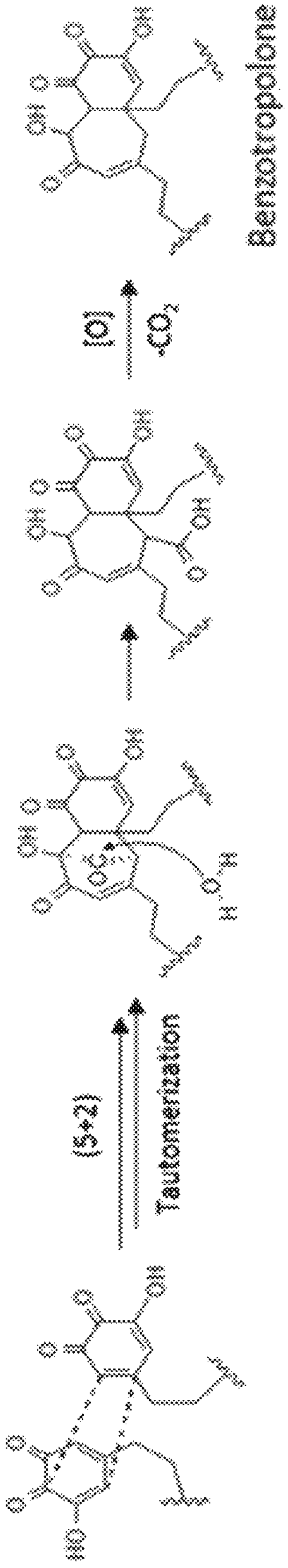
FIG. 5B illustrates a crosslinking mechanism based on the result of FIG. 5A.

In order to specifically identify crosslinking of the hyaluronic acid hydrogel, analysis with ultraviolet-visible spectroscopy (UV-vis) was performed. In a case of using $NaIO_4$, as illustrated in FIGS. 4A and 4B, it was possible to identify that a wavelength region of 350 to 400 nm changes over time (FIG. 4A), meaning instantaneous formation and decrease of radicals, which are intermediate products, in an oxidation process; and it was found that biphenol is then formed by radical polymerization (FIG. 4B). In addition, in a case of using NaOH, as illustrated in FIGS. 5A and 5B, it was possible to identify that a wavelength region of 600 nm changes over time (FIG. 5A); from this result, it was found that a charge transfer complex and benzotropolone are formed by [5+2] tautomerization in an oxidation process (FIG. 5B).

EXAMPLES

Example 1

Changes in Physical Properties of Hyaluronic Acid Hydrogel Depending on Crosslinking Method In the present example, changes in physical properties of hyaluronic acid hydrogels, depending on difference in crosslinking method in Preparation Example 2, were compared. On the other hand, in the hydrogel preparation step, a molar concentration ratio of hyaluronic acid to 5'-hydroxydopamine (0.5×(HA:EDC:NHS:5'-hydroxydopamine=2:1.5:1:1), 1×(HA:EDC:NHS:5'-hydroxydopamine=1:1.5:1:1)) could be used to adjust a rate of being substituted with a gallol group to 4% to 5% (0.5×) or 8% to 9% (1×) (not shown), and changes in physical properties of hydrogels depending on a degree of substitution of 5'-hydroxydopamine were also compared. Specifically, hydrogel formation and changes in elastic modulus over time were compared depending on crosslinking methods; and elasticity, adhesive strength, swelling, and degradation patterns depending on the crosslinking method and the degree of substitution of 5'-hydroxydopamine were respectively compared and analyzed.

1-1. Comparison of Formation Rate of Hyaluronic Acid Hydrogel

Figure 6A:
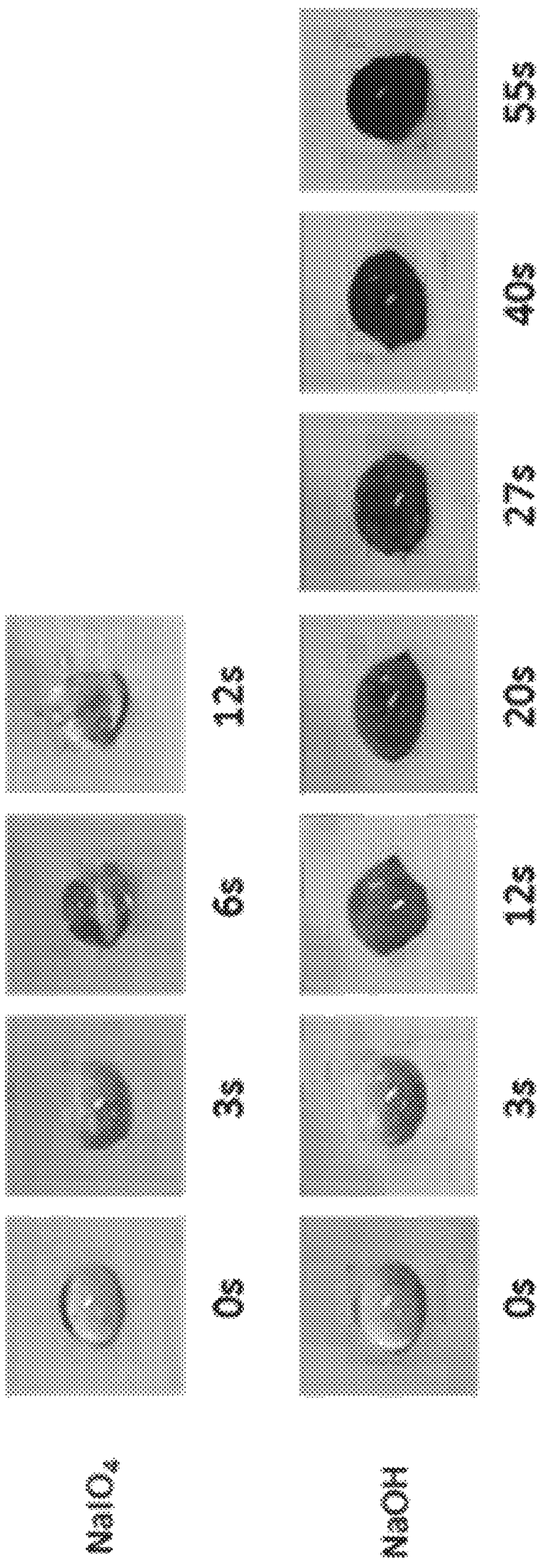
FIGS. 6A and 6B illustrate results obtained by identifying rates at which the hyaluronic acid hydrogels according to the present invention are formed.
Figure 6B:
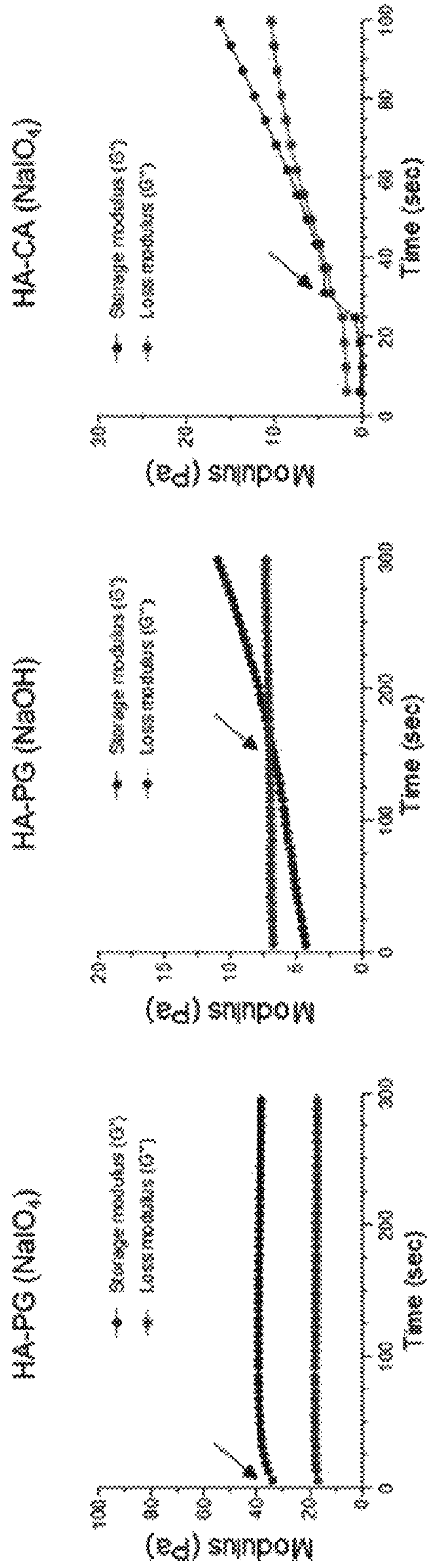

As illustrated in FIG. 6A, it was possible to identify that in a case of using $NaIO_4$, a light brown-colored hydrogel is instantly formed through an immediate crosslinking reaction; on the other hand, in a case of using NaOH, a blue-colored hydrogel is formed relatively slowly. In addition, storage moduli (G') and loss moduli (G") were measured over time, and the measured results were compared with those for the hydrogel (HA-CA($NaIO_4$)) obtained by crosslinking hyaluronic acid derivatives, into each of which a catechol group had been introduced, using $NaIO_4$. As a result, as illustrated in FIG. 6B, all hydrogels were stably formed as the oxidation proceeded (G'>G"). In particular, when a time point at which the hydrogel is formed is identified through a time point at which a storage modulus curve and a loss modulus curve come into contact with each other, it was found that about 2 to 3 minutes is needed in a case of being crosslinked using NaOH, and about 30 seconds is needed for the HA-CA ($NaIO_4$); on the other hand, crosslinking proceeds so quickly that measurement cannot be made, in a case of being crosslinked using $NaIO_4$.

A viscoelastic coefficient of hyaluronic acid was analyzed by measuring storage modulus (G') and loss modulus (G") within a frequency sweep mode in a frequency range of 0.1 to 1 Hz. Elasticity of hyaluronic acid was calculated by dividing a storage coefficient by a loss coefficient at 1 Hz (n=45). Gelation kinetics of the HA-PG were measured with a rheometer (MCR 102, Anton Paar, Va., USA) in a time sweep mode at a controlled strain and frequency of 10% and 1 Hz, respectively. Two oxidizing agents ($NaIO_4$ and NaOH) were added 30 minutes after the initial measurement of GI and G". Adhesiveness of the hydrogel was measured by recording detachment stress of the completely crosslinked hydrogel between a probe and a substrate plate in a rheometer (MCR 102, Anton Paar) (n=3). A pulling speed for the probe was 5 μm/sec.

1-2. Comparison of Elasticity and Adhesive Strength

Figure 7A:
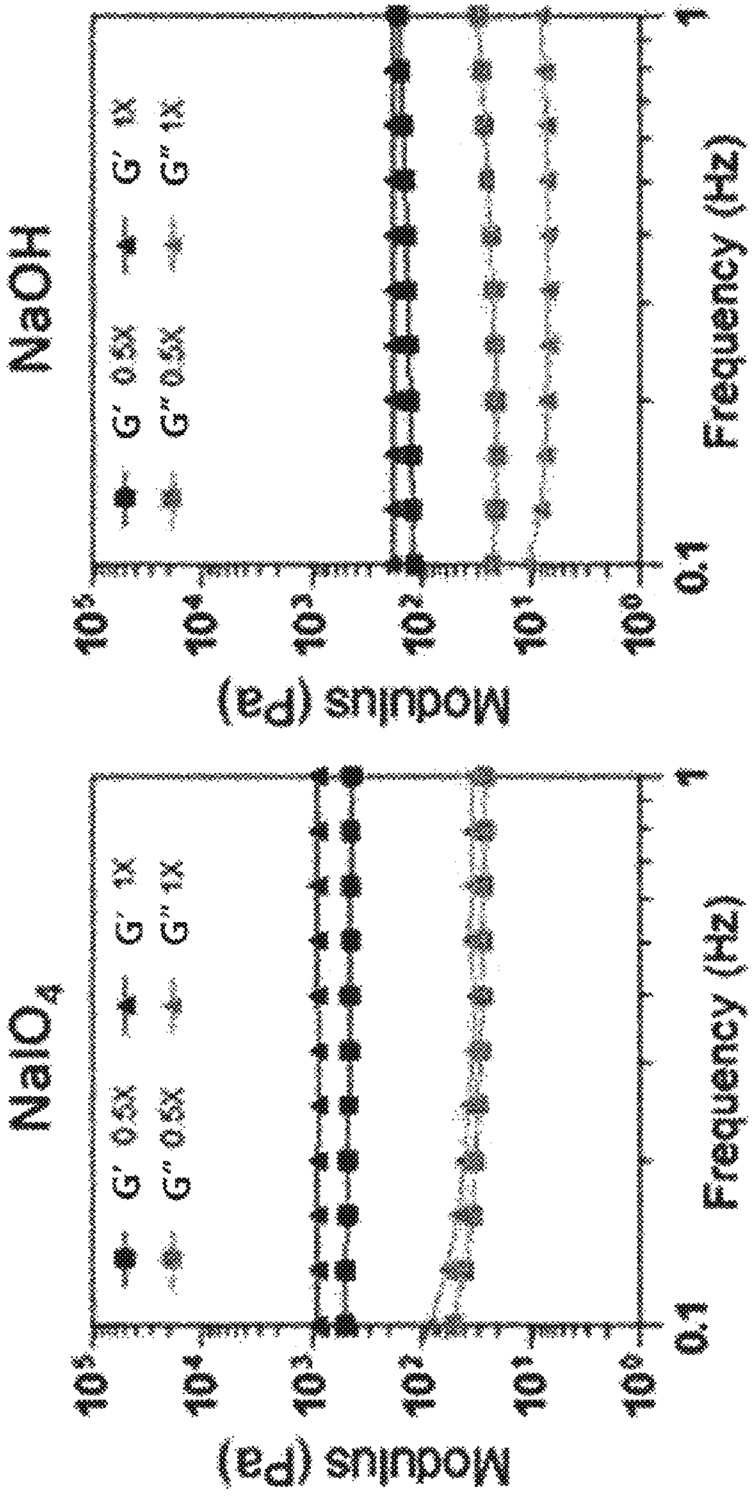
FIGS. 7A and 7B illustrate results obtained by identifying rigidity and elasticity of the hyaluronic acid hydrogels according to the present invention.
Figure 7B:
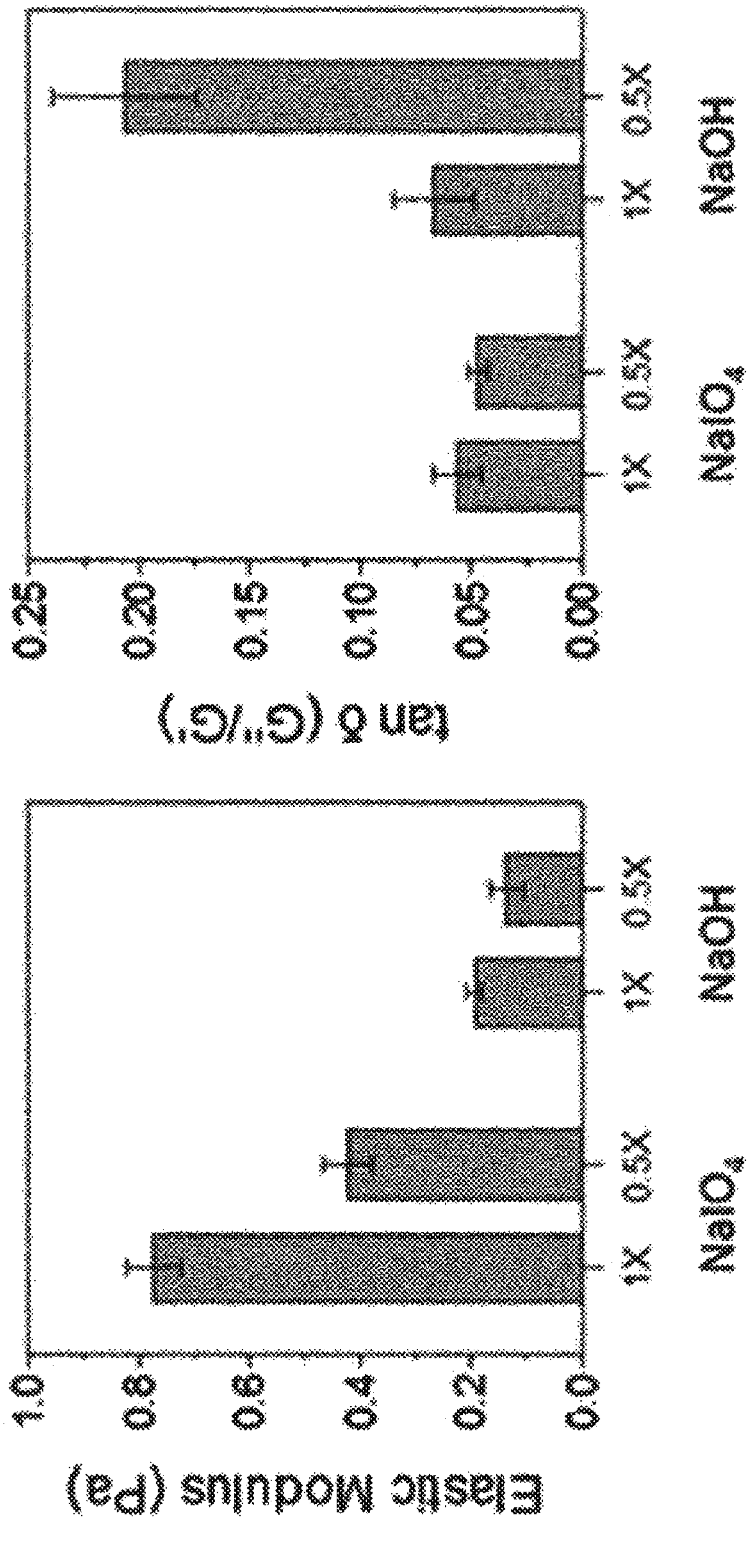
Figure 8A:
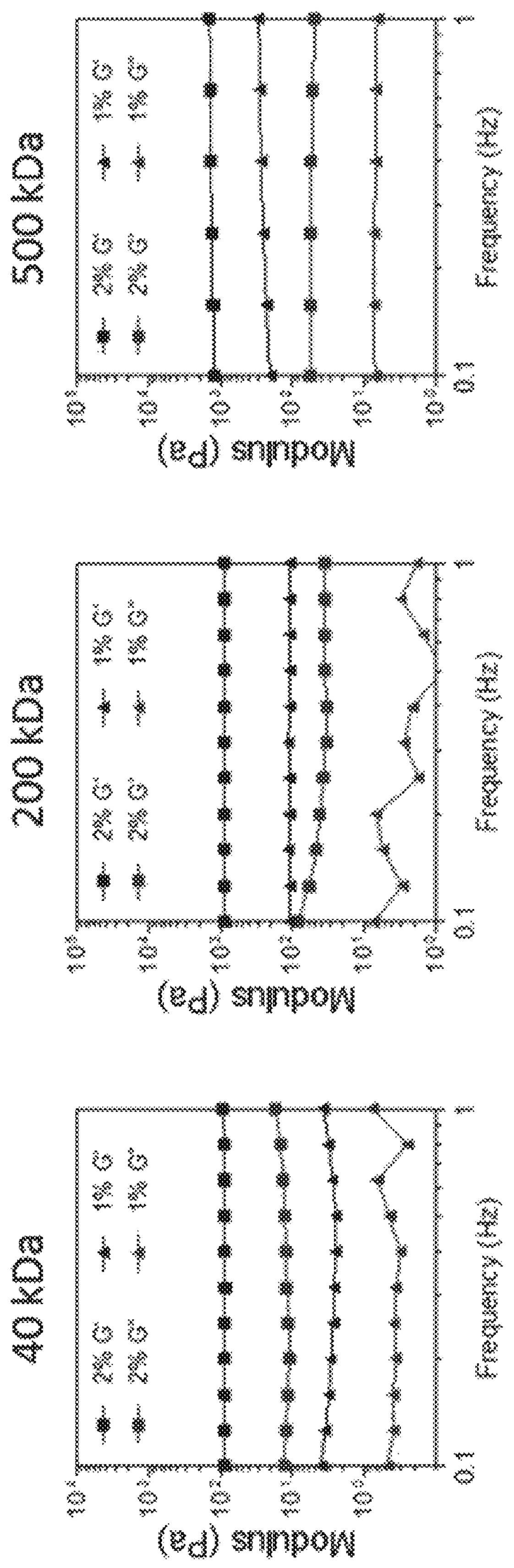
FIGS. 8A and 8B illustrate results obtained by identifying changes in rigidity and elasticity of the $NaIO_4$-crosslinked hyaluronic acid hydrogels depending on molecular weights and concentrations of hyaluronic acid derivatives.
Figure 8B:
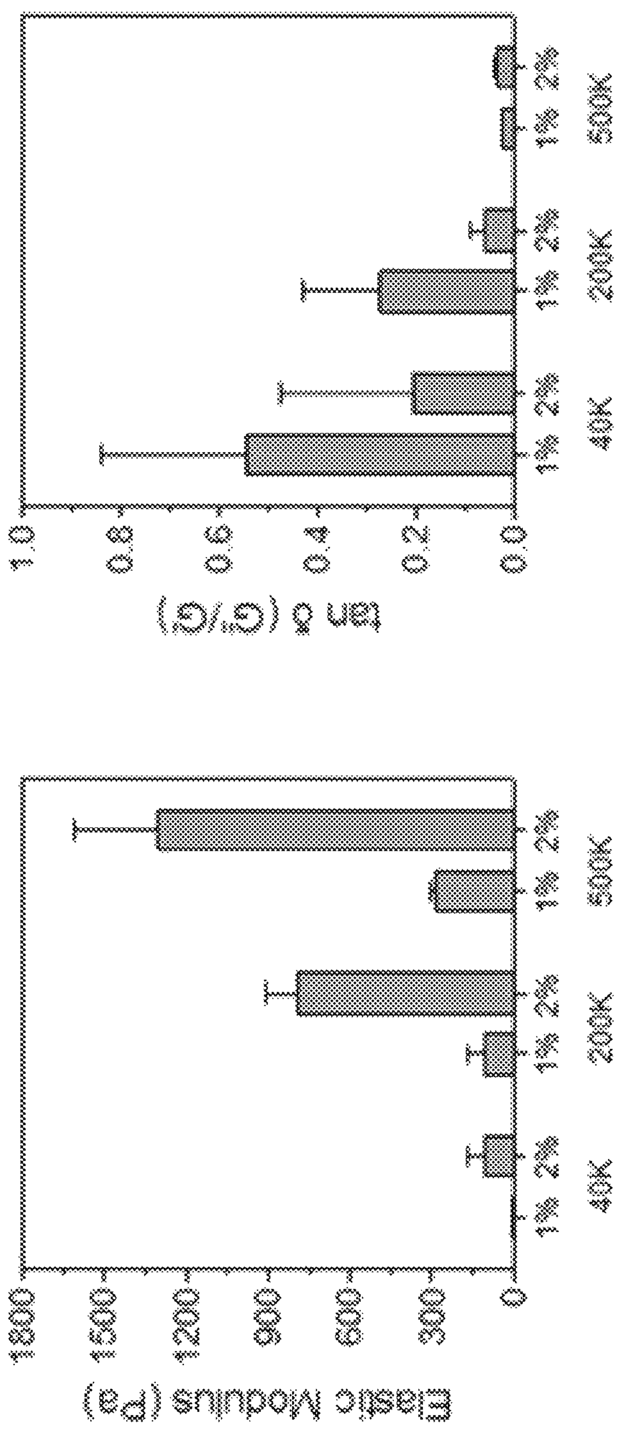
Figure 9A:
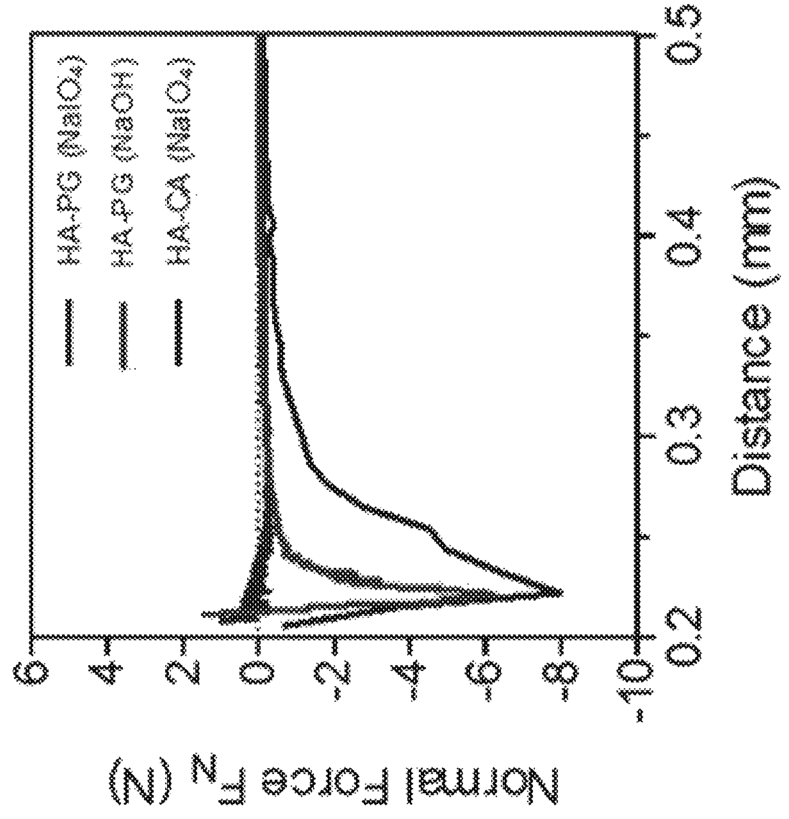
FIGS. 9A and 9B illustrate results obtained by identifying adhesive strength of the hyaluronic acid hydrogels according to the present invention.
Figure 9B:
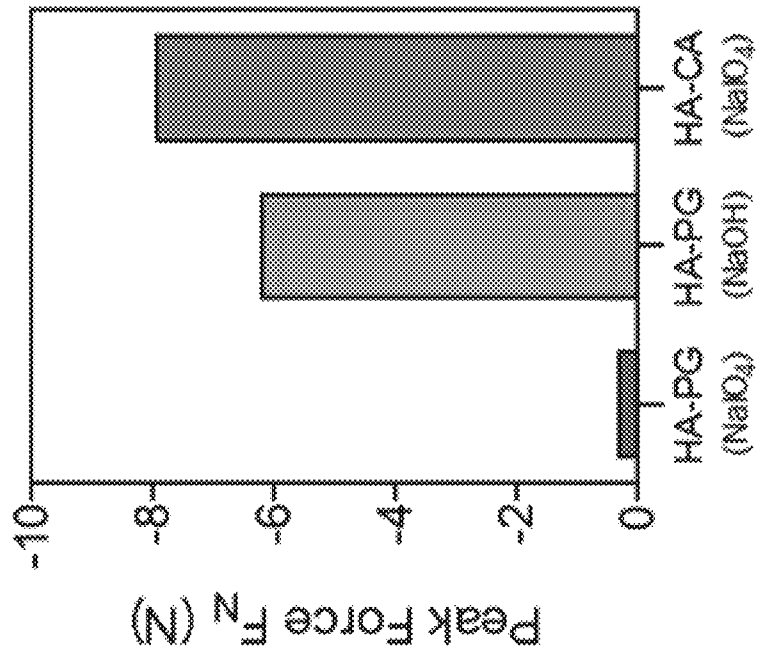

As illustrated in FIG. 7A, despite differences in the crosslinking method or the degree of substitution of 5'-hydroxydopamine, in all cases, storage modulus (G') was measured to be higher at a certain level than loss modulus (G"), which made it possible to identify that the hydrogels were stably formed. In addition, elastic modulus representing rigidity of hydrogel and tan S (G"/G') representing a degree of elasticity were calculated. As a result, as illustrated in FIG. 7B, in a case of using $NaIO_4$, better rigidity of hydrogel was exhibited and all hydrogels had excellent elastic force even at low substitution rates; on the other hand, in a case of using NaOH, better elastic force was obtained as the substitution rate increased. In addition, it was found that in a case of the same crosslinking method, these respective excellent physical properties are also improved as a substitution rate of 5'-hydroxydopamine increases (0.5× <1×). In addition, based on the above results, differences in physical properties of the hydrogels crosslinked with $NaIO_4$, depending on molecular weights (40, 200, 500 kDa) and concentrations (1% (w/v), 2% (w/v)) of the hyaluronic acid derivatives, were identified. As a result, as illustrated in FIGS. 8A and 8B, in all cases, the storage modulus (G') was measured to be higher at a certain level than the loss modulus (G"), which made it possible to identify that the hydrogels were stably formed (FIG. 8A); and it was found that the hydrogel exhibits further improved rigidity and elastic force as hyaluronic acid has an increased molecular weight and has a higher concentration (FIG. 8B). In addition, in order to evaluate adhesive strength of the hydrogels, each of the hydrogels was bridged between respective plates of a rheological instrument (Bohlin Advanced Rheometer, Malvern Instruments, Worcestershire, UK) and force applied to the instrument was measured while increasing spacing between the plates. The above results were compared with those for the hydrogel (HA-CA($NaIO_4$)) obtained by crosslinking hyaluronic acid derivatives, into each of which a catechol group had been introduced, using $NaIO_4$. As a result, as illustrated in FIGS. 9A and 9B, the hydrogel formed by using NaOH and the HA-CA ($NaIO_4$) exhibited superior adhesive strength, whereas almost no adhesive strength was observed in the hydrogel formed by using $NaIO_4$.

1-3. Comparison of Swelling and Degradation Patterns

Figure 10A:
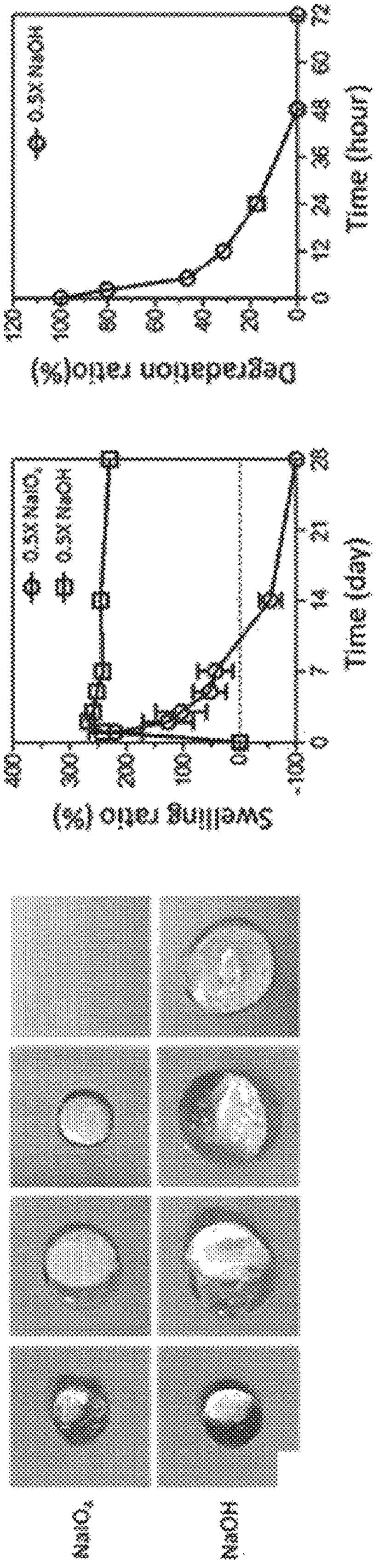
FIGS. 10A and 10B illustrate results obtained by identifying swelling and degradation patterns of the hyaluronic acid hydrogels according to the present invention, and such results were obtained by quantifying and evaluating swelling ratio and degradation ratio of the hyaluronic acid hydrogels prepared by using hyaluronic acid derivatives which have been synthesized by adding 0.5× (FIG. 10A) or 1.0× (FIG. 10B) of 5-hydroxydopamine relative to a molar concentration of hyaluronic acid.
Figure 10B:
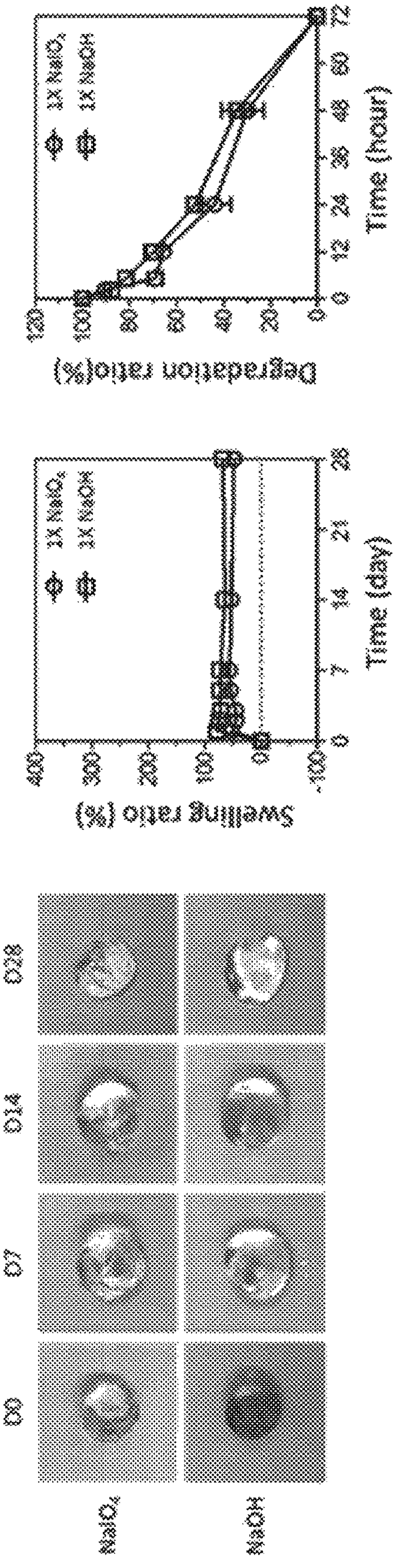

As illustrated in FIGS. 10A and 10B, slightly different swelling and degradation patterns were exhibited depending on the crosslinking method and the degree of substitution of 5'-hydroxydopamine. Swelling characteristics were evaluated by measuring a weight of the remaining hydrogel at specific time points (days 0, 1, 2, 3, 5, 7, 14, and 28). Specifically, the HA-PG was incubated at 37° C. in PBS and a swelling rate was calculated by the following expression: (Wt−Wi)/Wi×100, where Wt is a weight of the hydrogel at each time point, and Wi is a weight of the hydrogel at an initial time point (n=4 to 5). In order to investigate a degradation profile, the HA-PG hydrogel which had been swollen for 3 days was treated with hyaluronidase (5 units/mL, Sigma) and a weight of remaining hyaluronic acid was measured at respective time points (n=4 to 7, 0, 2, 5, 12, 24, 48, and 72 hours). In a case of using $NaIO_4$ rather than NaOH, a low swelling rate was exhibited and degradation proceeded faster. For the same crosslinking method, in a case where a substitution rate of 5'-hydroxydopamine increases, such swelling rate and degradation rate tended to decrease. These results, taken together, indicate that even though hyaluronic acid derivatives having the same structure are used, hydrogels are crosslinked in different bonding forms depending on the crosslinking method (Preparation Example 2), which leads to changes in inherent physical properties such as rigidity, elasticity, adhesive strength, swelling, and degradation. In addition, on the contrary, it was found that even though the same crosslinking method is adopted, the above physical properties were also changed depending on a structure of the hyaluronic acid derivative.

Example 2

Analysis for Cytotoxicity and Biocompatibility

In the present example, cytotoxicity and biocompatibility of the hyaluronic acid hydrogel of Preparation Example 2 were evaluated. First, in order to identify whether the hydrogel causes toxicity and inflammation response in 3D cell culture, human adipose-derived stem cells (hADSCs) ($1.0\times10^6$ cells per 100 μL of hydrogel) were cultured in the hydrogel, and the LIVE/DEAD viability/cytotoxicity kit (Invitrogen, Carlsbad, Calif., USA) was used to perform live/dead staining at respective time points (days 1, 3, and 7) according to the manufacturer's instructions. Stained cells were observed with a confocal microscope (LSM 880, Carl Zeiss, Oberkochen, Germany), and viability was quantified by counting viable and dead cells from a fluorescence image (n=4 to 5). The hADSCs were obtained from ATCC (ATCC, Manassas, Va. USA) and were cultured in the Mesenchymal Stem Cell Basal Medium (ATCC) supplemented with Growth Kit-low serum (ATCC) and 1% penicillin/streptomycin (Invitrogen).

In addition, immune cells (Raw 264.7) were co-cultured in a hydrogel using a Transwell system (permeable supports with 3.0 μm pores, Corning, New York, N.Y., USA), and then an amount of tumor necrosis factor (TNF-α) secreted by inflammation response was measured using enzyme-linked immunosorbent assay (ELISA). Raw 264.7 cells were incubated overnight, and then seeded on a 96-well plate ($2.0\times10^4$ cells per well). Then, 50 μl of hydrogel was loaded through an upper inserting portion of the Transwell, and then additional incubation was performed for 24 hours. An amount of TNF-α in the medium collected from the co-culture was quantitated using a TNF-α enzyme-linked immunosorbent assay (ELISA) kit (R&D Systems, Minneapolis, Minn., USA).

In order to evaluate in vivo biocompatibility of the HA-PG hydrogel, 100 μl of the HA-PG hydrogel (final concentration of 2% [w/v]) formed by using $NaIO_4$ or NaOH was subcutaneously transplanted into ICR mice. Before the transplantation, the mice (5-week-old male, OrientBio, Seongnam, Korea) were anesthetized with ketamine (100 mg/kg, Yuhan, Seoul, Korea) and xylazine (20 mg/kg, Bayer Korea, Ansan, Korea). For tissue analysis, hyaluronic acid structures were recovered with adjacent tissues at predetermined time points (days 0, 7, 14, 28, and 84). The recovered hyaluronic acid was fixed in 4% paraformaldehyde (Sigma) for 2 days, embedded in OCT compound (Leica Biosystems, Wetzlar, Hesse, Germany), and then cut into 6 μm thickness. The cut samples from the in vivo experiment were stained with H&E to evaluate hydrogel maintenance. Toluidine blue staining was performed to investigate an immune response after the transplantation of the HA-PG hydrogel. In vivo degradation of the HA-PG hydrogel was evaluated by measuring a remnant weight of the recovered hydrogel structure at each time point (n=3 to 5).

Figure 11A:
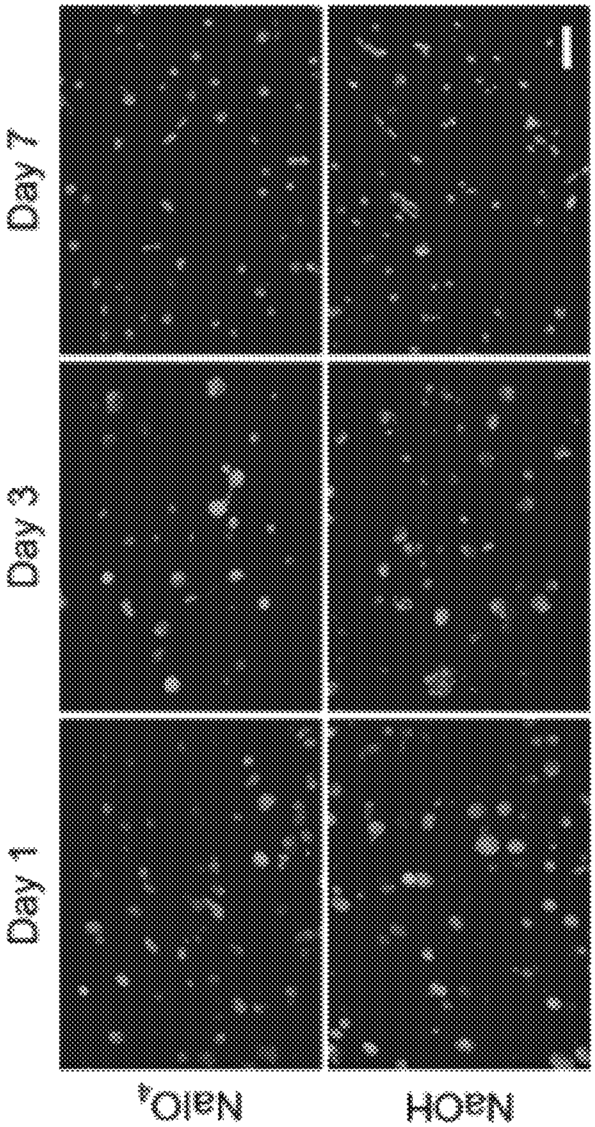
FIGS. 11A, 11B, and 11C illustrate results obtained by identifying whether the hyaluronic acid hydrogels according to the present invention cause cytotoxicity and inflammatory response.
Figure 11B:
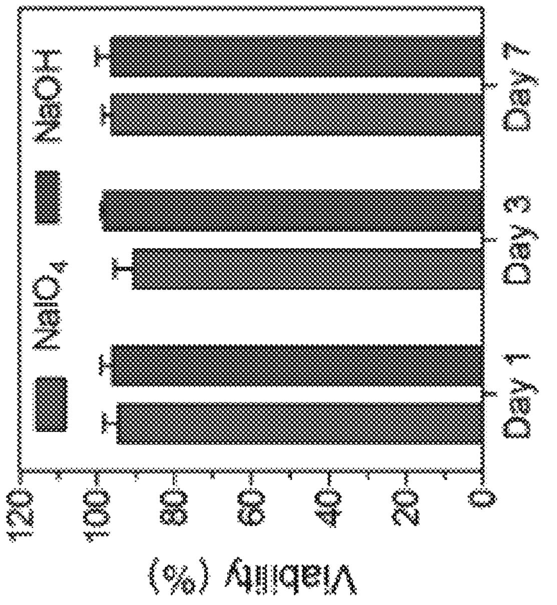
Figure 11C:
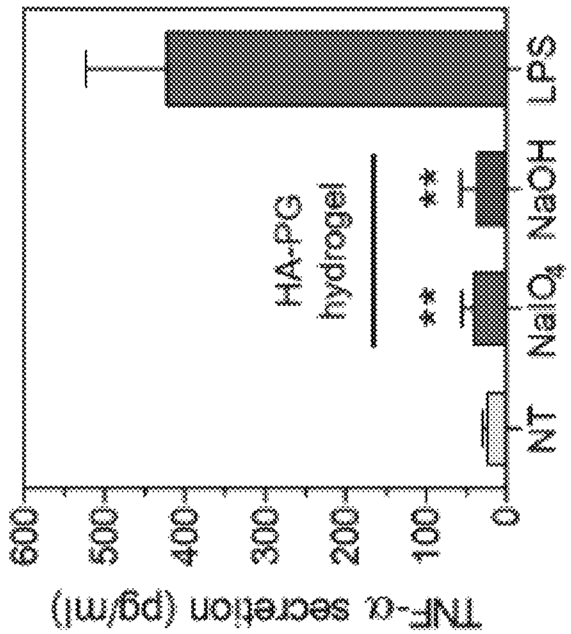
Figure 12A:
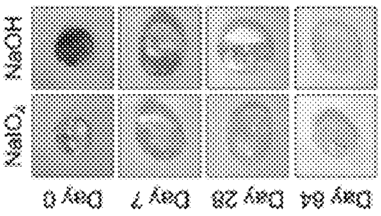
FIGS. 12A, 12B, 12C, and 12D illustrate results obtained by identifying in vivo compatibility of the hyaluronic acid hydrogels according to the present invention.
Figure 12B:
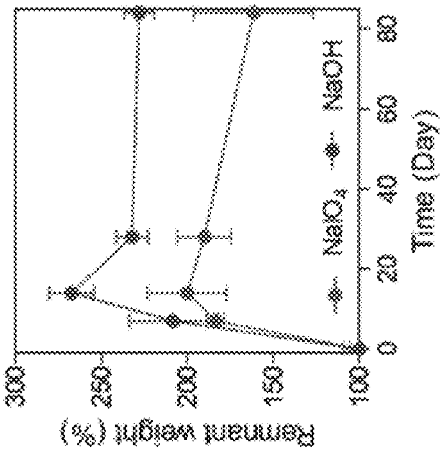
Figure 12C:
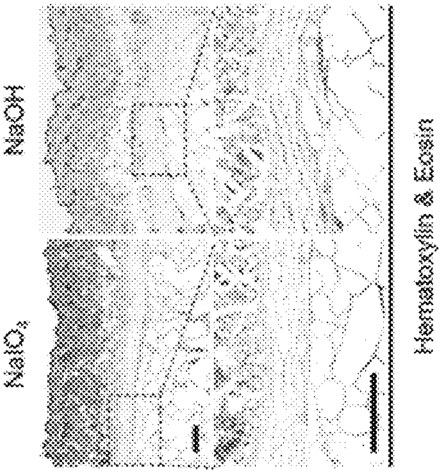
Figure 12D:
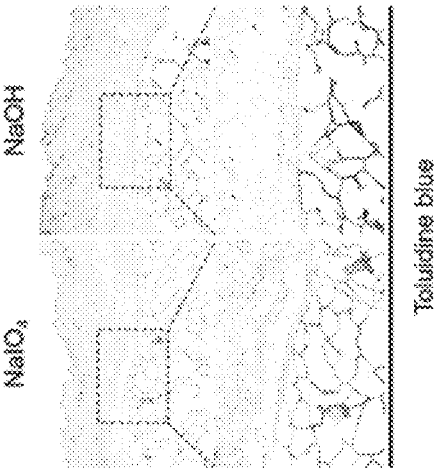

As a result, as illustrated in FIGS. 11A-11C and 12A-12D, neither of the two types of hydrogels depending on the crosslinking method exhibited cytotoxicity up to 7 days after the culture (FIGS. 11A and 11B). TNF-α which had been increased due to LPS was detected only in a small amount in a case where treatment with the above-mentioned two hydrogel forms is performed, and this was not largely different from the control (NT) in which no treatment had been performed (FIG. 11C). In addition, as illustrated in FIGS. 12A-12D, even in a case where the hydrogel is transplanted into mice, specific inflammatory findings were not observed, and it was possible to identify that a structure thereof is well maintained without proliferation of inflammation-related cells such as macrophages in the vicinity of the transplanted hydrogel (FIGS. 12C and 12D).

Example 3

Analysis for Degradation Pattern In Vivo

In the present example, hyaluronic acid hydrogels having a difference in the crosslinking method ($NaIO_4$/NaOH) and the molar ratio (0.5×, 1×) of the reacted 5'-hydroxydopamine was subcutaneously transplanted into mice. On the day of transplantation, and at weeks 1, 4, and 12 after the transplantation, the mice were sacrificed and respective hydrogels were collected. For these hydrogels, a degree of swelling was visually identified, and a remnant amount in vivo was calculated, thereby analyzing degradation pattern in vivo and the like.

Figure 13A:
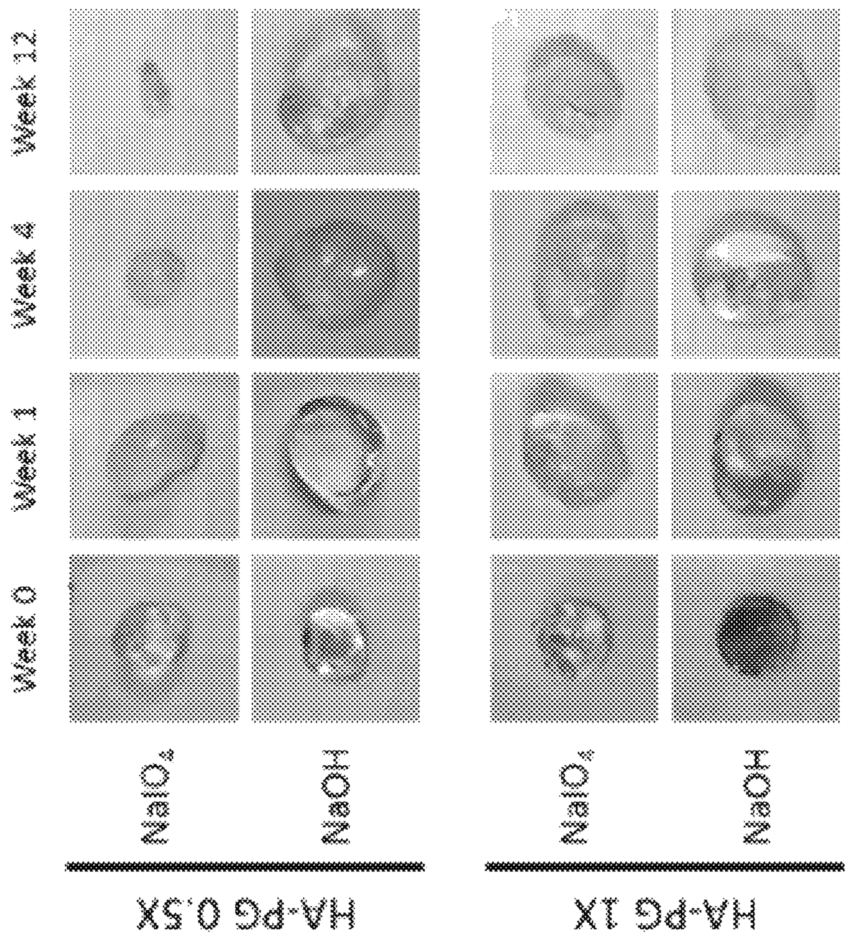
FIGS. 13A and 13B illustrate results obtained by identifying in vivo degradation patterns of the hyaluronic acid hydrogels according to the present invention in vivo.
Figure 13B:
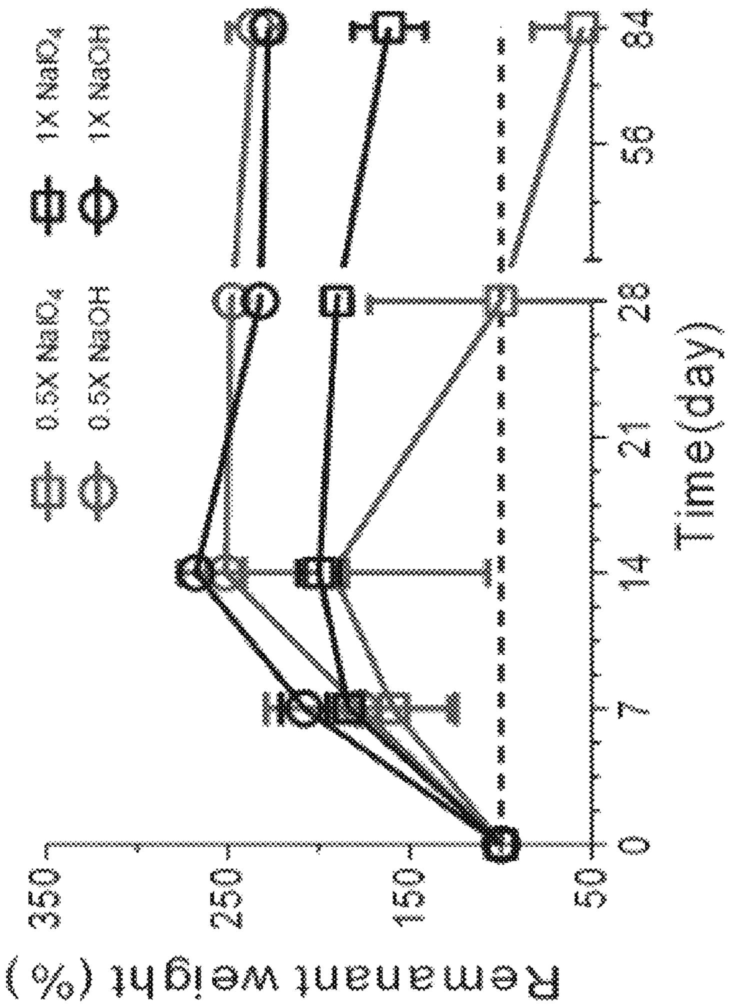

As a result, as illustrated in FIGS. 13A and 13B, it was possible to identify that the hydrogel obtained by performing crosslinking using $NaIO_4$ has a smaller degree of swelling, and it was found that such a hydrogel exhibits a faster degradation in vivo. In addition, for the same crosslinking method, in a case where a substitution rate of 5'-hydroxydopamine (gallol group) increases, a degradation rate tends to decrease.

The results of Examples 2 and 3 suggest that the hyaluronic acid hydrogel according to the present invention can be utilized, for example, in the biomaterial field such as a drug delivery carrier and a scaffold for tissue engineering. In particular, considering the inherent physical properties of Example 1 and the like, the hydrogel formed by using $NaIO_4$ which exhibits rapid crosslinking rate and in vivo degradation pattern can be utilized as a drug delivery carrier in the form of fine particles, and the hydrogel formed by using NaOH which exhibits excellent adhesive strength and a slow in vivo degradation pattern can be utilized as a scaffold for tissue engineering and the like.

Example 4

Figure 14B:
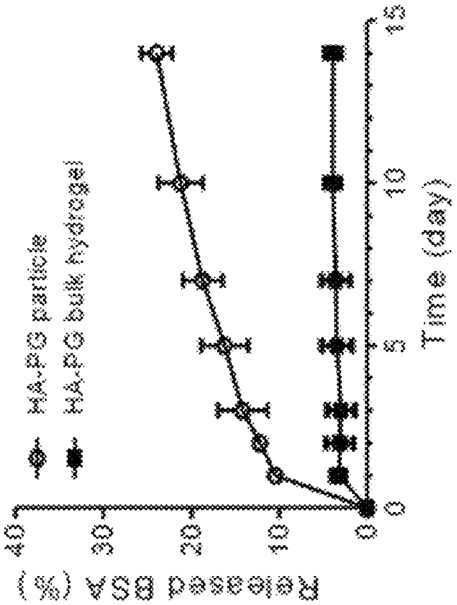
FIGS. 14A and 14B illustrate results obtained by identifying a possibility of utilizing, as a drug delivery preparation, a hydrogel prepared by using $NaIO_4$.
Figure 14A:
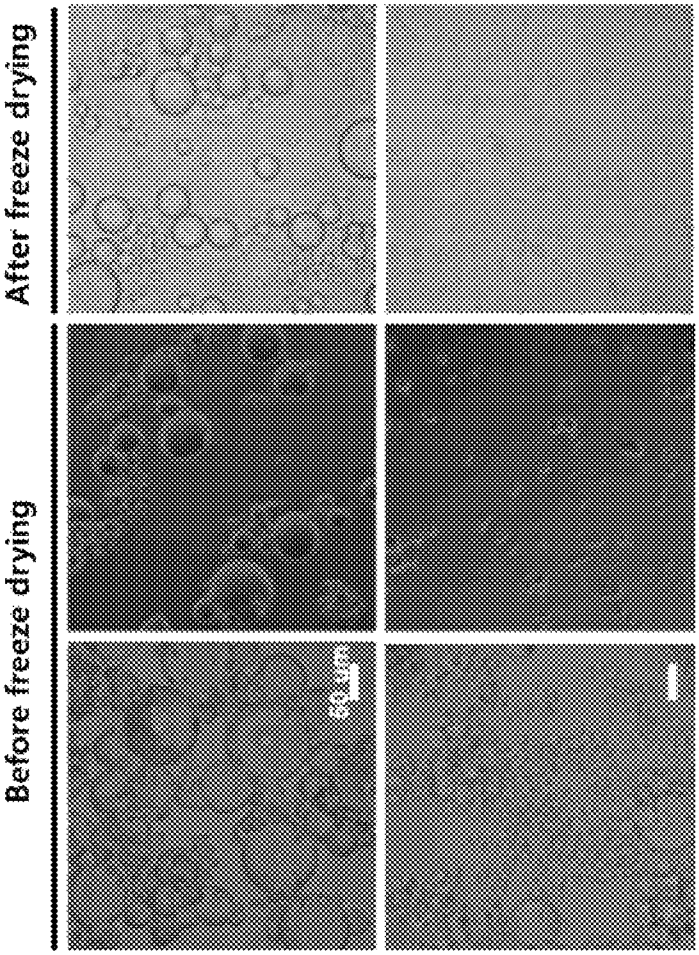

Utilization as Drug Delivery System through Formation of Microparticles 4-1. Sustained Release of Protein Using HA-PG Hydrogel Microparticles In the present example, as an embodiment of the hydrogel formed by using $NaIO_4$, a drug delivery preparation in the form of microparticles having a nano- or micro-unit diameter was prepared and efficacy thereof was identified. First, an oil/water emulsion method was used to induce formation of an emulsion of the hyaluronic acid derivative solution (HA-PG) of Preparation Example 2, and an oxidizing agent ($NaIO_4$) was added to the solution. Then, formation and presence of microparticles were identified before and after freeze-drying. In addition, the HA-PG solution was mixed with a protein (bovine serum albumin, BSA), and the mixture was made into an emulsion form. Then, an oxidizing agent ($NaIO_4$) was added thereto and crosslinking was performed, thereby preparing microparticles in which BSA was encapsulated. A protein release pattern of the microparticles was identified over 14 days. As a result, as illustrated in FIGS. 14A and 14B, microparticles containing, as a component, a hyaluronic acid hydrogel were produced through the above-mentioned preparation process, and were maintained unchanged even after undergoing the freeze-drying process (FIG. 14A). In addition, it was possible to identify that encapsulated proteins are hardly released in an HA-PG bulk hydrogel, whereas proteins are released at a constant rate in the HA-PG particle (FIG. 14B). Thus, the hydrogel formed by using $NaIO_4$ in the form of microparticles can be utilized as a drug delivery preparation.

4-2. Sustained Release of Antibody Using HA-PG Hydrogel Microparticles

Figure 15A:
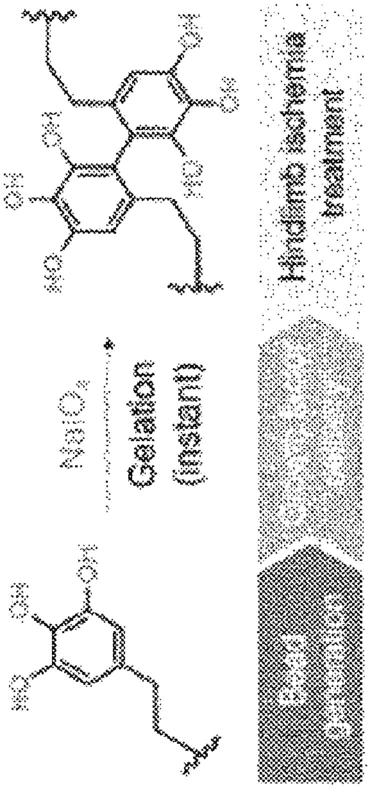
FIGS. 15A, 15B, and 15C illustrate results obtained by identifying a possibility of utilizing, as a drug delivery preparation, a hydrogel prepared by using $NaIO_4$.
Figure 15B:
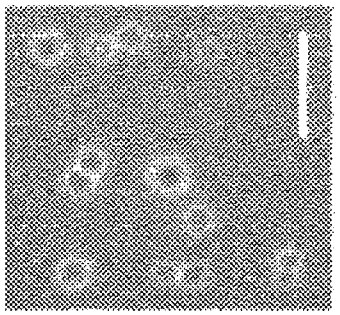
Figure 15C:
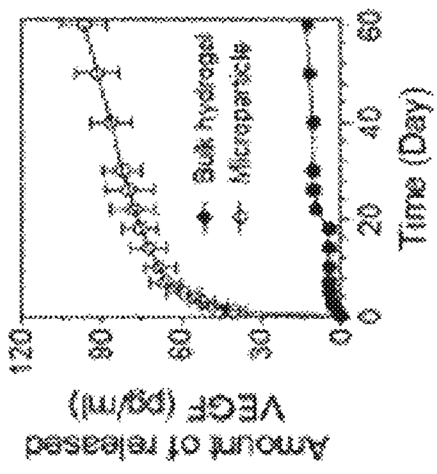

First, as a method for sustained and controlled delivery of growth factors for therapeutic application, HA-PG hydrogel microparticles were prepared by an oil/water emulsion method using ultrafast gel-formation with $NaIO_4$-mediated crosslinking (FIG. 15A). HA-PG microparticles can be prepared by simple addition of the HA-PG solution to a water-in-oil emulsion. Rapid chemical crosslinking of the HA-PG emulsion by $NaIO_4$ in an oil phase resulted in production of a large number of submicron HA particles within a few minutes. The produced HA-PG microparticles exhibited a spherical shape with an average diameter of 8.8 μm (±3.9 μm) (FIG. 15B). Interestingly, vascular endothelial growth factors (VEGFs) encapsulated in the HA-PG microparticles were slowly released for 60 days, whereas VEGFs were hardly released from the hydrogel structure for the bulk HA-PG (FIG. 15C). In a previous study conducted by the present inventors, the present inventors have found that growth factors encapsulated in a catechol-modified alginate hydrogel are hardly released due to strong binding of the proteins to oxidized catechol during a gelation process. Like the catechol group, a PG group may also induce strong binding of the growth factors to the hydrogel structure. However, it appears that due to a remarkably increased surface area of growth factors for release, the HA-PG formed as fine particles can release VEGFs.

Figure 16A:
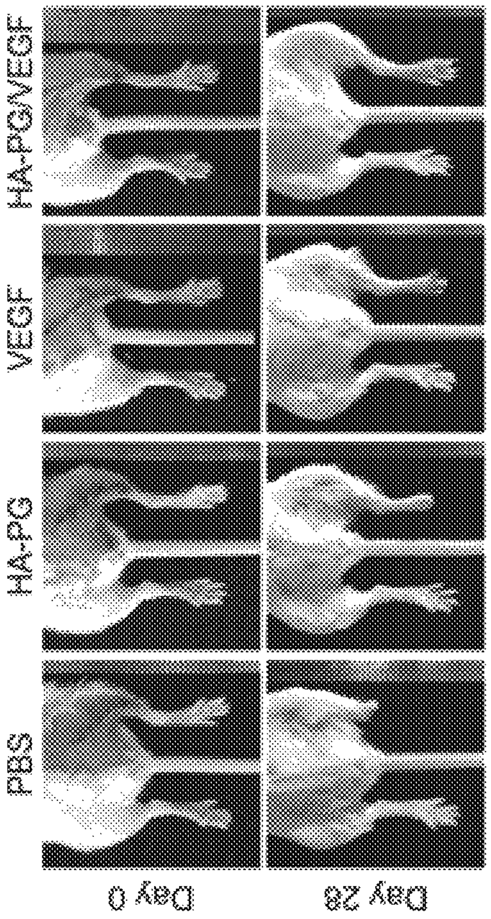
FIGS. 16A, 16B, 16C, 16D, 16E, and 16F illustrate VEGF delivery and therapeutic effects of a hydrogel prepared by using $NaIO_4$ in a hindlimb ischemic mouse model.
Figure 16B:
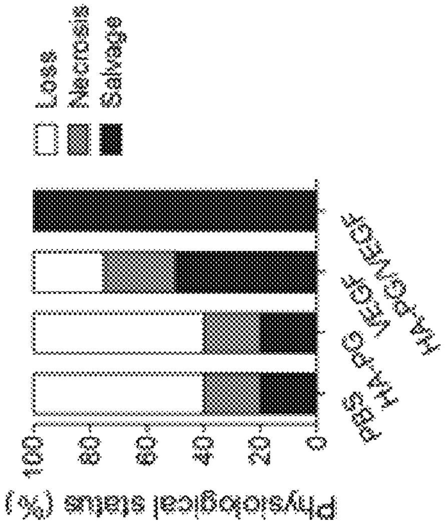
Figure 16D:
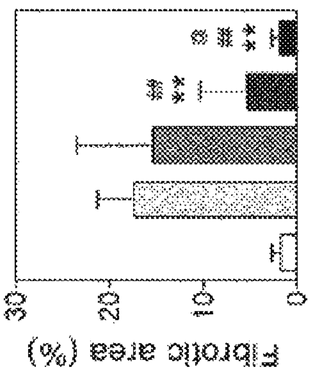
Figure 16C:
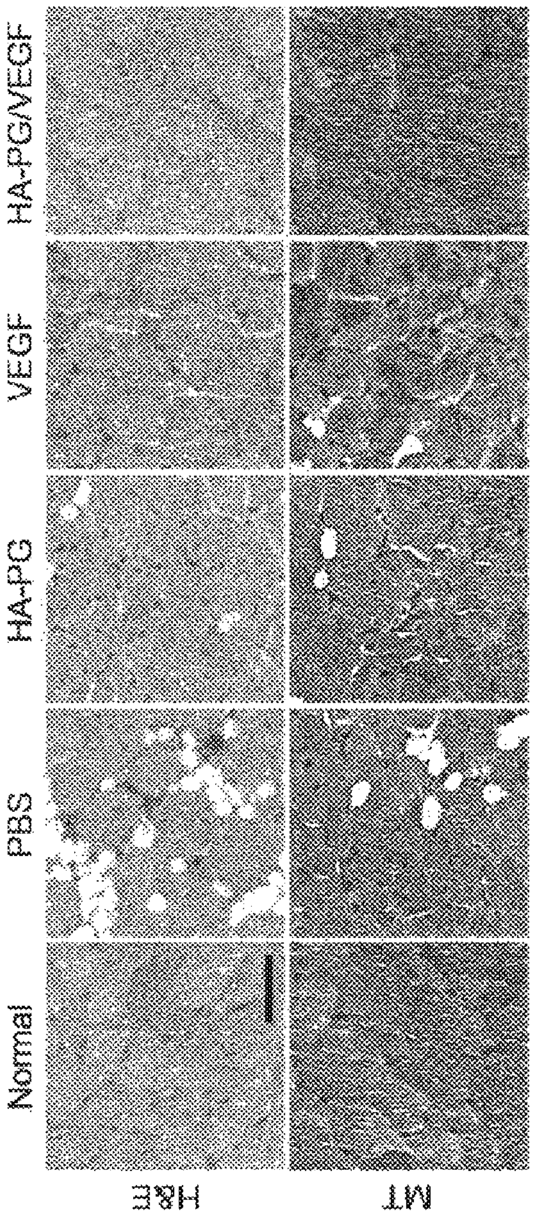
Figure 16E:
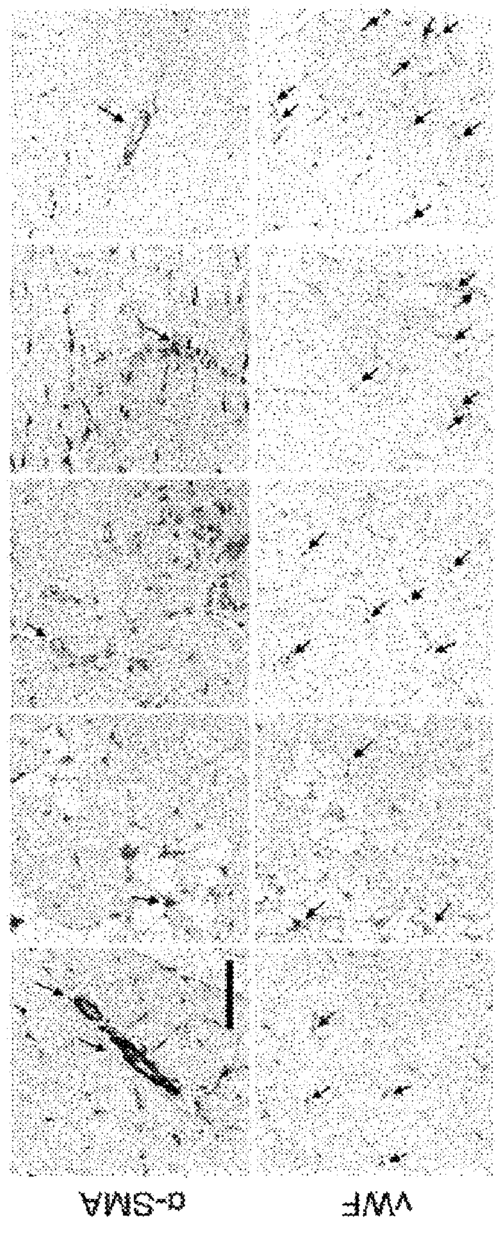
Figure 16F:
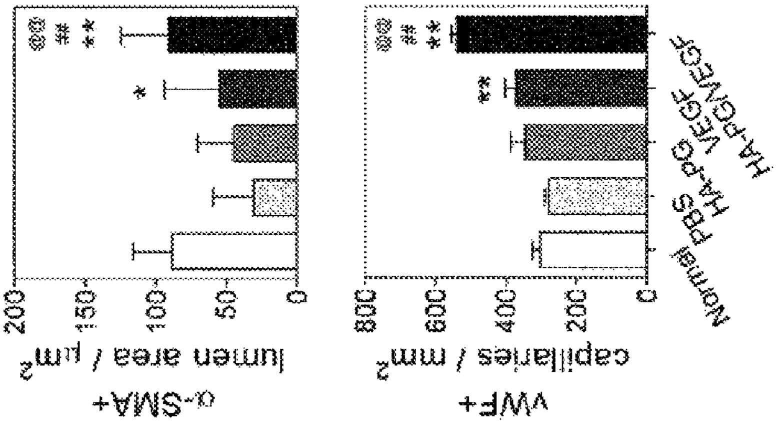
Figure 17A:
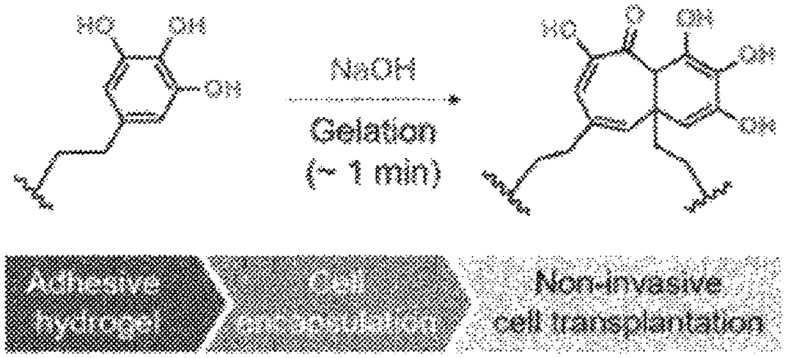
FIGS. 17A, 17B, and 17C illustrate preparation of a tissue-adhesive HA-PG hydrogel using NaOH-mediated crosslinking.
Figure 17B:
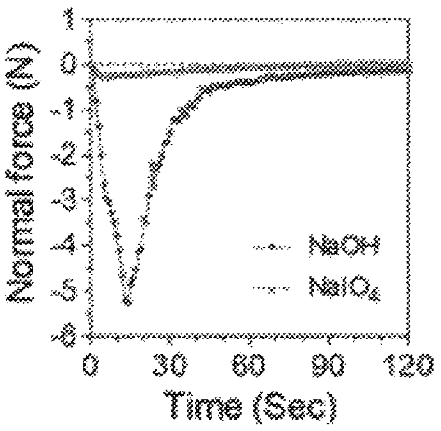
Figure 17C:
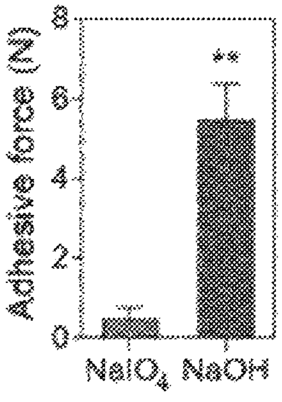
Figure 18:
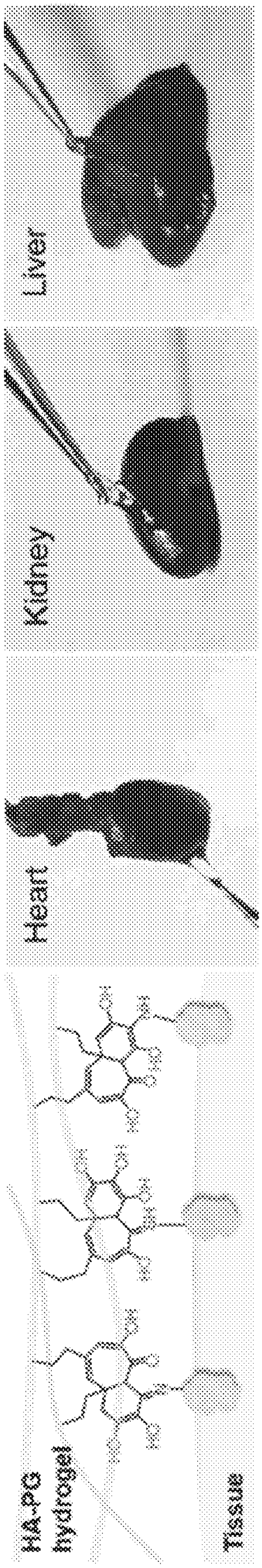
FIG. 18 illustrates adhesion chemistry of a NaOH-induced HA-PG hydrogel, and also illustrates photographs showing direct adhesion of the hydrogel to various mouse organs (heart, kidney, and liver).
Figure 19A:
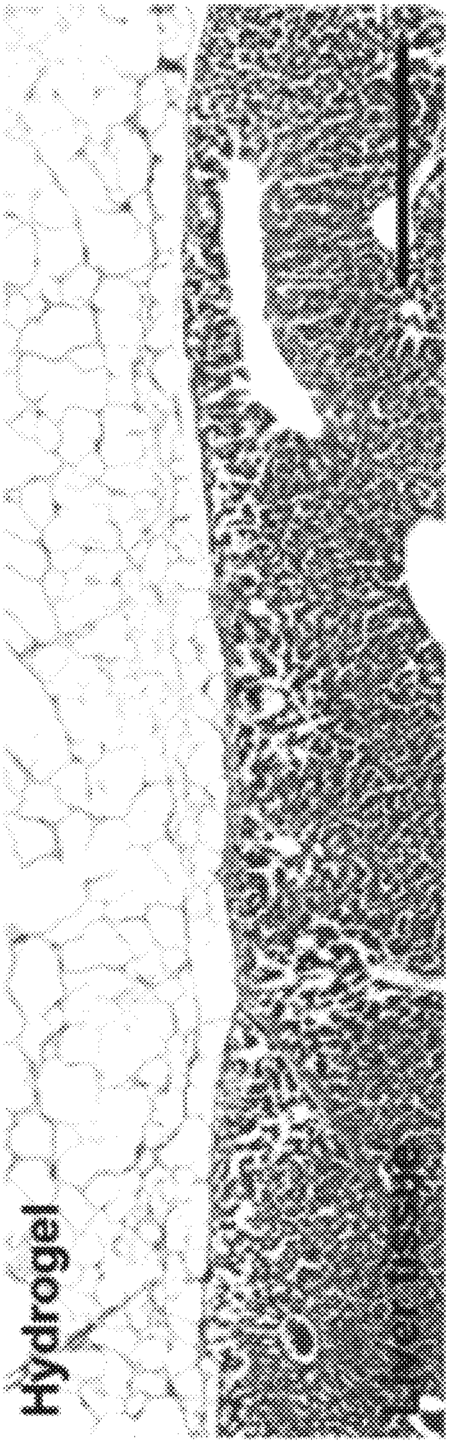
FIG. 19A illustrates a result obtained by applying a NaOH-induced HA-PG hydrogel on a mouse liver surface and performing H&E staining of the hydrogel adhered on the surface of liver tissue after 7 days (scale bar=500 μm).
Figure 19B:
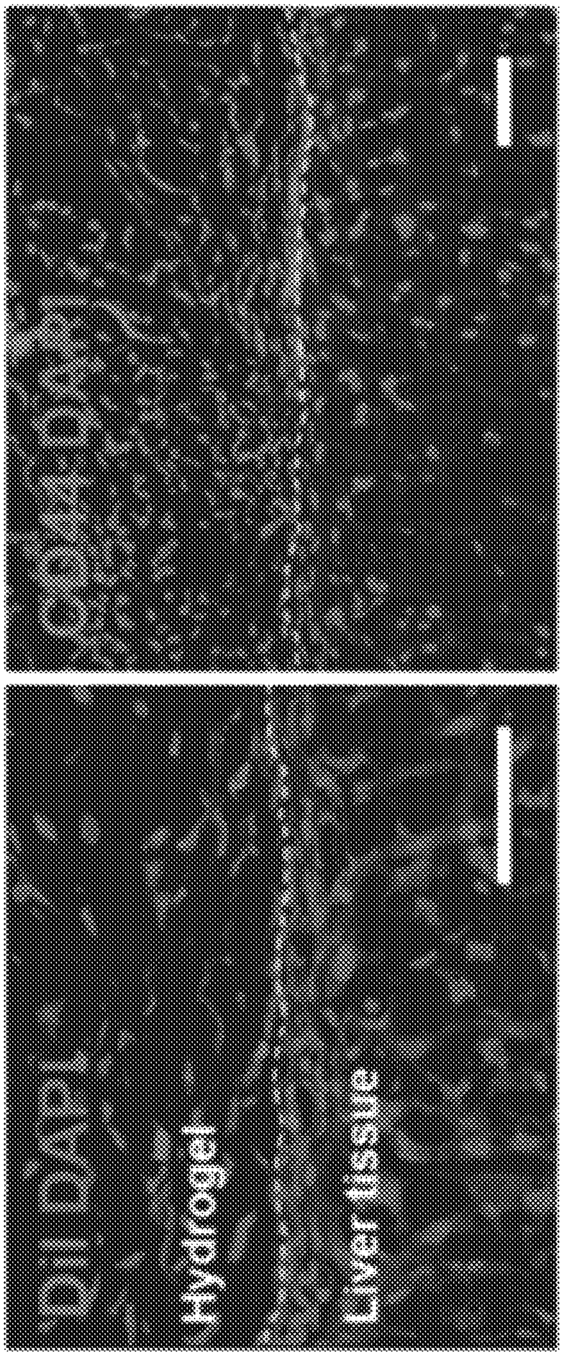
FIG. 19B illustrates a result obtained by transplanting human adipose tissue-derived stem cells (hADSCs) onto the mouse liver using HA-PG crosslinked with NaOH, and then representing together immunostaining of original liver tissue and the hADSCs in the hydrogel structure of the present invention. Cells which had been labeled with Dil prior to transplantation were detected (left). Immunostaining was performed for CD44 and cell nuclei were counter-stained with DAPI (right) (scale bar=500 μm).
Figure 20A:
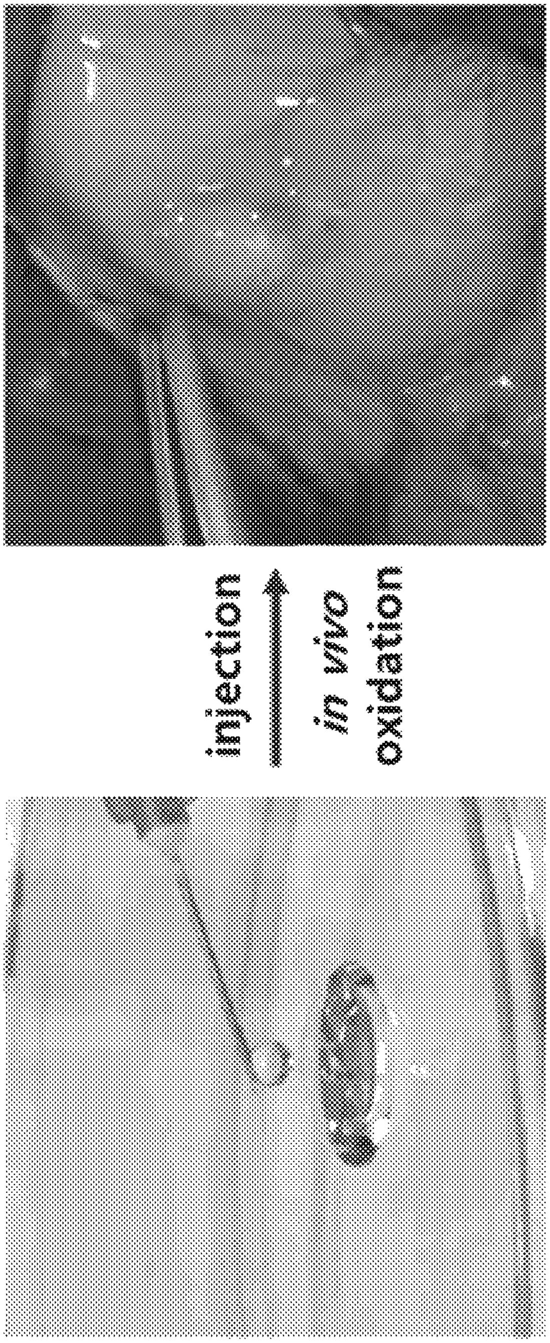
Figure 20B:
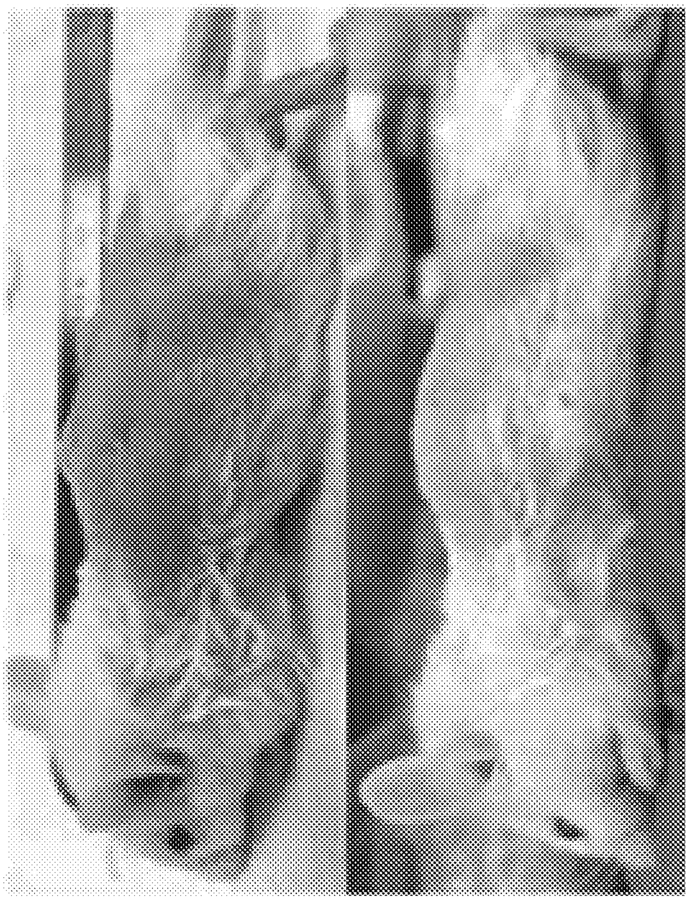
Figure 21A:
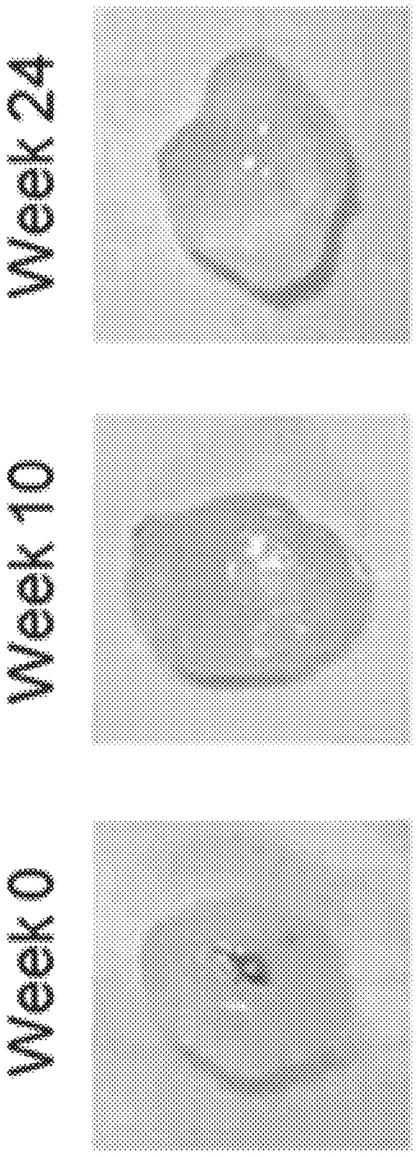
Figure 21B:
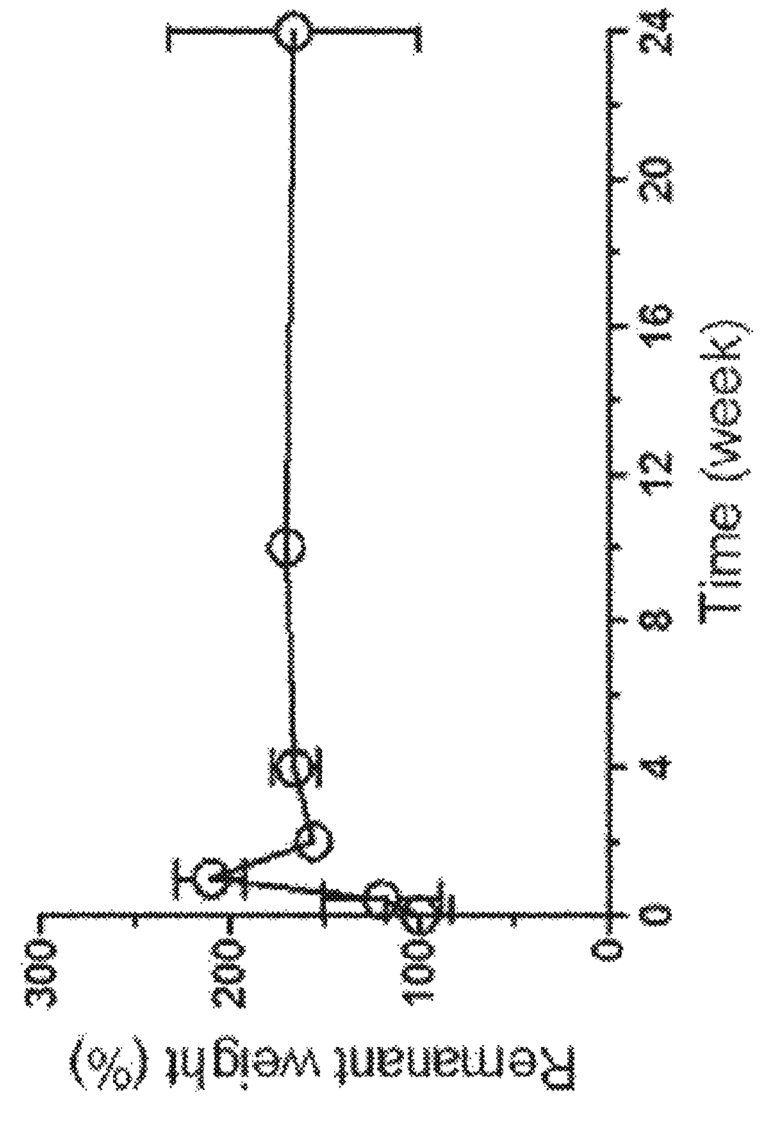

HA-PG microparticles into which VEGFs (Peprotech, Rocky Hill, N.J., USA) are incorporated were applied to facilitate therapeutic angiogenesis in peripheral vascular diseases. Intramuscular injection of VEGFs contained in HA-PG microparticles (VEGF loading dose: 6 μg per mouse) showed a remarkably improved therapeutic effect in a limb ischemic mouse model prepared by resection and ligation of femoral artery. Mice (balb/c, 6-week-old female) were obtained from OrientBio Inc. After 4 weeks of injection, there was no leg cut or tissue necrosis in the group treated with the VEGF-containing HA-PG microparticles. On the other hand, only 20% of the group treated with PBS or only HA-PG without VEGFs exhibited improvement in ischemic legs (FIG. 16A). Single bolus administration of VEGFs at the same dose (6 pf per mouse) showed slight improvement in ischemic legs; however, 50% of limb ischemic mice still exhibited leg loss or tissue necrosis (FIG. 16B). In addition, histological analysis identified by H&E and Masson's trichrome (MT) staining showed minimal muscle damage and fibrosis formation in an HA-PG/VEGF group of the ischemic mouse model (FIGS. 16C and 16D). In addition, immunohistochemical analysis using α-smooth muscle actin (α-SMA) and von Willebrand factor (vWF) for arteriole staining and capillary staining, respectively, showed that arteriole and capillary are remarkably increased in the HA-PG/VEGF group as compared with controls (PBS, HA-PG, and VEGF) (FIGS. 16E and 16F). These results show substantial improvement in angiogenesis. NaOH-mediated crosslinking was used to prepare an adhesive hydrogel scaffold for non-invasive and injection-free cell transplantation (FIG. 17A). From previous studies, it has been identified that catechol-modified polymers exhibit strong tissue adhesive strength through high binding affinity to various nucleophiles of oxidized catechol in proteins.

Example 5

Identification of Gelation of Hyaluronic Acid Filler Composition Using Oxidizing Power in Body and Wrinkle-Improving Effect Thereof 5-1. Formation and Maintenance of Hydrogels Using Oxidizing Power in Body The HA-PG solution prepared in Preparation Example 1 was injected subcutaneously into mice. Then, it was identified whether or not gelation of the injected HA-PG solution can proceed in the body without addition of a crosslinking agent. In addition, changes in the weight of the formed HA-PG hydrogel were measured, under a condition in the body, for about 6 months, to identify whether the formed HA-PG hydrogel can be maintained in the body for a long time.

Figure 22A:
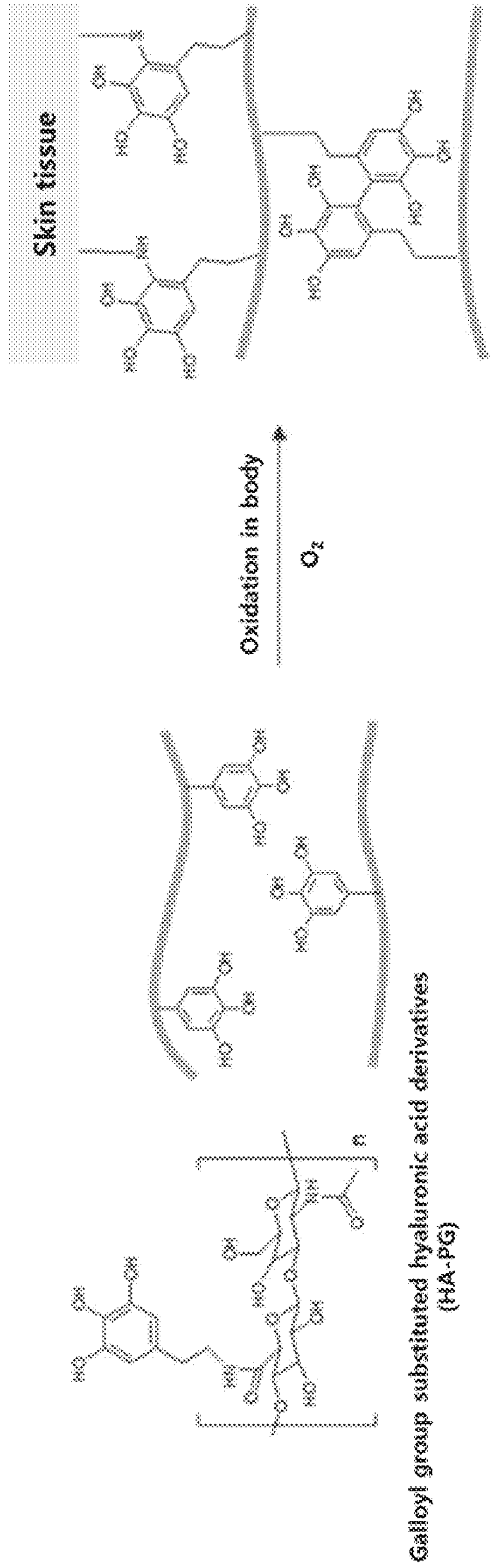
Figure 22B:
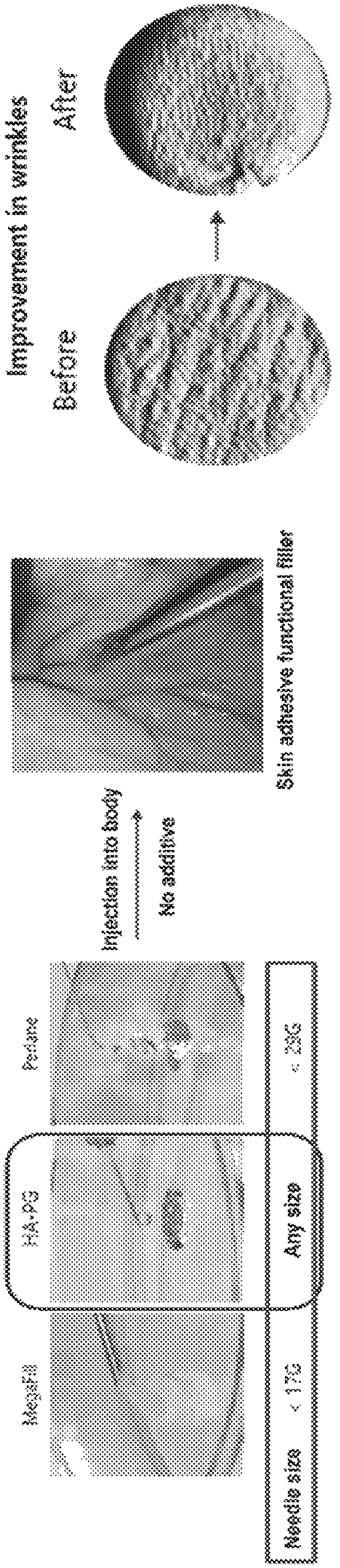

As a result, as illustrated in FIGS. 20A, 20B, 21A, and 21B, it was found that the HA-PG solution, which has been injected subcutaneously in a liquid state, is gelated within 5 minutes to form an HA-PG hydrogel in the body, and that the formed HA-PG hydrogel is maintained well in the body in a transparent state for 6 months without any large difference in weight. In addition, as illustrated in FIGS. 22A and 22B, in a case where the HA-PG solution is exposed to an oxidizing condition in the body, quinones are easily formed among gallol groups having a strong self-oxidizing ability, so that hyaluronic acid is polymerized and an HA-PG hydrogel is formed. Accordingly, it was found that unlike filler products (Megafill, Perlane) which are composed of formulations in a polymerized form, the filler composition of the present invention can be used as a formulation in a solution state, which allows for easier injection into the skin and allows a variety of additional ingredients to be contained. That is, the HA-PG solution of the present invention formed a hydrogel in the body without addition of a crosslinking agent and could be stably maintained therein. From this, it was possible to identify a possibility of utilizing the HA-PG solution as a filler composition.

5-2. Identification of Wrinkle-Improving Effect

Figure 23A:
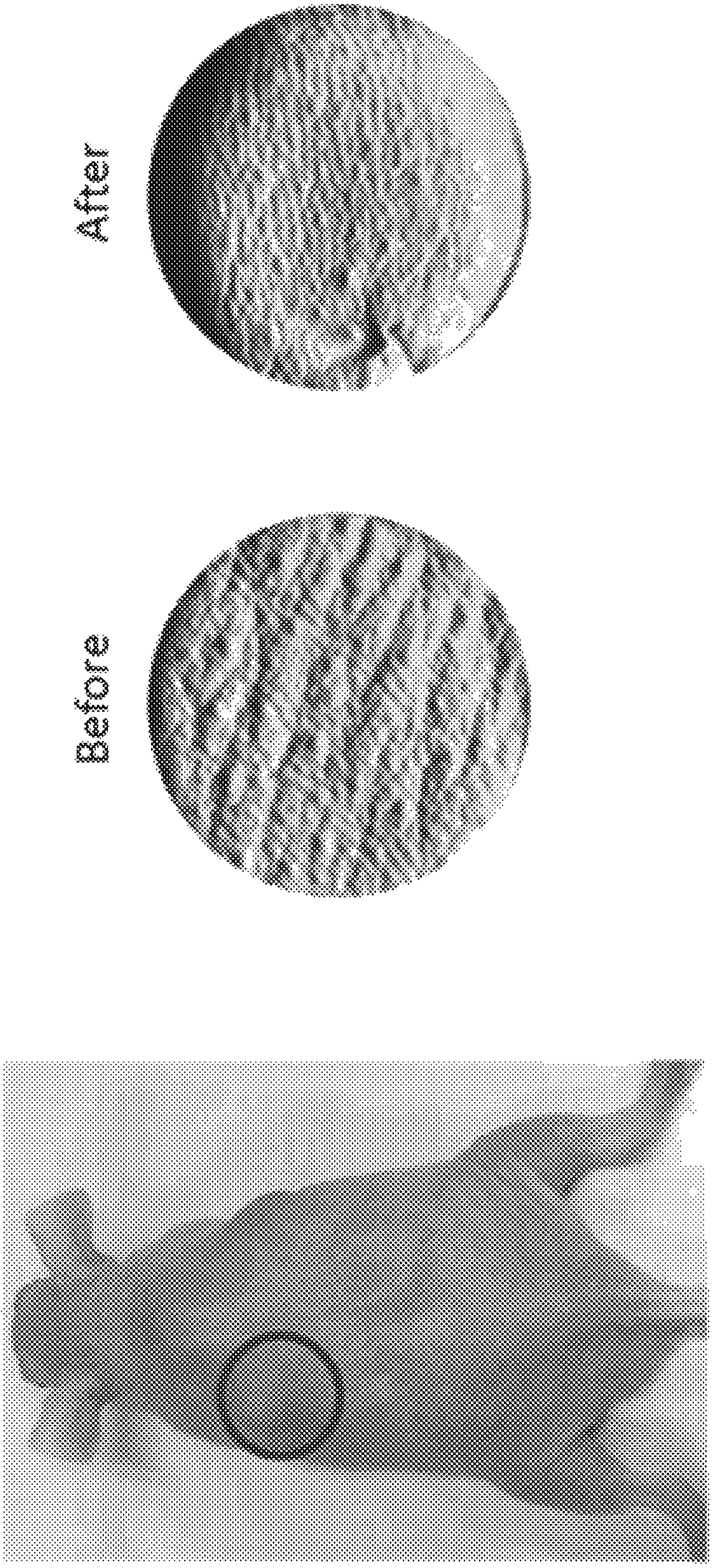
Figure 23B:
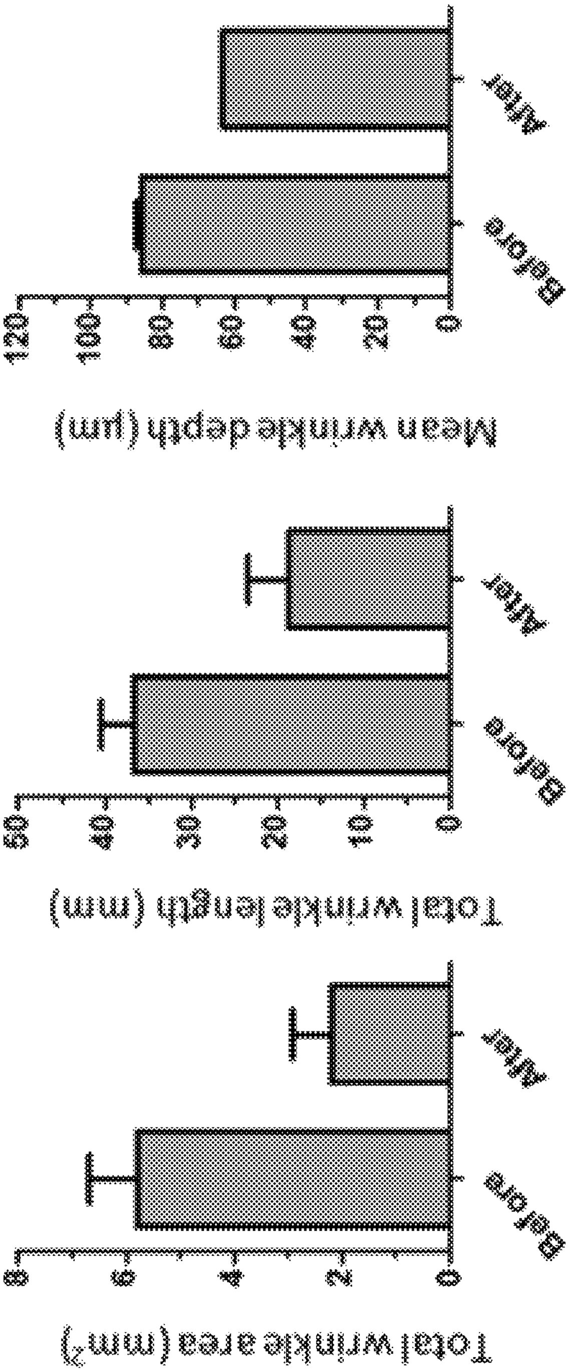
Figure 24A:
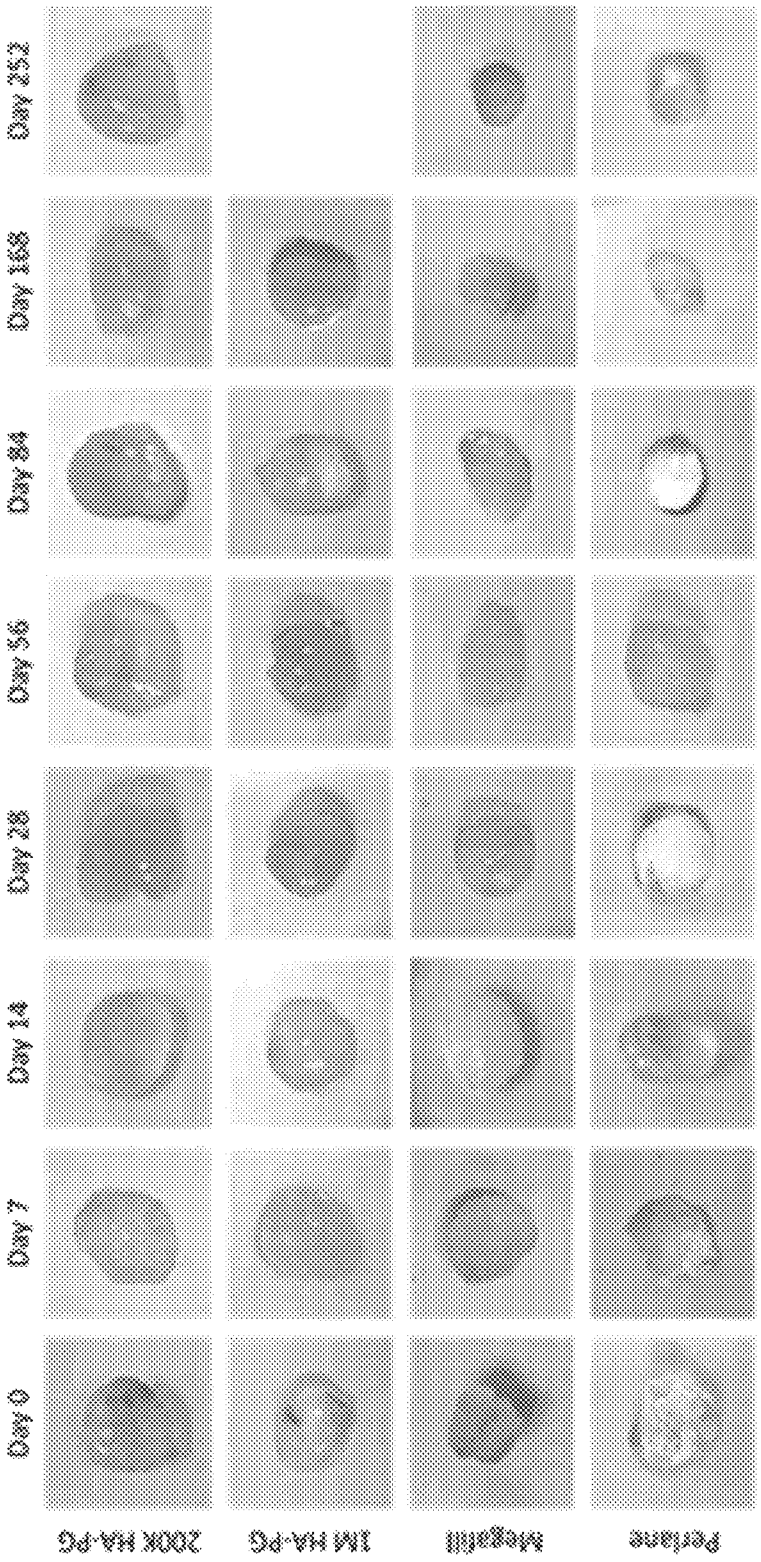
Figure 24B:
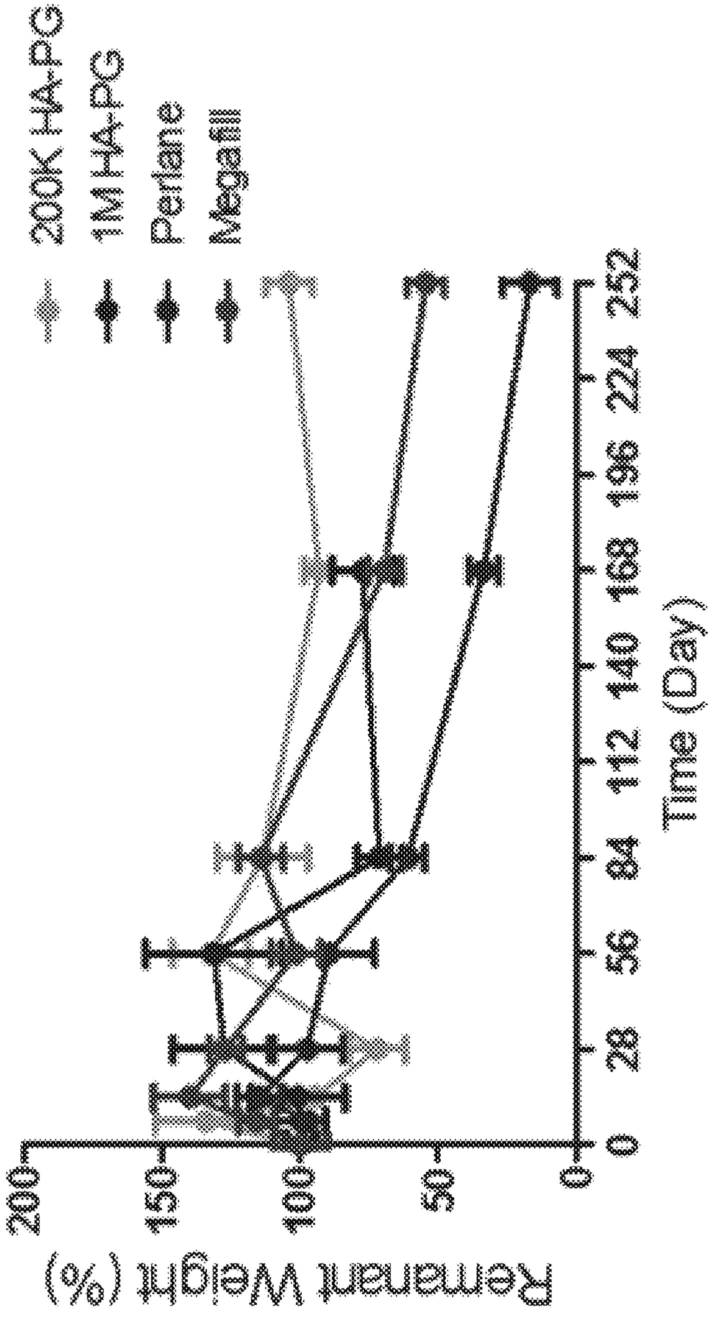
Figure 25A:
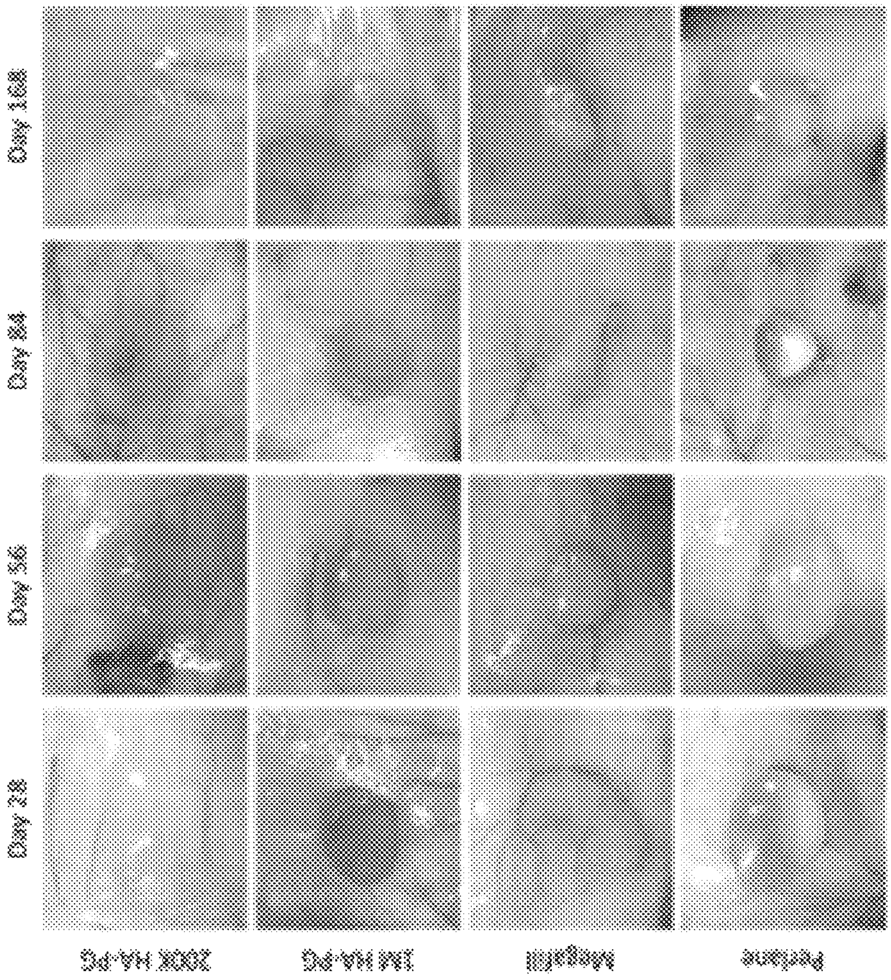
Figure 25B:
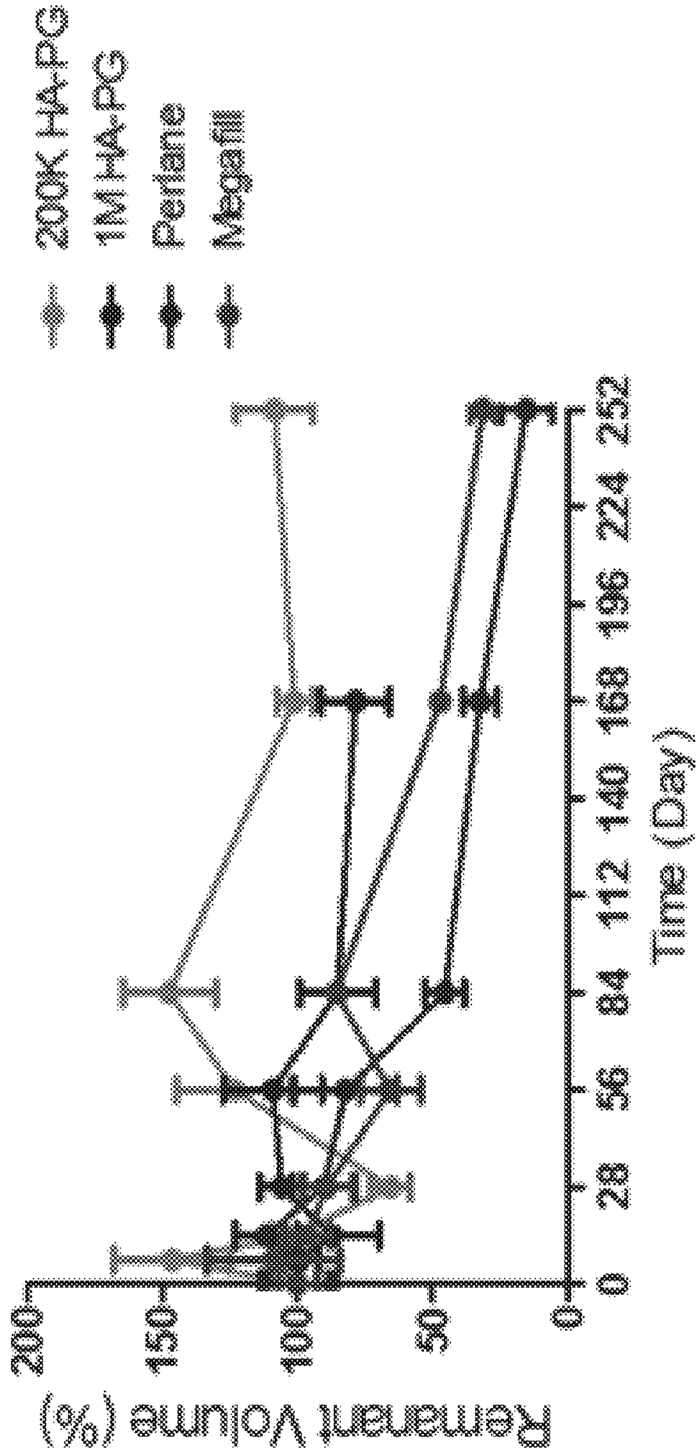

Based on the results in Example 5-1, a wrinkle-improving effect of the HA-PG solution was identified. Specifically, hairless mice were given Calcitriol at 0.2 μg/day each for 5 times a week over a total of 6 weeks, so that skin wrinkles were induced. Then, the HA-PG solution was injected subcutaneously into the skin, and the wrinkled skin before and after the injection was made into replicas. The area, length, and depth of the wrinkles were measured using a wrinkle analysis machine, and compared. As a result, as illustrated in FIGS. 23A and 23B, the area, length, and depth of the wrinkles before injection of the HA-PG solution were about 6 $mm^2$, about 36 mm, and about 90 μm, respectively, whereas those after injection of the HA-PG solution were about 2 $mm^2$, about 19 mm, and about 68 μm, respectively. From this, it was possible to identify that the area, length, and depth of the wrinkles are remarkably decreased. These results indicate that the HA-PG solution of the present invention can be utilized as a filler composition for improving skin wrinkles.

Figure 26B:
Figure 26A:

5-3. Comparison with Existing Filler Products (1) Comparison in Terms of Adhesive Strength and Fixability in Body In order to more specifically identify a possibility of utilizing the HA-PG solution as a filler, for HA-PG hydrogels based on hyaluronic acid derivatives having various molecular weights (200 KDa, 1 MDa) and commercially available conventional filler products (Megafill, Perlane), maintenance and degradation patterns thereof in the body were measured for about 9 months and compared. In addition, for the hydrogels produced by the HA-PG solution of the present invention and the Perlane product, adhesive strength or fixability in the body were compared. As a result, as illustrated in FIGS. 24A, 24B, 25A, and 25B, it was possible to identify that for the Megafill and Perlane products, weight and volume of the hydrogel in the body tend to decrease from about one month after the day of injection, whereas for the HA-PG hydrogels, shapes thereof are maintained for 9 months without large changes in weight and volume. It was found that the HA-PG hydrogels have an excellent ability to be maintained in the body. In addition, for the hydrogels, adhesive strength in the body was identified. As a result, as illustrated in FIGS. 26A and 26B, it was possible to identify that the Perlane product exhibits a phenomenon in which the hydrogel produced thereby is not fixed to the skin and leans to a specific site, whereas the hydrogel produced by the HA-PG solution is well maintained in the body by adhering and being fixed to the injection site. Such excellent adhesive strength in the body is a result of the reaction between a functional group, such as an amine group and a thiol group, existing on the skin and the hyaluronic acid derivative of the present invention (FIG. 22A). That is, the HA-PG solution of the present invention exhibits better stability and adhesiveness in the body than the existing filler products.

(2) Comparison of Injectability (Injectability Test)

Figure 27:
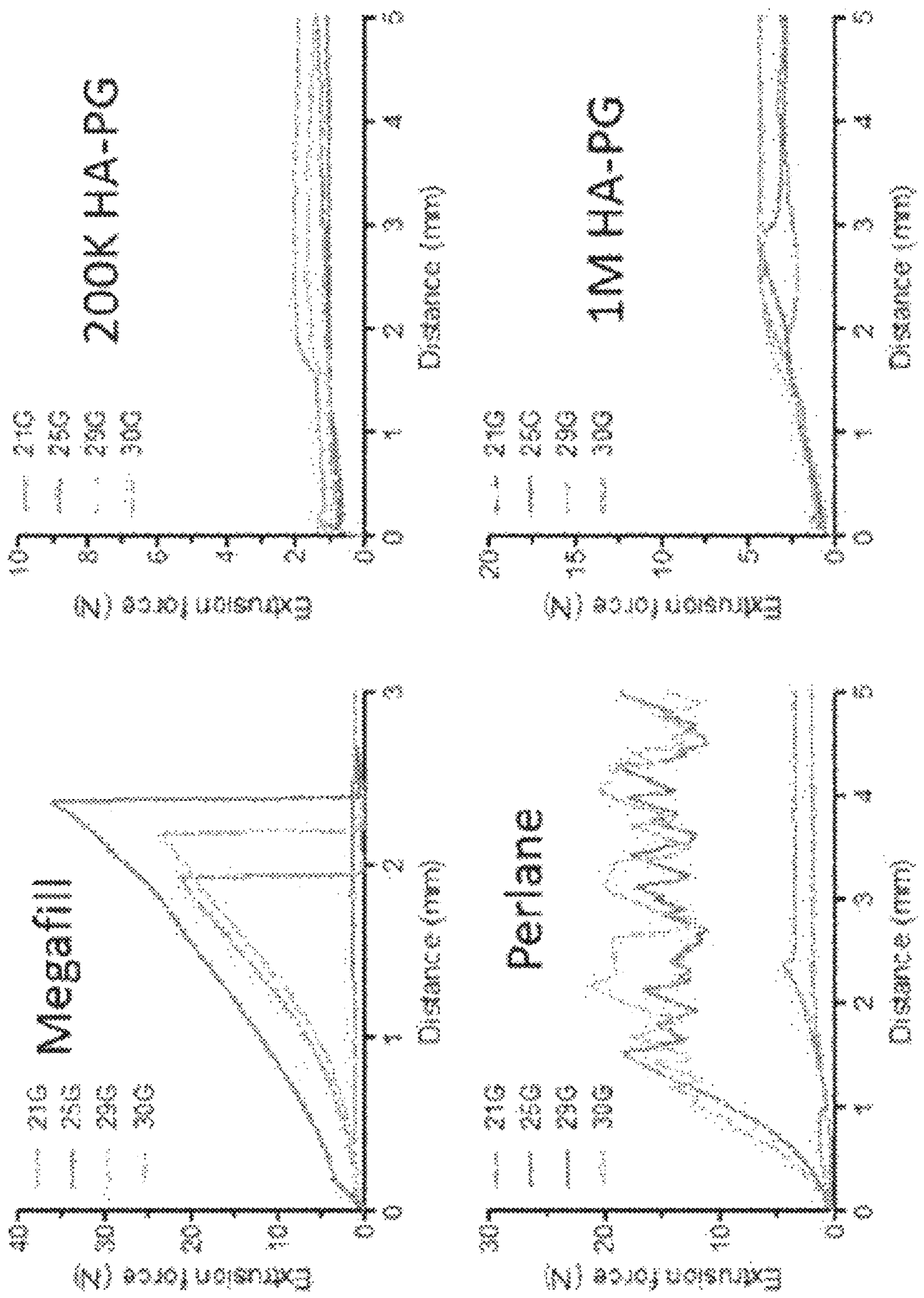
FIG. 27 illustrates results obtained by making a comparison with conventional filler products (Megafill, Perlane) in terms of injectability, and such results were obtained by identifying changes in extrusion force while injecting the HA-PG solutions according to the present invention (200

In order to specifically identify excellent injectability of the HA-PG solution, for the HA-PG hydrogels based on hyaluronic acid derivatives with various molecular weights (200 KDa, 1 MDa) and commercially available conventional filler products (Megafill, Perlane), changes in extrusion force depending on injection needle sizes (21 G, 25 G, 29 G, 30 G) were not only measured using the Universal Testing Machine (UTM), but also the break loose force, which is a force required to initially move a syringe, and the dynamic glide force, which is a force required to maintain motility of a moving syringe, were quantified and compared. As a result, as illustrated in FIGS. 27, 28A, and 28B, Megafill was not extruded in a small-sized injection needle due to a large particle size, and extrusion was possible only at 21 G or less. Even in a case of Perlane, extrusion force in an irregular form was exhibited at 29 G and 30 G due to a particle size. On the other hand, in a case of the HA-PG solutions (200 KDa, 1 MDa) of the present invention, it was possible to identify that effective extrusion is achieved even with a small force in all sizes of needles including 29 G and 30 G. In addition, break loose forces and dynamic glide forces were compared. As a result, as illustrated in FIGS. 29A and 29B, as compared with Megafill, for which measurement was not possible due to poor extrusion, and Perlane showing a high force value, the HA-PG solutions of the present invention (200K, 1M) exhibited a remarkably low force value. Thus, it was found that the HA-PG solution of the present invention can be easily injected regardless of extrusion force for injection, that is, an injection needle size. These results indicate that the HA-PG solutions of the present invention can be injected directly to a target site and can be more stably injected.

5-4. Functional Filler Composition Containing Cell Growth Factor

In order to identify application as a functional filler, an HA-PG solution in which epithelial cell growth factors (EGFs; 20 ng/ml, 1 μm/ml, 20 μg/ml) are encapsulated was injected into the skin of hairless mice in which wrinkles had been induced by the method of Example 5-2; the wrinkled skin before and after the injection was made into replicas; and the area, length, and depth of the wrinkles were measured using a wrinkle analysis machine, and compared. At one month after the injection of the HA-PG solution in which the EGFs are encapsulated, the skin tissue was collected and OCT frozen sections thereof were constructed. Then, through hematoxylin & eosin (H&E) staining of the OCT frozen sections, histopathological examination was performed. In addition, at one month after injection, into the hairless mice, an HA-PG solution in which EGFs (10 μg/ml) are encapsulated, an HA-PG solution, and Perlane which is an existing product, differences in skin tissue regeneration were compared through H&E and Masson's trichrome (MT) in the same manner as above.

As a result, as illustrated in FIGS. 30A and 30B, it was possible to identify that in a case where the HA-PG solution in which EGFs are encapsulated is injected, regardless of sizes of the formed wrinkles, the area, length, and depth of the wrinkles are all remarkably decreased as compared with before the injection. In addition, as illustrated in FIG. 31, collagen fibers in the dermal layer of the skin were destroyed to show poor density and irregular arrangement; on the other hand, as a concentration of the encapsulated epithelial cell growth factors increased, the collagen fibers tended to be regularly arranged. From this, it was possible to identify significant skin-regenerating and wrinkle-improving effects. In addition, as illustrated in FIGS. 32 and 33, in a case where the HA-PG solution in which the EGFs are encapsulated is injected, it was possible to identify that the epidermal layer thickened due to induction of wrinkles is remarkably thinned as compared with the other comparative groups (No filler, Perlane, HA-PG) and that a collagen density of the dermal layer is largely increased. These results indicate that a cell growth factor for improving skin wrinkles is applied to the HA-PG solution of the present invention, and thus the resultant can be utilized as a functional filler.

Example 6

Preparations for Wound Dressing, Wound Healing Agent, and Adhesion Barrier

In order to identify application as a dressing preparation for wound healing, an HA-PG solution was applied to a wound-induced animal model in which the dorsal skin of mice was incised to a size of 1 cm×1 cm, and then cross-linking was performed with surrounding active oxygen. Then, formation of a hydrogel at the wound site, and thus adhesion of the HA-PG solution to the wound site were identified. As a result, as illustrated in FIG. 34, it was possible to identify that a hydrogel film is formed within 10 minutes after the HA-PG solution has been applied to the wound site, from which the HA-PG solution adheres to the wound site. These results indicate that the HA-PG solution can be utilized as a new type of wound dressing material which has excellent oxidizing ability and can be evenly applied to a wound without any additional additive.

Example 7

Formulation in Powders and Storage Stability Analysis 7-1. Formulation in Powders In order to identify a possibility of formulating a filler composition in powders, as illustrated in FIG. 35, the HA-PG solution of Preparation Example 1 was freeze-dried to prepare a filler composition in a powder form. Thereafter, the filler composition in a powder form was dissolved in PBS (pH 7) to be resolubilized, and then subcutaneously injected into mice to observe whether a hydrogel was formed. As a result, as illustrated in FIG. 36, it was possible to identify that the filler composition of the present invention, which has been resolubilized in a freeze-dried powder state, is crosslinked by oxidizing power in the body to form a hydrogel as before. These results indicate that the filler composition of the present invention, which can be formulated in powders, can provide users with ease of use and ease of storage.

7-2. Storage Stability Analysis

In order to identify specific storage stability of the filler composition, it was first identified whether the HA-PG solution of Preparation Example 1 is gelated in a storage container while storing the same at room temperature (25° C.) or a refrigerated (4° C.) state. In addition, nitrogen gas was injected into the storage container to block contact between the HA-PG solution and oxygen, and then stored in a refrigerated (4° C.) state for 3 days; on the other hand, the HA-PG solution was stored as a frozen (−80° C.) state for 10 days. Then, these solutions were injected subcutaneously into mice to observe whether hydrogels were formed. As a result, as illustrated in FIG. 37, due to high oxidizing power, gelation of the filler composition of the present invention proceeded within one day at room temperature and within three days at a refrigerated state. On the other hand, as illustrated in FIG. 38, it was possible to identify that under a condition where oxygen is blocked, in a case of being in a refrigerated state, gelation does not proceed even after 3 days have lapsed; in a case where the HA-PG solution is stored in a frozen state and then thawed after 10 days, the HA-PG solution maintains properties of a solution, and even in a case where this HA-PG solution is injected into the skin of mice, such an HA-PG solution is crosslinked due to oxidizing power in the body to form a hydrogel as before. These results indicate that the filler composition of the present invention can be stored for a longer period of time under a condition where oxygen is blocked or in a frozen state.

It will be understood by those skilled in the art to which the present invention belongs that the foregoing description of the present invention is for illustrative purposes and that various changes and modifications may be readily made without departing from the technical spirit or essential features of the present invention. Therefore, it is to be understood that the above-described examples are illustrative in all aspects and not restrictive.

The invention claimed is:

1. A composition comprising a hyaluronic acid-pyrogallol conjugate comprising one or more hyaluronic acid repeat units represented by the following Formula 1:

(Formula 1)

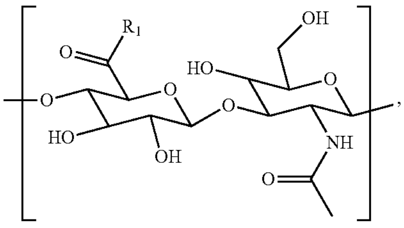

, wherein $R_1$ is a hydroxyl group or

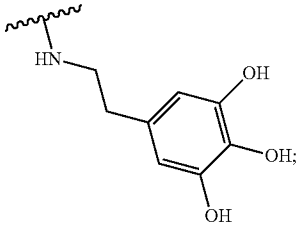 [SMILES: *NCCc1cc(O)c(O)c(O)c1]

;

wherein one or more of the hyaluronic acid repeat groups of Formula 1 comprises a pyrogallol group as represented by the following Formula 5:

(Formula 5)

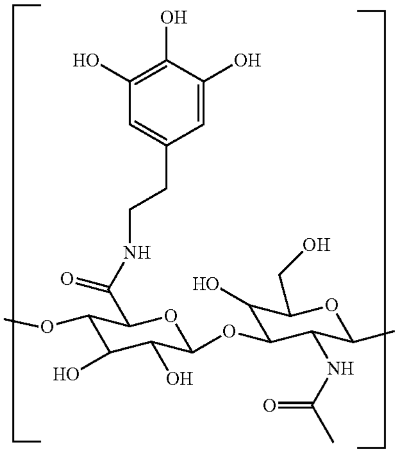

;

wherein the hyaluronic acid-pyrogallol conjugate has a pyrogallol group substitution rate of about 2% to about 20%.

2. The composition of claim 1, wherein the hyaluronic acid-pyrogallol conjugate has a molecular weight of 10,000 Da to 2,000,000 Da.

3. The composition of claim 1, wherein the hyaluronic acid-pyrogallol conjugate is contained in an amount of 0.1% (w/v) to 15% (w/v) with respect to the total weight of the composition composition.

4. The composition of claim 1, wherein the composition is in a liquid state ex vivo and forms a gelated state without an added crosslinking agent in vivo.

5. The composition of claim 1, wherein the composition is administered into a site any site-selected from the group consisting of a tear trough region, a glabellar frown line region, an eye-rim region, a forehead region, a nasal bridge region, a nasolabial line region, a marionette line region, and a neck wrinkle region.

6. The composition of claim 1, further comprising one or more drugs selected from the group consisting of an antibody, an antibody fragment, a nucleic acid including DNA, RNA, or siRNA, a peptide, a gene, a protein, a stem cell, and a chemical compound.

* * * * *